United States Patent
Bechtold et al.

(10) Patent No.: US 12,178,816 B2
(45) Date of Patent: *Dec. 31, 2024

(54) IMMEDIATE RELEASE PHARMACEUTICAL FORMULATION OF 4-[3-(4-CYCLOPROPANECARBONYL-PIPERAZINE-1-CARBONYL)-4-FLUORO-BENZYL]-2H-PHTHALAZIN-1-ONE

(71) Applicant: KUDOS PHARMACEUTICALS LIMITED, Cambridge (GB)

(72) Inventors: Michael Karl Bechtold, Macclesfield (GB); Julie Kay Cahill, Macclesfield (GB); Katja Maren Fastnacht, Macclesfield (GB); Kieran James Lennon, Macclesfield (GB); Bernd Harald Liepold, Macclesfield (GB); Claudia Bettina Packhaeuser, Macclesfield (GB); Benedikt Steitz, Macclesfield (GB)

(73) Assignee: KUDOS PHARMACEUTICALS LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/785,063

(22) Filed: Jul. 26, 2024

(65) Prior Publication Data
US 2024/0398796 A1 Dec. 5, 2024

Related U.S. Application Data

(63) Continuation of application No. 18/755,544, filed on Jun. 26, 2024, which is a continuation of application No. 18/312,375, filed on May 4, 2023, now Pat. No. 12,048,695, which is a continuation of application No. 17/483,070, filed on Sep. 23, 2021, now abandoned, which is a continuation of application No. 16/863,074, filed on Apr. 30, 2020, now abandoned, which is a continuation of application No. 16/224,096, filed on Dec. 18, 2018, now abandoned, which is a continuation of application No. 15/707,376, filed on Sep. 18, 2017, now abandoned, which is a continuation of application No. 15/449,353, filed on Mar. 3, 2017, now abandoned, which is a continuation of application No. 14/688,326, filed on Apr. 16, 2015, now abandoned, which is a continuation of application No. 13/911,151, filed on Jun. 6, 2013, now abandoned, which is a continuation of application No. 12/574,801, filed on Oct. 7, 2009, now Pat. No. 8,475,842.

(60) Provisional application No. 61/103,347, filed on Oct. 7, 2008.

(51) Int. Cl.
*A61K 31/502* (2006.01)
*A61K 9/14* (2006.01)
*A61K 9/20* (2006.01)
*A61K 47/02* (2006.01)
*A61K 47/12* (2006.01)
*A61K 47/20* (2006.01)
*A61K 47/32* (2006.01)

(52) U.S. Cl.
CPC .......... *A61K 31/502* (2013.01); *A61K 9/2009* (2013.01); *A61K 9/2013* (2013.01); *A61K 9/2027* (2013.01); *A61K 9/2095* (2013.01); *A61K 47/02* (2013.01); *A61K 47/12* (2013.01); *A61K 47/20* (2013.01); *A61K 47/32* (2013.01)

(58) Field of Classification Search
None
See application file for complete search history.

(56) References Cited

U.S. PATENT DOCUMENTS

| 3,813,384 | A | | 5/1974 | Vogelsang et al. |
| 4,665,181 | A | | 5/1987 | Thomas et al. |
| 4,801,460 | A | | 1/1989 | Goertz et al. |
| 4,841,047 | A | | 6/1989 | Engel et al. |
| 4,880,585 | A | * | 11/1989 | Klimesch .................. A61J 3/10 425/327 |

(Continued)

FOREIGN PATENT DOCUMENTS

| AU | 4610472 A1 | 3/1974 |
| CA | 2352194 A1 | 4/2001 |

(Continued)

OTHER PUBLICATIONS

Leuner, Christian, and Jennifer Dressman. "Improving drug solubility for oral delivery using solid dispersions." European journal of Pharmaceutics and Biopharmaceutics 50.1 (2000): 47-60. (Year: 2000).*

(Continued)

*Primary Examiner* — Bethany P Barham
*Assistant Examiner* — Peter Anthopolos
(74) *Attorney, Agent, or Firm* — Finnegan ,Henderson, Farabow Garret & Dunner LLP

(57) ABSTRACT

The present invention relates to a pharmaceutical formulation comprising the drug 4-[3-(4-cyclopropanecarbonyl-piperazine-1-carbonyl)-4-fluoro-benzyl]-2H-phthalazin-1-one in a solid dispersion with a matrix polymer that exhibits low hygroscopicity and high softening temperature, such as copovidone. The invention also relates to a daily pharmaceutical dose of the drug provided by such a formulation. In addition, the invention relates to the use of a matrix polymer that exhibits low hygroscopicity and high softening temperature in solid dispersion with 4-[3-(4-cyclopropanecarbonyl-piperazine-1-carbonyl)-4-fluoro-benzyl]-2H-phthalazin-1-one for increasing the bioavailability of the drug.

30 Claims, 46 Drawing Sheets

(56) References Cited

U.S. PATENT DOCUMENTS

| | | | |
|---|---|---|---|
| 4,957,681 A * | 9/1990 | Klimesch | B29C 45/0001 222/77 |
| 5,032,617 A | 7/1991 | Lee et al. | |
| 5,041,653 A | 8/1991 | Lee et al. | |
| 5,116,986 A | 5/1992 | Bomhard et al. | |
| 5,215,738 A | 6/1993 | Lee et al. | |
| 5,556,856 A | 9/1996 | Engel et al. | |
| 5,587,384 A | 12/1996 | Zhang et al. | |
| 5,648,355 A | 6/1997 | Theoharides et al. | |
| 5,817,674 A | 10/1998 | Clemence et al. | |
| 5,854,264 A | 12/1998 | Anthony et al. | |
| 5,854,265 A | 12/1998 | Anthony et al. | |
| 5,859,035 A | 1/1999 | Anthony et al. | |
| 5,872,136 A | 2/1999 | Anthony et al. | |
| 5,874,444 A | 2/1999 | West et al. | |
| 5,874,452 A | 2/1999 | Anthony et al. | |
| 5,880,128 A | 3/1999 | Doll et al. | |
| 5,880,140 A | 3/1999 | Anthony et al. | |
| 5,883,105 A | 3/1999 | Anthony et al. | |
| 5,886,178 A | 3/1999 | Allen et al. | |
| 5,939,557 A | 8/1999 | Anthony et al. | |
| 6,004,979 A | 12/1999 | Clemence et al. | |
| 6,011,035 A | 1/2000 | Snutch et al. | |
| 6,051,253 A * | 4/2000 | Zettler | B30B 11/227 424/467 |
| 6,051,574 A | 4/2000 | Anthony et al. | |
| 6,060,038 A | 5/2000 | Burns et al. | |
| 6,063,930 A | 5/2000 | Dinsmore et al. | |
| 6,080,870 A | 6/2000 | Anthony et al. | |
| 6,197,785 B1 | 3/2001 | Jackson et al. | |
| 6,294,533 B1 | 9/2001 | Snutch et al. | |
| 6,310,059 B1 | 10/2001 | Snutch et al. | |
| 6,340,684 B1 | 1/2002 | Napoletano et al. | |
| 6,387,897 B1 | 5/2002 | Snutch et al. | |
| 6,426,415 B1 | 7/2002 | Jackson et al. | |
| 6,465,467 B1 | 10/2002 | Nilsson et al. | |
| 6,476,048 B1 | 11/2002 | Szabo et al. | |
| 6,492,375 B2 | 12/2002 | Snutch et al. | |
| 6,498,160 B2 | 12/2002 | Napoletano et al. | |
| 6,514,983 B1 | 2/2003 | Li et al. | |
| 6,514,984 B1 | 2/2003 | Watanabe et al. | |
| 6,552,016 B1 | 4/2003 | Baxter et al. | |
| 6,617,322 B2 | 9/2003 | Snutch et al. | |
| 6,635,642 B1 | 10/2003 | Jackson et al. | |
| 6,677,333 B1 | 1/2004 | Seko et al. | |
| 6,891,041 B2 | 5/2005 | Petrov et al. | |
| 6,903,098 B1 | 6/2005 | Lubisch et al. | |
| 6,943,168 B2 | 9/2005 | Snutch et al. | |
| 6,949,554 B2 | 9/2005 | Snutch et al. | |
| 6,951,862 B2 | 10/2005 | Snutch et al. | |
| 6,953,857 B2 | 10/2005 | Nazareet et al. | |
| 7,064,128 B2 | 6/2006 | Snutch et al. | |
| 7,067,665 B2 | 6/2006 | Nazare et al. | |
| 7,071,180 B2 | 7/2006 | Nilsson et al. | |
| 7,151,102 B2 | 12/2006 | Martin et al. | |
| 7,186,726 B2 | 3/2007 | Snutch et al. | |
| 7,196,085 B2 | 3/2007 | Martin et al. | |
| 7,407,957 B2 | 8/2008 | Javaid et al. | |
| 7,449,464 B2 | 11/2008 | Martin et al. | |
| 7,662,818 B2 | 2/2010 | Martin et al. | |
| 7,666,870 B2 | 2/2010 | Javaid et al. | |
| 7,692,006 B2 | 4/2010 | Menear et al. | |
| 7,750,006 B2 | 7/2010 | Martin et al. | |
| 8,475,842 B2 | 2/2013 | Bechtold et al. | |
| 11,633,396 B2 | 4/2023 | Bechtold et al. | |
| 2001/0029258 A1 | 10/2001 | Snutch | |
| 2003/0022819 A1 | 1/2003 | Ling et al. | |
| 2003/0045530 A1 | 3/2003 | Snutch et al. | |
| 2003/0092694 A1 | 5/2003 | Nilsson et al. | |
| 2003/0134843 A1 | 7/2003 | Lubisch et al. | |
| 2003/0195192 A1 | 10/2003 | Haviv et al. | |
| 2003/0195195 A1 | 10/2003 | Haviv et al. | |
| 2004/0014744 A1 | 1/2004 | Haviv et al. | |
| 2004/0023949 A1 | 2/2004 | Baxter et al. | |
| 2004/0034035 A1 | 2/2004 | Snutch et al. | |
| 2004/0044004 A1 | 3/2004 | Snutch et al. | |
| 2004/0067949 A1 | 4/2004 | Grandel et al. | |
| 2004/0147529 A1 | 7/2004 | Snutch et al. | |
| 2004/0176361 A1 | 9/2004 | Fujio et al. | |
| 2004/0192703 A1 | 9/2004 | Snutch et al. | |
| 2004/0209872 A1 | 10/2004 | Snutch et al. | |
| 2004/0242554 A1 | 12/2004 | Nilsson et al. | |
| 2004/0259866 A1 | 12/2004 | Snutch et al. | |
| 2004/0266784 A1 | 12/2004 | Snutch et al. | |
| 2005/0020583 A1 | 1/2005 | Pulici et al. | |
| 2005/0054568 A1 | 3/2005 | Ling et al. | |
| 2005/0059663 A1 | 3/2005 | Martin et al. | |
| 2005/0080096 A1 | 4/2005 | Ishida et al. | |
| 2005/0085476 A1 | 4/2005 | Seko et al. | |
| 2005/0227919 A1 | 10/2005 | Ashworth et al. | |
| 2005/0227999 A1 | 10/2005 | Pajouhesh et al. | |
| 2005/0277629 A1 | 12/2005 | Lansbury et al. | |
| 2006/0030557 A1 | 2/2006 | Haviv et al. | |
| 2006/0084660 A1 | 4/2006 | Snutch et al. | |
| 2006/0142293 A1 | 6/2006 | Martin et al. | |
| 2006/0276391 A1 | 12/2006 | Auricchio et al. | |
| 2007/0093489 A1 | 4/2007 | Javaid et al. | |
| 2007/0185105 A1 | 8/2007 | Snutch et al. | |
| 2008/0194569 A1 | 8/2008 | Buchstaller et al. | |
| 2008/0194570 A1 * | 8/2008 | Juergens | A61P 35/00 514/248 |
| 2008/0255128 A1 | 10/2008 | Javaid et al. | |
| 2022/0249474 A1 | 8/2022 | Bechtold et al. | |

FOREIGN PATENT DOCUMENTS

| | | | |
|---|---|---|---|
| DE | 287032 A5 | 2/1991 | |
| EP | 0030861 B1 | 6/1981 | |
| EP | 0289881 A2 | 4/1988 | |
| EP | 0355750 B1 | 2/1990 | |
| EP | 0389995 B1 | 10/1990 | |
| EP | 0502575 A1 | 9/1992 | |
| EP | 0634404 A1 | 1/1995 | |
| EP | 0699754 B1 | 3/1996 | |
| EP | 0705903 B1 | 4/1996 | |
| EP | 721286 A2 | 7/1996 | |
| EP | 0792643 B1 | 9/1997 | |
| EP | 1477175 A1 | 11/2004 | |
| EP | 1760071 A1 | 3/2007 | |
| FR | 2262513 A1 | 9/1975 | |
| JP | 54156526 | 12/1979 | |
| JP | 58164577 | 9/1983 | |
| JP | 62252774 | 11/1987 | |
| WO | WO 1991/018591 A1 | 12/1991 | |
| WO | WO 1993/014086 A1 | 7/1993 | |
| WO | WO 1994/010151 A1 | 5/1994 | |
| WO | WO 1995/024379 A1 | 9/1995 | |
| WO | WO 1996/019225 A1 | 6/1996 | |
| WO | WO 1996/031501 A1 | 10/1996 | |
| WO | WO 1997/036587 A1 | 10/1997 | |
| WO | WO 1997/038664 A2 | 10/1997 | |
| WO | WO 1997/045412 A1 | 12/1997 | |
| WO | WO-9749384 A1 * | 12/1997 | A61K 9/2031 |
| WO | WO 1998/043477 A1 | 10/1998 | |
| WO | WO 1998/051308 A1 | 11/1998 | |
| WO | WO 1999/008680 A1 | 2/1999 | |
| WO | WO 1999/011624 A1 | 3/1999 | |
| WO | WO 1999/011645 A1 | 3/1999 | |
| WO | WO 1999/011649 A2 | 3/1999 | |
| WO | WO 1999/044612 A1 | 9/1999 | |
| WO | WO 1999/047494 A1 | 9/1999 | |
| WO | WO 2000/005219 A1 | 2/2000 | |
| WO | WO 2000/042040 A1 | 7/2000 | |
| WO | WO 2001/010856 A1 | 2/2001 | |
| WO | WO 2001/012199 A2 | 2/2001 | |
| WO | WO 2001/016136 A2 | 3/2001 | |
| WO | WO 2001/016137 A1 | 3/2001 | |
| WO | WO 2001/021615 A1 | 3/2001 | |
| WO | WO 2001/079184 A1 | 10/2001 | |
| WO | WO 2001/085686 A2 | 11/2001 | |
| WO | WO 2001/087845 A2 | 11/2001 | |
| WO | WO 2001/090077 A1 | 11/2001 | |
| WO | WO 2002/036576 A1 | 5/2002 | |
| WO | WO-0235991 A2 * | 5/2002 | A61K 9/1694 |

(56) References Cited

FOREIGN PATENT DOCUMENTS

| | | | |
|---|---|---|---|
| WO | WO 2002/044157 A2 | 6/2002 | |
| WO | WO 2002/068407 A1 | 9/2002 | |
| WO | WO 2002/090334 A1 | 11/2002 | |
| WO | WO 2003/007959 A1 | 1/2003 | |
| WO | WO 2003/051879 A1 | 6/2003 | |
| WO | WO 2003/055865 A1 | 7/2003 | |
| WO | WO 2003/057145 A2 | 7/2003 | |
| WO | WO 2003/057151 A2 | 7/2003 | |
| WO | WO 2003/063874 A1 | 8/2003 | |
| WO | WO 2003/070726 A1 | 8/2003 | |
| WO | WO 2003/080581 A1 | 10/2003 | |
| WO | WO 2003/093261 A1 | 11/2003 | |
| WO | WO 2004/080976 A1 | 9/2004 | |
| WO | WO-2004100883 A2 * | 11/2004 | ............. A61K 31/52 |
| WO | WO 2005/053662 A1 | 6/2005 | |
| WO | WO-2007001451 A2 * | 1/2007 | ........... A61K 31/496 |
| WO | WO 2008/017867 A2 | 2/2008 | |
| WO | WO 2008/083027 A1 | 7/2008 | |

OTHER PUBLICATIONS

Crowley, Michael M., et al. "Pharmaceutical applications of hot-melt extrusion: part I." Drug development and industrial pharmacy 33.9 (2007): 909-926. (Year: 2007).*

Affar, E. B. et al., "Immunodot blot method for the detection of poly(ADP-ribose) synthesized in vitro and in vivo," Anal. Biochem. (1998) 259(2):280-283.

AL-Dabbagh and Smith, "Species differences in oxidative drug metabolism: some basic considerations." Archives of toxicology, Supplement. Archiv fur Toxikologie. vol. 7, 219-231 (1984).

Ame, J-C. et al., "PARP-2, a novel mammalian DNA damage-dependent poly(ADP-ribose) polymerase," J. Biol. Chem. (1999) 274(25):17860-17868.

Ame, J-C. et al., "The PARP superfamily," Bio Essays (2004) 26:882-893.

Angell, S.M. et al., "Consistent gene silencing in transgenic plants expressing a replicating potato virus X RNA," EMBO J. (1997) 16(12):3675-3684.

Arnaudeau, C. et al., "DNA double-strand breaks associated with replication forks are predominantly repaired by homologous recombination involving an exchange mechanism in mammalian cells," J. Mol. Biol.(2001) 307:1235-1245.

Baker, Handbook of Pharmaceutical Excipients. "Copovidone". Mar. 1, 2012. Pharmaceutical Press and American Pharmacists Association 2012. Accessed Nov. 28, 2012 from http://www.medicinescomplete.com/mc/excipients/current/1001936849.htm?q=copovidone&t=search&ss=text&p=2#_hit.

Banasik, M. et al., "Specific Inhibitors of Poly (ADP-Ribose) Synthetase and Mono (ADP-Ribosyl) transferse", J. Biol. Chem., 1992, vol. 267, 1569-1575.

Banasik, M. et al., "Inhibitors and activators of ADP-ribosylation reactions," Mol. Cell. Biochem.(1994) 138:185-197.

Banker, G.S. et al., Modern Pharmaceutics, Third Edition, Marcel Dekker, Inc., New York, (1996) p. 596.

Ben-Hur, E. et al., "Inhibitors of poly (ADP-ribose) synthesis enhance radiation response by differentially affecting repair of potentially lethal versus sublethal damage," Br. J. Cancer (1984) 49(Supplemental VI):39-42.

Berge et al., 1977, "Pharmaceutical Salts," J. Pharm. Sci., vol. 66, 1-19.

Berger, N.A, "Poly (ADP-ribose) in cellular resposne to DNA damage", Radiation Research, 1985, vol. 101, 4-15.

Bhattacharyya, A. et al., "The breast cancer susceptibility gene BRCA1 is required for subnuclear assembly of Rad51 and survival following treatment with the DNA cross-linking agent cisplatin," J. Biol. Chem. (2000) 275(31):23899-23903.

Bloch, W. et al., "Poly-adenosine diphosphate-ribose polymerase inhibition for myocardial protection: pathophysiologic and physiologic considerations," J. Thoracic Card. Surg. (2004) 128(2):323-324.

Bold, G. et al., "New anilinophthalazines as potent and orally well absorbed inhibitors of the VEGF receptor tyrosine kinases useful as antagonists of tumor-driven angiogenesis," J. Med. Chem. (2000) 43:3200 (Correction).

Bold, G. et al., "New anilinophthalazines as potent and orally well absorbed inhibitors of the FEBF receptor tyrosine kinases useful as antagonists of tumour-driven angiogenesis", J. Med. Chem., 2000, vol. 43, No. 12, 2310-2323.

Bowman et al., "Differential effects of the poly (ADP-ribose) polymerase (PARP) inhibitor NU 1025 on topoisomerase I and II inhibitor cytotoxicity in L1210 cells in vitro," British Journal of Cancer, vol. 84(1), 106-112 (2001).

Braga, D. et al., "Making crystals from crystals: a green route to crystal engineering and polymorphism," Chem. Commun. (2005) 3635-3645.

Brummelkamp, T. R. et al., "A system for stable expression of short interfering RNAs in mammalian cells," Science (2002) 296:550-553.

Bühler, "Polyvinylpyrrolidone Excipients for Pharmaceuticals: Povidone, Crospovidone and Copovidone," 2005 Springer-Verlag; pp. 179-219 (chapter 4) and pp. 83-97 (section 2.4.3 of chapter 2).

Burzio, L. et al., "Poly (adenosine diphosphoribose) synthase activity of isolated nuclei of normal and leukemic leukocytes (38930)", Proc. Soc. Exp. Bio. Med., 1975, vol. 149, 933-938.

Calabrese, C.R. et al., "Identification of potent nontoxic poly(ADP-ribose) polymerase-1 inhibitors: chemopotentiation and pharmacological studies," Clin. Can. Res. (2003) 9:2711-2718.

Caldecott, K.W., "DNA single-strand break repair and spinocerebellar ataxia," Cell (2003) 112:7-10.

Cantoni, O. et al., "Hydrogen peroxide insult in cultured mammalian cells: relationships between DNA single-strand breakage, poly (ADP-ribose) metabolism and cell killing", Biochim. Biophys. Acta, 1989, vol. 1014, 1-7.

CAS Registry No. 763113-22-0 (Oct. 15, 2004).

Catteau, A. et al., "Methylation of the BRCA1 promoter region in sporadic breast and ovarian cancer: correlation with disease characteristics," Oncogene (1999) 18:1957-1965.

Chalmers, A.J. , "Poly(ADP-ribose) polymerase-1 and ionizing radiation: sensor, signaller and therapeutic target," Clin. Onc. (2004) 16:29-39.

Chappuis, P. O. et al., "Risk Assessment and Genetic Testing," Cancer Treat. Res., 2002, vol. 107, 29-59.

Chiarugi, A., "Poly(ADP-ribose) polymerase: killer or conspirator? The 'suicide hypothesis' revisted," Trends in Pharm. Sci. (2002) 23(3):122-129.

Chokshi, "Hot-Melt Extrusion Technique: A Review", Iranian Journal of Pharmaceutical Research (2004); 3; 3-16.

Cockcroft, X-L. et al., "Phthalazinones 2: optimisation and synthesis of novel potent inhibitors of poly(ADP-ribose)polymerase," Biorg. Med. Chem. Lett. (2006) 16:1040-1044.

Cosi, C. et al., "Poly (ADP-ribose) polymerase: early involvement in glutamate-induced neurotoxicity in cultured cerebellar granule cells", J.Neurosci. Res., 1994, vol. 39, 38-46.

Cosi, C., "New inhibitors of poly(ADP-ribose) polymerase and their potential therapeutic targets," Expert Opin. Ther. Patents (2002) 12(7): 1047-1071.

Couzin, J., "The twists and turns in BRCA's path," Science (2003) 302:591-592.

Crooke, S.T., "Therapeutic applications of oligonucleotides," Ann. Rev. Pharmacol. Toxicol. (1992) 32:329-376.

Cuzzocrea, S., "Shock, inflammation and PARP," Pharmacological Res. (2005) 52:72-82.

D'Adda Di Fagagna, F. et al., "Functions of poly(ADP-ribose) polymerase in controlling telomere length and chromosomal stability", Nature Gen., 1999, vol. 23, No. 1, 76-80.

D'Amours, D. et al., "Poly(ADP-ribosyl)ation reactions in the regulation of nuclear functions", Biochem. J., 1999, vol. 342, 249-268.

D'Amours, D. et al., "The MRE11 complex: at the crossroads of DNA repair and checkpoint signalling," Nat. Rev. Mol. Cell Biol. (2002) 3:317-327.

D'Andrea, A. D. et al., "The fanconi anaemia/BRCA pathway," Nat. Rev. Cancer (2003) 3:23-34.

(56) References Cited

OTHER PUBLICATIONS

Dantzer, F. et al., "Base excision repair is imparied in mammalian cells lacking poly(ADP-ribose) polymerase-1," Biochemistry (2000) 39:7559-7569.

Dantzer, F. et al., "Involvement of poly(ADP-ribose) polymerase in base excision repair," Biochimie (1999) 81:69-75.

Davies, A. A. et al., "Role of BRCA2 in control of the RAD51 recombination and DNA repair protein," Mol. Cell (2001) 7:273-282.

Dillon, K. J. et al., "A flashplate assay for the identification of PARP-1 inhibitors," J. Biomolecular Screening (2003) 8(3):347-352.

Durkacz, B. W. et al., "(ADP-ribose)n participates in DNA excision repair", Nature, 1980, vol. 283, No. 7, 593-596.

Dusemund, "Isochino [3,2-a]phthalazin-5,8-dione", Arch. Pharm., (Weinhein) 1982, pp. 925-930. (English Abstract).

Dusemund, J., "Einfache synthese von isochino[2,3-c][2,3]benzoxazepinon und -[2,3]benzodiazepinonen sowie ihrer vorstufen," Arch. Pharm.(Weinhein)(1988) 321:41-44.

Egawa, C. et al., "Decreased expression of BRCA2 mRNA predicts favorable response to docetaxel in breast cancer," Int. J. Cancer (Pred. Oncol.)(2001) 95:255-259.

Egawa, C. et al., "Quantitative analysis of estrogen receptor-α and -β messenger RNA expression in normal and malignant thyroid tissues by real-time polymerase chain reaction," Oncology (2001) 61:293-298.

Ehrlich, H.A. et al., "Recent advances in the polymerase chain reaction," Science (1991) 252:1643-1650.

Elbashir, S. M. et al., "Duplexes of 21-nucleotide RNAs mediate RNA interference in cultured mammalian cells," Nature (2001) 411:494-498.

El-Tamaty et al., "Synthesis and biological activity of some 4-benzyl-1(2H)-phthalazinone derivatives", Indian J. Chemistry, v. 35B, 1067-1072 (1996).

El-Tamaty E.S.H et al, "Synthesis and biological activity of some 4-benzyl-1(2H)-phthalazinone derivatives", Chem.Abs. (1966) 125:23, 125:300924j.

Esteller, M. et al., "Promoter hypermethylation and BRCA1 inactivation in sporadic breast and ovarian tumors," J. Natl. Cancer Inst. (2000) 92(7):564-569.

Ferraris, D. et al., "Design and synthesis of poly ADP-ribose polymerase-1 inhibitors. 2. Biological evaluation of Aza-5[H]-phenanthridin-6-ones as potent, aqueous-soluble compounds for the treatment of ischemic injuries," J. Med. Chem. (2003) 46:3138-3151.

Fire, A. et al., "Potent and specific genetic interference by double-stranded RNA in Caenorhabditis elegans," Nature (1998) 391:806-811.

Foray, N. et al., "A subset of ATM- and ATR-dependent phosphorylation events requires the BRCA1 protein," EMBO J. (2003) 22(11):2860-2871.

Fuska, J. et al., "New Cytotoxic and antitumor agents," Neoplasma (1985), 32(4): 407-414.

Gaken, J. A. et al., "Efficient retroviral infection of mammalian cells is blocked by inhibition of poly(ADP-ribose) polymerase activity", J. Virology, 1996, vol. 70, No. 6, 3992-4000.

Gale, P.A. et al., "Calixpyrroles II," Coordination Chem. Rev. (2001) 222:57-102.

Gavezzotti, A., "Are crystal structures predictable?" Acc. Chem. Res. (1994) 27:309-314.

Greene, T.W. et al., Protective Groups in Organic Synthesis, Chapters 2 and 7, John Wiley & Sons Inc. (1999) p. 17-23 and 494-503.

Griffin et al., "Mammalian recombination-repair genes XRCC2 and XRCC3 promote correct chromosome segregation", Nature Cell Biol (2000) 2:757-761.

Griffin et al., "The role of inhibitors of poly (ADP-ribose) polymerase as resistance-modifying agents in cancer therapy," Biochimie vol. 77, 408-422 (1995).

Grube, K. et al., "Direct stimulation of poly(ADP ribose) polymerase in permeabilized cells by double-stranded DNA oligomers," Anal. Biochem. (1991) 193:236-239.

Haber, J. E., "DNA recombination: the replication connection," Trends Biochem. Sci. (1999) 24:271-275.

Hall, I.H. et al., "Cytotoxicity of imides-N-alkyl semicarbazones, thiosemicarbazones, acetylhydrazones and related derivatives," Anti-Cancer Drugs (and abstract 122:204573), V.6, 147-153 (1995).

Halldorsson, H. et al., "Poly(ADP-ribose) polymerase activity in nucleotide permeable cells," FEBS Lett. (1978) 85(2):349-352.

Hawley's Condensed Chemical Dictionary, 13th ed., Van Nostrand Reinhold eds. 716 and 825 (1997).

Herceg, Z. et al., "Functions of poly(ADP-ribose) polymerase (PARP) in DNA repair, genomic intergrity and cell death," Mut. Res. (2001) 477:97-110.

Hirai, K. et al., "Aberration of poly(adenosine diphosphate-ribose) metabolism in human colon adenomatous polyps and cancers", Cancer Res., 1983, vol. 43, 3441-3446.

Hiramoto, T. et al., "Mutations of a novel human RAD54 homologue, RAD54B, in primary cancer," Oncogene (1999) 18:3422-3426.

Hoeijmakers, J. H.J., "Genome maintenance mechanisms for preventing cancer," Nature (2001) 411:366-374.

Hughes-Davies, L. et al., "EMSY links the BRCA2 pathway to sporadic breast and ovarian cancer," Cell (2003) 115:523-535.

Iino, M. et al., "Rational design and evaluation of new lead compound structures for selective .beta.ARK1 inhibitors," J. Med. Chem. (2002) 45(11):2150-2159.

Islam, A.M. et al., "Thioarylidenephthalides and related compounds: Part II. Reactions with amino compounds," Indian J. Chem. Sect. B: Org. Chem. Inc. Med. Chem. (1977), 15(1): 58-60.

Islam, A.M et al., "4, 5, 6, 7-Tetraiodo-3-benzalphthalides and related compounds," Egyptian J. Chem. (1979), 22(2): 135-141.

Islam, A.M. et al., "Action of phosphorus pentasulfide on the products of interaction of p-sulfamoylphenylacetic acids with phthalic anhydride," Egyptian J. Chem. (1979) 22(3): 209-222.

Jackson, S.P., "Sensing and repairing DNA double-strand breaks," Carcinogenesis (2002) 23(5):687-696.

Janatova, M. et al., "Detection of the most frequent mutations in BRCA1 gene on polyacrylamide gels containing spreadex polymer NAB," Neoplasma (2003) 50(4):246-250.

Jancarkova, N., "Detection and incidence of mutations of BRCA1 gene in patients with cancer of the breast and ovary," Ceska Gynekol. (2003) 68(1):11-16.

Jantzen and Robinson, "B. Prodrugs," taken Modern Pharmaceutics, Third Edition, Banker and Rhodes, editors (1996) p. 596.

Jasin, M., "Homologous repair of DNA damage and tumorigenesis: the BRCA connection," Oncogene (2002) 21(58):8981-8993.

Jijon, H.B. et al., "Inhibition of poly(ADP-ribose) polymerase attenuates inflammation in a model of chronic colitis," Am. J. Physiol. Gastrointest. Liver Physiol. (2000) 279:G641-G651.

Johnson, R.D. et al., "Mammalian XRCC2 promotes the repair of DNA double-strand breaks by homologous recombination," Nature (1999) 401:397-399.

Kanaar, R. et al., "Molecular mechanisms of DNA double-strand break repair," Trends Cell Biol. (1998) 8:483-489.

Kashani-Sabet, M. et al., "Application of ribozymes to cancer gene therapy," Cancer Gene Therapy (1995) 2(3):213-223.

Kawamura, I. et al., "Ponalrestat, an aldose reductase inhibitor," Anticancer Res. (1999), 19(5B): 4105-4111.

Kerr, P. et al., "New complexities for BRCA1 and BRCA2," Curr. Biol. (2001) 11:R668-676.

Kerrigan, F. et al. "Imide-substituted 4-benzyl-2H-phthalazin-1-ones: potent inhibitors of poly(ADP-ribose) polymerase-1 (PARP-1)," Poster at 12th SCI-RSC Medicinal Chemistry Symposium, Cambridge, (2003).

Khanna, K. K. et al., "DNA double-strand breaks: signaling, repair and the cancer connection," Nat. Genet. (2001) 27(3):247-254.

Kraakman-Van Der Zwet, M. et al., "Brca2 (XRCC11) deficiency results in radioresistant DNA synthesis and a higher frequency of spontaneous deletions," Mol. Cell Biol. (2002) 22(2):669-679.

Kuperstein, G. et al., "A rapid fluorescent multiplexed-PCR analysis (FMPA) for founder mutations in the BRCA1 and BRCA2 genes," Clin. Genet. (2000) 57:213-220.

(56) References Cited

OTHER PUBLICATIONS

Kupper, J-H. et al., "Trans-dominant inhibition of poly(ADP-ribosyl)ation potentiates carcinogen-induced gene amplification in SV40-transformed Chinese hamster cells," Cancer Res. (1996) 56:2715-2717.

Lakhani, S. R. et al., "The pathology of familial breast cancer: predictive value of immunohistochemical markers estrogen receptor, progesterone receptor, HER-2, and p53 in patients with mutations in BRCA1 and BRCA2," J. Clin. Oncol. (2002) 20(9):2310-2318.

Le Rhun, Y. et al., "Cellular responses to DNA damage in the absence of poly(ADP-ribose)polymerase", Biochem. Biophys. Res. Commun., 1998, vol. 245, 1-10.

Lemay, M. et al., "Detection of DNA damage and identification of UV-induced photoproducts using the CometAssay kit," Bio Techniques (1999) 27:846-851.

Leuner et al. Improving drug solubility for oral delivery using solid dispersions. Eur J Pharm Biopharm. Jul. 2000;50(1 ):47-60).

Liaudet, L. et al., "Protection against hemorrhagic shock in mice genetically deficient in poly(ADP-ribose)polymerase", Proc. Natl. Acad. Sci. U.S.A., 2000, vol. 97, No. 18, 10203-10208.

Lindahl, T. et al, "Quality control by DNA repair," Science (1999) 286:1897-1905.

Lindahl, T. et al, "Post-translational modification of poly(ADP-ribose) polymerase induced by DNA strand breaks," Trends Biochem. Sci. (1995) 20:405-411.

Loh, V.M. et al., "Phthalazinones. Part 1: The design and synthesis of a novel series of potent inhibitors of poly(ADP-ribose)polymerase," Bioorg. Med. Chem. Lett. (2005) 15:2235-2238.

Lundin, C. et al., "Different roles for nonhomologous end joining and homologous recombination following replication arrest in mammalian cells," Mol. Cell. Biol. (2002) 22(16):5869-5878.

Lundin, C et al., "RAD51 is involved in repair of damage associated with DNA replication in mammalian cells," J. Mol. Biol. (2003) 328:521-535.

Magnusson, J et al., "Inhibitor of poly(ADP-ribose)transferase potentiates that recombinogenic but not the mutagenic action of alkylating agents in somatic cells in vivo in *Drosophila melangaster*," Mutagenesis (1990) 5(5): 511-514.

Martin, N. et al., "Phthalazinone derivatives as potent PARP-1 inhibitors", 13th Intl. Symposium on ADP-ribosylation, 2001, Abstract 107.

Martin, N., "DNA repair inhibition and cancer therapy," J. Photochem. and PhotoBiol. B: Biology (2001) 63:162-170.

Matsuda, M. et al., "Mutations in the RAD54 recombination gene in primary cancers," Oncogene(1999) 18:3427-3430.

McMahon, G., "VEGF receptor signaling in tumor angiogenesis," The Oncologist (2000) 5(suppl 1):3-10.

McNealy, T. et al., "Intrinsic presence of poly (ADP-ribose) is significantly increased in malignant prostate compared to benign prostate cell lines," Anticancer Res. (2003) 23:1473-1478.

Menear, K.A. et al., "4-[3-(4-cyclopropanecarbonylpiperazine-1-carbonyl)-4-fluorobenzyl]-2H-phthalazin-1-one: a novel bioavailable inhibitor of poly(ADP-ribose) polymerase-1," J. Med. Chem. (2008)51 (20)i 6581-6591.

Menissier De Murcia, J. et al., "Requirement of poly(ADP-ribose)polymerase in recovery from DNA damage in mice and cells," Proc. Natl. Acad. Sci. U.S.A., 1997, vol. 94, 7303-7307.

Menissier De Murcia, J. et al., "Functional interaction between PARP-1 and PARP-2 in chromosome stability and embryonic development in mouse," EMBO J. (2003) 22(9):2255-2263.

Mercola, D. et al., "Antisense approaches to cancer gene therapy," Cancer Gene Therapy (1995) 2(1):47-59.

Miller, B.A., "Inhibition of TRPM2 function by PARP inhibitors protects cells from oxidative stress-induced death," Br. J. Pharmacology (2004) 143:515-516.

Miwa, M. et al., "Cell density-dependent increase in chromatin-associated ADP-ribosyltransferase activity in simian virus 40-transformed cells", Arch. Biochem. Biophys., 1977, vol. 181, 313-321.

Molife, Rhoda et al., 'A Phase I Study to Determine the Comparative Bioavailability of Two Different Oral Formulations of the PARP Inhibitor, Olaparib (AZD2281), in Patients with Advanced Solid Tumors', American Society of Clinical Oncology Meeting: Chicago, IL, Jun. 7, 2010.

Molife, Rhoda et al., 'A Phase I Study to Determine the Comparative Bioavailability of Two Different Oral Formulations of the PARP Inhibitor, Olaparib (AZD2281), in Patients with Advanced Solid Tumors', American Society of Clinical Oncology Meeting: Chicago, IL, Jun. 7, 2010; poster.

Morrison, C. et al., "Genetic interaction between PARP and DNA-PK in V(D)J recombination and tumorigenesis," Nature Genetics (1997) 17:479-482.

Moynahan, M. E. et al., "Brca1 controls homology-directed DNA repair," Mol. Cell (1999) 4:511-518.

Moynahan, M. E. et al., "BRCA2 is required for homology-directed repair or chromosomal breaks," Mol. Cell (2001) 7:263-272.

Mullis, K. et al., "Specific enzymatic amplification of DNA in vitro: the polymerase chain reaction," Cold Spring Harbor Symp. Quant. Biol. (1986) vol. 51 (Part 1):263-273.

Nakamura, J. et al., "Quantitation of intracellular NAD(P)H can monitor an imbalance of DNA single strand break repair in base excision repair deficient cells in real time," Nuc. Acids Res. (2003) 31(17):e104 1-7.

Nathanson, K. L. et al., "Breast cancer genetics: what we know and what we need," Nat. Med. (2001) 7(5):552-556.

Neuhausen, S. L. et al., "Mutation testing of early-onset breast cancer genes BRCA1 and BRCA2," Genet. Test (1997) 1(2):75-83.

Noel, G. et al., "Poly(ADP-ribse) polymerase (PARP-1) is not involved in DNA double-strand break recovery," BMC Cell Biol. (2003) 4:7-17.

Pacher et al., "The Role of Poly(ADP-Ribose) Polymerase Activation in the Development of Myocardial and Endothelial Dysfunction in Diabetes," Diabetes, 51:514-521 (2002).

Perkins, E. et al., "Novel inhibitors of poly(ADP-ribose)polymerase/PARP1 and PARP2 identified using a cell-based screen in yeast", Cancer Res., vol. 61, 4175-4183 (2001).

Pierce, A.J. et al., "XRCC3 promotes homology-directed repair of DNA damage in mammalian cells," Genes & Dev. (1999) 13:2633-2638.

Pinedo et al., "Translation Research: The Role of VEGF in Tumor Anglogenesis" The Oncologist (2000) 5(suppl 1):1-2.

Radice, P. J., "Mutations of BRCA genes in hereditary breast and ovarian cancer,." Exp. Clin. Cancer Res. (2002) 21(3 Suppl.):9-12.

Rattan, S. I. et al., "Kinetin delays the onset of ageing characteristics in human fibroblasts", Biochem. Biophys. Res. Commun., 1994, vol. 201, No. 2, 665-672.

Remington: The Science and Practice of Pharmacy (21st Edition) 2005, p. 893.

Said, S. I. et al., "Excitotoxicity in the lung: N-methy-D-aspartate-induced, nitric oxide-dependent, pulmonary edema is attenuated by vasoactive intestinal peptide and by inhibitors of poly(ADP-ribose)polymerase", Proc. Natl. Acad. Sci. U.S.A., 1996, vol. 93, 4688-4692.

Samper, E. et al., "Normal telomere length and chromosomal end capping in poly(ADP-ribose) polymerase-deficient mice and primary cells despite increased chromosomal instability," J. Cell Biol. (2001) 154(1):49-60.

Satoh, M.S. et al., "Role of poly(ADP-ribose) formation in DNA repair," Nature (1992) 356:356-358.

Schlicker, A. et al., "4-Amino-1,8-napthalimide: a novel inhibitor of poly(ADP-ribose)polymerase and radiation sensitizer", Int. J. Radiat. Bio., 1999, vol. 75, No. 1, 91-100.

Schreiber, V. et al., "A dominant-negative mutant of human poly(ADP-ribose) polymerase affects cell recovery, apoptosis, and sister chromatid exchange following DNA damage," Proc. Natl. Acad. Sci. USA (1995) 92:4753-4757.

Schreiber, V. et al., "Poly(ADP-ribose) polymerase-2 (PARP-2) is required for efficient base excision DNA repair in association with PARP-1 and XRCC1," J. Biol. Chem. (2002) 277(25):23028-23036.

Schultz, N. et al., "Poly(ADP-ribose) polymerase (PARP-1) has a controlling role in homologous recombination," Nucleic Acids Res. (2003) 31:4959-4964.

(56) References Cited

OTHER PUBLICATIONS

Semionov, A. et al., "Inhibition of poly(ADP-ribose)polymerase stimulates extrachromosomal homologous recombination in mouse Ltk-fibroblasts," Nuc. Acids Res. (1999) 27(22):4526-4531.

Shah, G.M. et al., "Complete inhibition of poly(ADP-ribose) polymerase activity prevents the recovery of C3H10T1/2 cells from oxidative stress," Biochimica et Biophysica Acta (1996) 1312:1-7.

Shall, S. et al., "Poly(ADP-ribose) polymerase-1: what have we learned from the deficient mouse model?" Mutat. Res. (2000) 460:1-15.

Shimizu, T. et al., "Inhibitory effects of azelastine and tranilast on leukotriene B4 and leukotriene C4 generation by rat colonic mucosa", Prostaglandins Leukotrienes and Essential Fatty Acids, 1995, vol. 53, 355-358.

Silverman, R.B., The Organic Chemistry of Drug Design and Drug Action, 352-400 (1992) Academic Press, Inc., 352-400.

Simbulan-Rosenthal, C.M. et al., "Chromosomal aberrations in PARP-/-#mice: genome stabilization in immortalized cells by reintroduction of poly(ADP-ribose) polymerase cDNA," Proc. Natl. Acad. Sci. USA (1999) 96(23):13191-13196.

Skehan, P. et al., "New colorimetric cytotoxicity assay for anticancer-drug screening", J. Natl. Cancer Inst., 1990, vol. 82, No. 13, 1107-1112.

Southan, G.J. and Szabo, C., "Poly (ADP-ribose) polymerase inhibitors," Current Medicinal Chemistry, 10(4):321-340 (2003).

Spears, L.G. Jr. et al., "Anionic phosphorous as a nucleophile. An anion chain Arbuzov mechanism," J. Org. Chem. (1987) 52:61-64.

Suto, M.J. et al., "Dihydroisoquinolinones: the design and synthesis of a new series of potent inhibitors of poly(ADP-ribose) polymerase," Anticancer Drug Des. (1991) 7:107-117.

Szabo, C. et al., "Endothelial dysfunction in a rat model of endotoxic shock", J. Clin. Invest., 1997, vol. 100, 723-25.

Szabo, "Role of Poly (ADP-Ribose) Polymerase Activation in the Pathogenesis of Shock and Inflammation" in PARP as a Therapeutic Target, Zhang, Ed. CRC Press (2002) 169-204.

Szabo, G. et al., "Poly-ADP-ribose polymerase inhibition protects against myocardial and endothelial reperfusion injury after hypothermic cardiac arrest," J. Thoracic Cardiovas. Surg. (2003) 126(3):651-658.

Taniguchi, T. et al., "Disruption of the Fanconi anemia-BRCA pathway in cisplatin-sensitive ovarian tumors," Nat. Med. (2003) 9(5):568-574.

Tarsounas, M. et al., "BRCA2-dependent and independent formation of RAD51 nuclear foci," Oncogene (2003) 22:1115-1123.

Tasatargil, A. et al., "Poly(ADP-ribose) polymerase inhibition prevents homocysteine-induced endothelial dysfunction in the isolated rat aorta," Pharmacology (2004) 72:99-105.

Tebbs, R.S. et al., "Correction of chromosomal instability and sensitivity to diverse mutagens by a cloned cDNA of the XRCC3 Dna repair gene," Proc. Natl. Acad. Sci. USA (1995) 92:6354-6358.

Tentori, L. et al., "Potential clinical applications of poly(ADP-ribose) polymerase (PARP) inhibitors," Pharm. Res. (2002) 45(2):73-85.

Thompson, L. H. et al., "Recombinational DNA repair and human disease," Mutat. Res. (2002) 509:49-78.

Tracey, W. et al., "Aldose reductase inhibition alone or combined with an adenosine A3 agonist reduces ischemic myocardial injury," Am. J. Physiol. Heart Circ. Physiol. (2001) 279: H1447-H1452.

Tutt, A. et al., "The relationship between the roles of BRCA genes in DNA repair and cancer predisposition," Trends Mol. Med. (2002) 8(12):571-576.

Tutt, A. et al., "Mutation in Brca2 stimulates error-prone homology-directed repair of DNA double-strand breaks occurring between repeated sequences," EMBO J. (2001) 20(17):4704-4716.

Tutt, A N.J. et al., "Disruption of Brca2 increases the spontaneous mutation rate in vivo: synergism with ionizing radiation," EMBO Reports (2002) 3(3):255-260.

Uhlmann, E. et al., "Antisense oligonucleotides: a new therapeutic principle," Chem. Rev. (1990) 90(4):543-584.

United States Office Action for U.S. Appl. No. 10/021,506 dated Nov. 26, 2003 (5 pages).

United States Office Action for U.S. Appl. No. 10/021,506 dated Sep. 7, 2004 (7 pages).

United States Office Action for U.S. Appl. No. 10/021,506 dated Jun. 15, 2005 (5 pages).

United States Office Action for U.S. Appl. No. 10/021,506 dated Nov. 21, 2005 (8 pages).

United States Office Action for U.S. Appl. No. 11/352,178 dated Nov. 7, 2008 (11 pages).

United States Office Action for U.S. Appl. No. 10/426,147 dated Oct. 28, 2004 (32 pages).

United States Office Action for U.S. Appl. No. 10/426,147 dated Aug. 9, 2005 (16 pages).

United States Office Action for U.S. Appl. No. 10/426,147 dated Apr. 25, 2006 (14 pages).

United States Office Action for U.S. Appl. No. 11/873,671 dated Sep. 3, 2008 (35 pages).

United States Office Action for U.S. Appl. No. 11/873,671 dated Mar. 6, 2009 (12 pages).

United States Office Action for U.S. Appl. No. 12/143,208 dated May 8, 2009 (15 pages).

United States Office Action for U.S. Appl. No. 10/876,080 dated Jun. 23, 2005 (4 pages).

United States Office Action for U.S. Appl. No. 10/876,080 dated Jul. 12, 2006 (5 pages).

United States Office Action for U.S. Appl. No. 10/876,080 dated Jan. 5, 2007 (5 pages).

United States Office Action for U.S. Appl. No. 10/876,080 dated Oct. 4, 2007 (6 pages).

United States Office Action for U.S. Appl. No. 11/318,155 dated Jul. 11, 2008 (10 pages).

United States Office Action for U.S. Appl. No. 11/318,155 dated Jan. 26, 2009 (9 pages).

Van Gent, D.C. et al., "Chromosomal stability and the DNA double-stranded break connection," Nature Reviews Genetics (2001) 2:196-206.

Venkitaraman, A. R., "Cancer susceptibility and the functions of BRCA1 and BRCA2," Cell (2002) 108:171-182.

Vippagunta, S.R. et al., "Crystalline solids," Adv. Drug Delivery Reviews (2001) 48:3-26.

Virag and Szabo, "The Therapeutic Potential of Poly(ADP-Ribose) Polymerase Inhibitors," Pharmacological Reviews, vol. 54(3), (2002) 375-429.

Voinnet, O. et al. "Systemic signalling in gene silencing," Nature (1997) 389:553.

Waldman, A.S. et al., "Stimulation of intrachromosomal homologous recombination in mammalian cells by an inhibitor of poly(ADP-ribosylation)," Nuc. Acids Res. (1991) 19(21):5943-5947.

Wang, Z.-Q. et al., "Mice lacking ADPRT and poly(ADP-ribosyl)ation develop normally but are susceptible to skin disease", Genes Dev., 1995, vol. 9: 509-520.

Wang, Z.-Q. et al., "PARP is important for genomic stability but dispensable in apoptosis," Genes Dev. (1997) 11:2347-2358.

West, A.R. "Solid State Chemistry and Its Applications" Wiley, New York, (1988): 358, 365.

Wolff, M.E., Burger's Medicinal Chemistry and Drug Discovery, Fifth Edition, vol. 1: Principles and Practice, John Wiley & Sons, Inc., New York (1995) 975-977.

Wood, R.D. et al., "Human DNA repair genes," Science (2001) 291:1284-1289.

Yamaguchi, M. et al., "Novel antiasthmatic agents with dual activities of thromboxane A2 synthetase inhibition and bronchodilation. 1. 2-[2-(1-Imidazolyl)alkyl]-1 (2H)-phthalazinones", J. Med. Chem., 1993, vol. 36, No. 25, 4052-4060.

Yamaguchi, M. et al., "Novel antiasthmatic agents with dual activities of thromboxane A2 synthetase inhibition and bronchodilation. 2. 4-(3-Pyridyl)-1 (2H)-phthalazinones", J. Med. Chem., 1993, vol. 36, No. 25, 4061-4068.

Yap et al. First in human phase I pharmacokinetic (PK) and pharmacodynamic (PO) study of KU-0059436 (Ku), a small molecule inhibitor of poly ADP-ribose polymerase (PARP) in cancer

(56) References Cited

OTHER PUBLICATIONS patients . . . . Journal of Clinical Oncology, 2007 ASCO Annual Meeting Proceedings Part I. vol. 25, No. 18S (Jun. 20 Supplement), 2007: 3529.

Zamore, P. D., "RNAi: double-stranded RNA directs the ATP-dependent cleavage of mRNA at 21 to 23 nucleotide intervals," Cell (2000) 101:25-33.

Zamore, P. D., "RNA interference: listening to the sound of silence," Nature Structural Biology (2001) 8(9):746-750.

Zhang, J. et al., "Neuroprotective effects of poly(ADP-ribose) polymerase inhibition on focal cerebral ischemia," Portland Press Proc. (1998) 15 (Biology of Nitric Oxide, Part 6):125.

Zhang, W. et al., "Fluorous 2,4-dichloro-1,3,5-triazine (F-DCT) as amide coupling agent," QSAR Comb Sci. (2006) 25(8-9):724-727.

Zhong, Q. et al., "Association of BRCA1 with the hRad50-hMre11-p95 complex and the DNA damage response," Science (1999) 285:747-750.

Zingarelli, B. et al., "Activator protein-1 signalling pathway and apoptosis are modulated by poly(ADP-ribose) polymerase-1 in experimental colitis," Immunology (2004) 113:509-517.

Remington, Joseph Price, Remington: The Science and Practice of Pharmacy, Eds. David B. Troy, and Paul Beringer, Lippincott Williams & Wilkins, (2006), pp. 108, 371, 891-893.

Rowe, Raymond C., Sheskey, Paul J., and Owen, Sian C., Handbook of Pharmaceutical Excipients:Colloidal Silicon Dioxide, London, Pharmaceutical Press, (2006) (6)188-191.

Serajuddin, Abu T.M., "Solid dispersion of poorly water-soluble drugs: Early promises, subsequent problems, and recent breakthroughs", Journal of Pharmaceutical Sciences, vol. 88, Issue 10, 1999.

Copending U.S. Appl. No. 18/312,333, filed May 4, 2023.

\* cited by examiner

Key:

----- Correlation square for cross peak at 1050 cm⁻¹, 1650 cm⁻¹

——— Correlation square for cross peak at 1050 cm⁻¹, 2700 cm⁻¹

| Polymer | Solvent System | Drug Loading (%w/w) | Additive (%w/w) |
|---|---|---|---|
| PEG 6000 | | | |
| Poloxamer F68 | DCM / MeOH (1:1)[a] | 25 | None[b] |
| Poloxamer F127 | | | |
| PVP K25 | | | |
| PVP K30 | Acetone/MeOH (1:4)[b] | 50 | SLS (5) |
| HPMC 606 | | | |
| HPMC Phthalate | | 33 | Tween 80 (5) |
| Eudragit L100-55 | | | |
| Eudragit E100 | | | |
| Kleptose | | | Docusate Na |
| HPC | | | |
| Copovidone | | | |
| Polyacrylic acid | | | |
| Kleptose / PVP K25[c] | | | |
| Kleptose / HPMC606[d] | | | |

Fig. 31

IMMEDIATE RELEASE PHARMACEUTICAL FORMULATION OF 4-[3-(4-CYCLOPROPANECARBONYL-PIPERAZINE-1-CARBONYL)-4-FLUORO-BENZYL]-2H-PHTHALAZIN-1-ONE

This application is a continuation of U.S. application Ser. No. 18/755,544, filed Jun. 26, 2024, which is a continuation of U.S. application Ser. No. 18/312,375, filed May 4, 2023, which is a continuation of U.S. application Ser. No. 17/483,070, filed Sep. 23, 2021, now abandoned, which is a continuation of U.S. application Ser. No. 16/863,074, filed Apr. 30, 2020, now abandoned, which is a continuation of U.S. application Ser. No. 16/224,096, filed Dec. 18, 2018, now abandoned, which is a continuation of U.S. application Ser. No. 15/707,376, filed Sep. 18, 2017, now abandoned, which is a continuation of U.S. application Ser. No. 15/449,353, filed Mar. 3, 2017, now abandoned, which is a continuation of U.S. application Ser. No. 14/688,326, filed Apr. 16, 2015, now abandoned, which is a continuation of U.S. application Ser. No. 13/911,151, filed Jun. 6, 2013, now abandoned, which is a continuation of U.S. application Ser. No. 12/574,801, filed Oct. 7, 2009, now U.S. Pat. No. 8,475,842, issued Jul. 2, 2013, which claims the benefit under 35 U.S.C. § 119(e) of U.S. Application No. 61/103,347, filed on Oct. 7, 2008.

Certain embodiments of the invention disclosed herein were made under a joint Research Agreement between Abbott GMBH & Co. KG and AstraZeneca UK Ltd.

The present invention relates to novel pharmaceutical compositions with improved bioavailability and/or stability and/or drug loading, to processes for preparing these novel pharmaceutical compositions and to their use in treating cancer, either as a sole agent or in combination with other therapies.

In particular, the present invention relates to a pharmaceutical formulation comprising 4-[3-(4-cyclopropanecarbonyl-piperazine-1-carbonyl)-4-fluoro-benzyl]-2H-phthalazin-1-one in a solid dispersion with a matrix polymer that exhibits low hygroscopicity and high softening temperature. A particularly suitable matrix polymer being copovidone. The invention also relates to a daily pharmaceutical dose of 4-[3-(4-cyclopropanecarbonyl-piperazine-1-carbonyl)-4-fluoro-benzyl]-2H-phthalazin-1-one provided by such a formulation. In addition, the invention relates to the use of copovidone in a solid dispersion composition with 4-[3-(4-cyclopropanecarbonyl-piperazine-1-carbonyl)-4-fluoro-benzyl]-2H-phthalazin-1-one for increasing the bioavailability and/or stability of the 4-[3-(4-cyclopropanecarbonyl-piperazine-1-carbonyl)-4-fluoro-benzyl]-2H-phthalazin-1-one, or for treating cancer in a patient.

4-[3-(4-cyclopropanecarbonyl-piperazine-1-carbonyl)-4-fluoro-benzyl]-2H-phthalazin-1-one (Compound 1), which has the following structure:

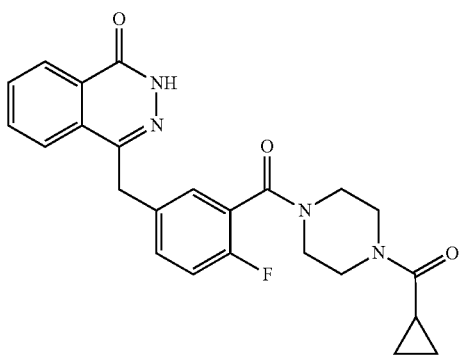 [SMILES: O=C(c1cc(Cc2n[nH]c(=O)c3ccccc23)ccc1F)N1CCN(C(=O)C2CC2)CC1]

is disclosed and exemplified in International Patent Application Publication No. WO 2004/080976, (compound 168). It is a poly(ADP-ribose)polymerase (PARP) inhibitor currently in clinical trials for treating cancers, such as breast and ovarian cancer.

According to WO2005/012524 and WO2005/053662, PARP inhibitor compounds, such as 4-[3-(4-cyclopropanecarbonyl-piperazine-1-carbonyl)-4-fluoro-benzyl]-2H-phthalazin-1-one, are particularly effective in treating cancers whose cells are defective in homologous recombination (HR) dependent DNA double-stranded break (DSB) repair pathway. BRCA1 (NM_007295) and BRCA 2 (NM_000059) hereditary breast/ovarian cancer genes are just 2 out of many proteins in the HR dependent DNA DSB repair pathway. Other members of the HR dependent DNA DSB repair pathway include: ATM (NM_000051), ATR (NM_001184), DSS1 (U41515), RPA 1 (NM_002945.2), RPA 2 (NM_00294.6), RPA 3 (NM_002974.3), RPA 4 (NM_013347.1), Chk1 (NM_001274.2), Chk2 (096017 GI:6685284), RAD51 (NM_002875), RAD51L1 (NM_002877), RAD51c (NM_002876), RAD51L3 (NM_002878), DMC1 (NM_007068), XRCC2 (NM_005431), XRCC3 (NM_05432), RAD52 (NM_002879), RAD54L (NM_003579), RAD54B (NM_012415), RAD50 (NM_005732), MRE11A (NM_005590) and NBS1 (NM_002485). Thus, for example, breast or ovarian cancers that are BRCA1+ and/or BRCA2+ could be much more susceptible to treatment with a PARP inhibitor compound, than cancers without a defective homologous recombination (HR) dependent DNA double-stranded break (DSB) repair pathway; potentially allowing effective monotherapy treatment, and/or treatment at lower doses with concomitant fewer or lesser side effects.

4-[3-(4-cyclopropanecarbonyl-piperazine-1-carbonyl)-4-fluoro-benzyl]-2H-phthalazin-1-one (Compound 1) is a weakly acidic compound with a pKa of about 12.5 (phthalazinone moiety). It is essentially neutral across the physiological pH range. The aqueous equilibrium solubility of Compound 1 was measured to be around 0.10 mg/mL across a range of aqueous buffers (pH 1-9); this solubility is increased to 0.12-0.20 mg/mL in real and simulated gastrointestinal media with the highest solubility of 0.20 mg/mL in the fed state simulated intestinal fluid (see Example 1.1).

Compound 1 was determined to be moderately permeable, compared to the high permeability marker propranolol, when investigated using a Caco-2 cell line. The Caco-2 Papp value was $3.67 \times 10^{-6}$ cm/sec, which equates to a human Peff value of $1.4 \times 10^{-4}$ cm/sec. Compound 1 is at the limits of poorly soluble in terms of drug formulation being a tentative class 4 (at doses above 25 mg) within the Biopharmaceutical Classification System (BCS) based on these solubility and permeability values (see Example 1).

Predictions of the bioavailability of Compound 1, made based on solubility and permeability measurements, suggested that an immediate release (IR) tablet would be suitable for Compound 1. Indeed, compounds with similar solubility, permeability and dose range have been successfully formulated as IR tablets (E.g. see Kasim et al. "Molecular properties of WHO essential drugs and provision of biopharmaceutics classification." Molecular Pharmaceutics. 1(1):85-96, 2004). When tested in dogs however, the exposure following administration of a conventional IR tablet was much lower than expected (see Example 6; FIG. 13).

The oral bioavailability of 4-[3-(4-cyclopropanecarbonyl-piperazine-1-carbonyl)-4-fluoro-benzyl]-2H-phthalazin-1-one to a patient is dependant to a certain extent upon the dissolution rate and solubility of the drug in the GI tract. The bioavailability of 4-[3-(4-cyclopropanecarbonyl-piperazine-1-carbonyl)-4-fluoro-benzyl]-2H-phthalazin-1-one for a series of formulations can be assessed by determining the area under the curve (AUC) of a graph of plasma 4-[3-(4-cyclopropanecarbonyl-piperazine-1-carbonyl)-4-fluoro-benzyl]-2H-phthalazin-1-one concentration v. time elapsed since administration of the 4-[3-(4-cyclopropanecarbonyl-piperazine-1-carbonyl)-4-fluoro-benzyl]-2H-phthalazin-1-one.

The inventors were able to address the poor bioavailability of an IR tablet of Compound 1 by making a lipidic formulation (Gelucire™ 44-14), and this formulation has been used in Phase I and II clinical trials. However, at high drug loading (>10%), reduced exposure was seen with the lipidic formulation (see Example 6 and FIG. 30). A potential issue with the gelucire lipidic formulation was thus only realised during dose escalation studies aimed at determining the maximum tolerated dose and, thus predicting the potential therapeutic dose. It was realized that if the therapeutic dose was 400 mg, a 10% drug loaded Gelucire™ 44-14 formulation would have to be administered as 16 size 0 capsules. Not only does this present with patient compliance issues, it would also have commercial implications, e.g. increase in manufacturing, packaging, and transportation costs, etc.

In the event that 4-[3-(4-cyclopropanecarbonyl-piperazine-1-carbonyl)-4-fluoro-benzyl]-2H-phthalazin-1-one is required in daily dosages greater than 50 mg or 100 mg, (indeed dosages as high as 400 mg twice daily are being tested in clinical trials), it would be desirable to to find a formulation of 4-[3-(4-cyclopropanecarbonyl-piperazine-1-carbonyl)-4-fluoro-benzyl]-2h-phthalazin-1-one with increased bioavailability and one that would allow a sufficient drug loading to be achieved so that it could be administered by means of a manageable number of units (e.g. fewer than 4 per day).

Such increased bioavailability could be useful in enabling a reduction in the daily dose of 4-[3-(4-cyclopropanecarbonyl-piperazine-1-carbonyl)-4-fluoro-benzyl]-2H-phthalazin-1-one required to achieve comparable biological exposure seen with a conventional formulation, e.g. a conventional IR tablet of 4-[3-(4-cyclopropanecarbonyl-piperazine-1-carbonyl)-4-fluoro-benzyl]-2H-phthalazin-1-one.

There is a desire, therefore, to find a formulation of 4-[3-(4-cyclopropanecarbonyl-piperazine-1-carbonyl)-4-fluoro-benzyl]-2H-phthalazin-1-one with improved bioavailability and drug loading relative to a conventional IR tablet formulation, ideally a formulation with a target bioavailability of around 90% (relative to an intravenous solution), and a formulation that permits sufficient drug loading to reduce the number of units that need to be taken at any one time, for example fewer than 4 and ideally to one or two units.

The present invention aims to provide a formulation of 4-[3-(4-cyclopropanecarbonyl-piperazine-1-carbonyl)-4-fluoro-benzyl]-2H-phthalazin-1-one that minimises the size and/or number of tablets or capsules required for the therapeutically effective dose, ideally to fewer than 4 units, preferably only one or two units.

In terms of the aim of increasing the therapeutic potential of 4-[3-(4-cyclopropanecarbonyl-piperazine-1-carbonyl)-4-fluoro-benzyl]-2H-phthalazin-1-one, the inventors sought to increase the therapeutic potential by achieving an increase in the bioavailability of 4-[3-(4-cyclopropanecarbonyl-piperazine-1-carbonyl)-4-fluoro-benzyl]-2H-phthalazin-1-one in a formulation that permitted sufficient high drug loading (e.g. greater than 10%). In distinct embodiments the drug loading will be at least 15%, 20%, 25%, 30%, 35%, 40%, 45%, 50%, 55% or 60%. It will be appreciated that the greater the drug loading the greater the likelihood of instability, so although it may be feasible to generate a formulation with a 60% drug loading it may be preferable to adopt a lower drug loading so as to maintain stability.

Of the various formulation approaches available, the inventors discovered that solid dispersion formulations with particular types of polymer were a means of addressing one or more of the aims stated above. Furthermore, it was surprisingly found that the solid dispersion formulations of the invention increased the bioavailability of Compound 1 compared to the lipidic gelucire formulation.

The inventors have now surprisingly found that the therapeutic potential of 4-[3-(4-cyclopropanecarbonyl-piperazine-1-carbonyl)-4-fluoro-benzyl]-2H-phthalazin-1-one can be increased by formulating 4-[3-(4-cyclopropanecarbonyl-piperazine-1-carbonyl)-4-fluoro-benzyl]-2H-phthalazin-1-one in a solid dispersion with a matrix polymer that exhibits low hygroscopicity and high softening temperature. The matrix polymer copovidone was found to be particularly suitable as it could be used in hot melt extrusion without the need of a plasticiser and it provides a product with acceptable stability, even at 30% drug loading in the final product (e.g. tablet).

It would be further desirable to identify a suitable matrix polymer that could be formulated into a solid dispersion with the drug using any of the available solid dispersion techniques without the need for additional surfactants/plasticisers as it would be appreciated that the presence of certain extraneous excipients could compromise the stability Compound 1 (e.g. the ability to remain in amorphous form).

Thus, in one embodiment the solid dispersion formulation of the invention does not comprise a surfactant/plasticiser.

According to a first aspect of the invention there is provided a pharmaceutical formulation comprising an active agent in solid dispersion with a matrix polymer, wherein the active agent is 4-[3-(4-cyclopropanecarbonyl-piperazine-1-carbonyl)-4-fluoro-benzyl]-2H-phthalazin-1-one or a salt or solvate thereof, and the matrix polymer exhibits low hygroscopicity and high softening temperature.

In one embodiment the active agent is present in the formulation in stable amorphous form. Where the active agent is present in the formulation in stable amorphous form, the formulation may stabilise the active agent in the formulation in the amorphous form and may reduce conversion or reversion to other forms.

In certain embodiments it will be desirable for the salt or solvate of Compound 1 to be a pharmaceutically acceptable salt or solvate.

As used herein, by 'polymer' we mean a macromolecule composed of repeating structural units connected by covalent chemical bonds. The term encompasses linear and branched polymers, cyclic polymers such as cyclic oligosaccharides (including cyclodextrins), homopolymers and copolymers, whether natural, synthetic or semi-synthetic in origin.

As used herein, the term 'matrix polymer' means a material that exhibits low hygroscopicity and high softening temperature comprising a polymer or a blend of two or more polymers.

As used herein, by "low hygroscopicity" we mean having an equilibrium water content <10% at 50% relative humidity, as determined by Dynamic Vapour Sorption (DVS), disclosed in Bergren, M. S. Int. J. Pharm 103:103-114 (1994).

As used herein, by "high softening temperature" we mean that the material, in "as received" form (that is to say, without having been exposed to high humidity) exhibits a glass transition temperature (Tg) or melting point (Tm) >100° C., as determined by Differential Scanning Calorimetry (DSC). The person of ordinary skill in the art will appreciate that Tg is a measurement appropriate for polymers that are in an amorphous state or form and Tm is a measurement that is appropriate for polymers that are in a crystalline state or form.

Suitable matrix polymers for use in the invention include: copovidone, hypromellose phthalate (hydroxypropylmethylcellulose phthalate, HPMCP), hypromellose acetate succinate (hydroxypropylmethylcellulose acetate succinate, HPMCAS), -2-hydroxypropyl-β-cyclodextrin (HPBCD), hypromellose (hydroxypropylmethylcellulose, HPMC), polymethacrylates (poly(methacrylic acid, methyl methacrylate 1:1; poly(methacrylic acid, ethyl acrylate) 1:1), hydroxypropyl cellulose (HPC), and cellulose acetate phthalate (CAP).

Copovidone is a synthetic, linear, random copolymer of N-vinyl-2-pyrrolidone (VP) and vinyl acetate (VA) with the chemical formula $(C_6H_9NO)_m$ $(C_4H_6O_2)_n$ where the VA content is nominally 40% (but may vary, for example between 35-41%). The addition of vinyl acetate to the vinylpyrrolidone polymer chain reduces hygroscopicity and glass transition temperature (Tg) of the polymer relative to Povidone (polyvinyl pyrrolidone, PVP homopolymer).

The K-value for copovidone is between 25 and 31, and since the K-value is calculated from the kinematic viscosity of a 1% aqueous solution, it is related to the average molecular weight of the polymer. The average molecular weight (Mw) ranges from ~24,000 to 30,000.

According to one aspect of the invention there is provided a pharmaceutical formulation comprising 4-[3-(4-cyclopropanecarbonyl-piperazine-1-carbonyl)-4-fluoro-benzyl]-2H-phthalazin-1-one in a solid dispersion with copovidone. In one embodiment the pharmaceutical formulation is one suitable for mucosal administration to a patient. A particular mucosal administration route is oral, e.g. a tablet or capsule, and the like.

The invention also provides a daily pharmaceutical dose of 4-[3-(4-cyclopropanecarbonyl-piperazine-1-carbonyl)-4-fluoro-benzyl]-2H-phthalazin-1-one wherein the dose comprises a therapeutically effective amount of 4-[3-(4-cyclopropanecarbonyl-piperazine-1-carbonyl)-4-fluoro-benzyl]-2H-phthalazin-1-one in a solid dispersion with a matrix polymer that exhibits low hygroscopicity and high softening temperature. In one embodiment the matrix polymer is copovidone. In a further embodiment the pharmaceutical formulation is mucosally administrable to a patient.

In a particular embodiment, the therapeutically effective amount of 4-[3-(4-cyclopropanecarbonyl-piperazine-1-carbonyl)-4-fluoro-benzyl]-2H-phthalazin-1-one is in the range 10 to 1000 mg, in a further embodiment the dose comprises 25 to 400 mg of 4-[3-(4-cyclopropanecarbonyl-piperazine-1-carbonyl)-4-fluoro-benzyl]-2H-phthalazin-1-one.

According to a further aspect of the invention there is provided a pharmaceutical formulation comprising 4-[3-(4-cyclopropanecarbonyl-piperazine-1-carbonyl)-4-fluoro-benzyl]-2H-phthalazin-1-one in a solid dispersion with copovidone, and comprising one or more additional compounds useful in the treatment of cancer. In one embodiment the pharmaceutical formulation is for mucosal administration to a patient.

According to a further aspect of the invention there is provided an oral pharmaceutical composition comprising a solid amorphous dispersion comprising an active agent and at least one matrix polymer, wherein the matrix polymer exhibits low hygroscopicity and high softening temperature and wherein the active agent is 4-[3-(4-cyclopropanecarbonyl-piperazine-1-carbonyl)-4-fluoro-benzyl]-2H-phthalazin-1-one or a pharmaceutically acceptable salt or solvate thereof.

Further aspects of the invention relate to the use of a matrix polymer that exhibits low hygroscopicity and high softening temperature, such as copovidone, in solid dispersion with 4-[3-(4-cyclopropanecarbonyl-piperazine-1-carbonyl)-4-fluoro-benzyl]-2H-phthalazin-1-one or a pharmaceutically acceptable salt or solvate thereof, in the manufacture of a medicament, particularly for treating cancer; and, a method of treating cancer comprising administration to a patient in need thereof of a therapeutically effective amount of a formulation comprising 4-[3-(4-cyclopropanecarbonyl-piperazine-1-carbonyl)-4-fluoro-benzyl]-2H-phthalazin-1-one or a pharmaceutically acceptable salt or solvate thereof, in solid dispersion with a matrix polymer that exhibits low hygroscopicity and high softening temperature, such as copovidone. In such aspects, the medicament may comprise from 10 to 1500 mg of Compound 1, such as from 10 to 1000 mg and from 25-400 mg.

Further aspects of the invention relate to: a method for increasing the bioavailability of the drug 4-[3-(4-cyclopropanecarbonyl-piperazine-1-carbonyl)-4-fluoro-benzyl]-2H-phthalazin-1-one in a patient in need of said drug, comprising administering to said patient a formulation comprising 4-[3-(4-cyclopropanecarbonyl-piperazine-1-carbonyl)-4-fluoro-benzyl]-2H-phthalazin-1-one in a solid dispersion with a matrix polymer that exhibits low hygroscopicity and high softening temperature; and, a daily pharmaceutical dose of 4-[3-(4-cyclopropanecarbonyl-piperazine-1-carbonyl)-4 fluoro-benzyl]-2H-phthalazin-1-one for treating cancer in the patient, wherein the dose comprises 10 to 1000 mg of 4-[3-(4-cyclopropanecarbonyl-piperazine-1-carbonyl)-4-fluoro-benzyl]-2H-phthalazin-1-one in a solid dispersion with a matrix polymer that exhibits low hygroscopicity and high softening temperature. In a particular embodiment of these aspects the matrix polymer is copovidone.

According to a further aspect of the invention there is provided a method of producing a solid amorphous dispersion of 4-[3-(4-cyclopropanecarbonyl-piperazine-1-carbonyl)-4-fluoro-benzyl]-2H-phthalazin-1-one comprising:

(i) mixing a suitable amount of 4-[3-(4-cyclopropanecarbonyl-piperazine-1-carbonyl)-4-fluoro-benzyl]-2H-phthalazin-1-one or a pharmaceutically acceptable salt or solvate thereof with a desired amount of at least one matrix polymer, wherein the matrix polymer exhibits low hygroscopicity and high softening temperature;

(ii) increasing the temperature of the mixture to produce a melt; and (iii) extruding the melt to produce a solid product.

In step (iii) the melt may be extruded as a solid rod which may then be further processed, for example by milling, to produce a powder suitable for use in a pharmaceutical formulation. Alternatively, the melt may be extruded into one or more moulds. Such moulds may, for example provide for shaped products such as elliptical or tablet shapes.

In step (ii) the melt could be produced by applying thermal heat and/or mechanical stress.

According to the various aspects of the invention a particular ratio of 4-[3-(4-cyclopropanecarbonyl-piperazine-1-carbonyl)-4-fluoro-benzyl]-2H-phthalazin-1-one:matrix polymer by weight is from 1:0.25 to 1:10. More preferably the lower limit of the range is 1:≥4, 1:5 or 1:7. Preferably, the upper limit of this range is 1:≤2, 1:1, 1:0.5 or 1:0.3. Suitable ratios are 1:2, 1:3 and 1:4. In one embodiment, the range is 1:≥2 to 1:10. In another embodiment, the solid dispersion includes a surface-active agent and/or a plasticiser. Further discussion of surface-active agents and plasticisers appears below.

As used herein, the phrase "therapeutically effective amount" means the drug dosage that provides the specific pharmacological response for which the drug is administered in a significant number of subjects in need of such treatment. It is emphasized that a therapeutically effective amount of a drug that is administered to a particular subject in a particular instance will not always be effective in treating the conditions/diseases described herein, even though such dosage is deemed to be a therapeutically effective amount by those of skill in the art. By way of example, the therapeutically effective amount of 4-[3-(4-cyclopropanecarbonyl-piperazine-1-carbonyl)-4-fluoro-benzyl]-2H-phthalazin-1-one could be 25 mg, 50 mg, 100 mg, 150 mg, 200 mg, 250 mg, 300 mg, 400 mg, 500 mg, 600 mg or 750 mg once or twice a day.

The solid dispersion formulations of the invention exhibit increased bioavailability and drug loading potential and are thus likely to require fewer dose units compared to conventional/immediate release 4-[3-(4-cyclopropanecarbonyl-piperazine-1-carbonyl)-4-fluoro-benzyl]-2H-phthalazin-1-one formulations.

One aspect of the invention provides a daily pharmaceutical dose of 4-[3-(4-cyclopropanecarbonyl-piperazine-1-carbonyl)-4-fluoro-benzyl]-2H-phthalazin-1-one for treating cancer in a patient, wherein the dose comprises 10 to 1500 mg of 4-[3-(4-cyclopropanecarbonyl-piperazine-1-carbonyl)-4-fluoro-benzyl]-2H-phthalazin-1-one in a solid dispersion with a matrix polymer that exhibits low hygroscopicity and high softening temperature, such as copovidone. In one embodiment the pharmaceutical dose is administrable to a patient mucosally. In another embodiment the dose comprises 25 to 600 mg of 4-[3-(4-cyclopropanecarbonyl-piperazine-1-carbonyl)-4-fluoro-benzyl]-2H-phthalazin-1-one.

In various embodiments, the dose comprises 1500, 1250, 1000, 800, 700, 600, 500, 450, 400, 300, 250, 225, 200, 175, 150, 125, 100, 75, 50, 25, 15 or 10 mg of 4-[3-(4-cyclopropanecarbonyl-piperazine-1-carbonyl)-4-fluoro-benzyl]-2H-phthalazin-1-one. In particular embodiments, the dose comprises 25, 50, 100, 200 or 400 mg of 4-[3-(4-cyclopropanecarbonyl-piperazine-1-carbonyl)-4-fluoro-benzyl]-2H-phthalazin-1-one.

Additional excipients may be included in the formulation or dose. For example, the formulation or dose may comprise one or more fillers, binders, disintegrants and/or lubricants.

Suitable fillers include, for example, lactose, sugar, starches, modified starches, mannitol, sorbitol, inorganic salts, cellulose derivatives (e.g. microcrystalline cellulose, cellulose), calcium sulphate, xylitol and lactitol.

Suitable binders include, for example, lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatine, polyvinylpyrrolidone (PVP) and sodium alginate.

Suitable disintegrants include, for example, crosscarmellose sodium, crospovidone, polyvinylpyrrolidone, sodium starch glycollate, corn starch, microcrystalline cellulose, hydroxypropyl methylcellulose and hydroxypropyl cellulose.

Suitable lubricants include, for example, magnesium stearate, magnesium lauryl stearate, sodium stearyl fumarate, stearic acid, calcium stearate, zinc stearate, potassium benzoate, sodium benzoate, myristic acid, palmitic acid, mineral oil, hydrogenated castor oil, medium-chain triglycerides, poloxamer, polyethylene glycol and talc.

Additional conventional excipients, which may be added, include preservatives, stabilisers, anti-oxidants, silica flow conditioners, antiadherents or glidants.

Other suitable fillers, binders, disintegrants, lubricants and additional excipients which may be used are described in the Handbook of Pharmaceutical Excipients, 5th Edition (2006); The Theory and Practice of Industrial Pharmacy, 3rd Edition 1986; Pharmaceutical Dosage Forms 1998; Modern Pharmaceutics, 3rd Edition 1995; Remington's Pharmaceutical Sciences 20th Edition 2000.

In certain embodiments, the 4-[3-(4-cyclopropanecarbonyl-piperazine-1-carbonyl)-4-fluoro-benzyl]-2H-phthalazin-1-one will be present in an amount of 10 to 70%, and preferably from 15 to 50% (more preferably 20 to 30% or 25 to 35%) by weight of the solid dispersion.

In certain embodiments, one or more fillers will be present in an amount of 1 to 70% by weight of the formulation or dose.

In certain embodiments, one or more binders will be present in an amount of 2 to 40% by weight of the formulation or dose.

In certain embodiments, one or more disintegrants will be present in an amount of 1 to 20%, and especially 4 to 10% by weight of the formulation or dose.

It will be appreciated that a particular excipient may act as both a binder and a filler, or as a binder, a filler and a disintegrant. Typically the combined amount of filler, binder and disintegrant comprises, for example, 1 to 90% by weight of the formulation or dose.

In certain embodiments, one or more lubricants will be present in an amount of 0.5 to 3%, and especially 1 to 2% by weight of the formulation or dose.

In certain embodiments, one or more surface-active agents will be present in the solid dispersion in an amount of 0.1 to 50%, preferably ≤5% (eg, 1 to 2%) by weight of the solid dispersion. The presence of a surface-active agent provides a further enhancement of the increase in therapeutic potential achieved with the present invention. Examples of suitable surface-active agents include: anionic surfactants such as sodium dodecyl sulphate (sodium lauryl sulphate); docusate sodium; cationic surfactants such as cetrimide, benzethonium chloride, cetylpyridinium chloride and lauric acid; nonionic surfactants such as polyoxyethylene alkyl ethers, polyoxyethylene sorbitan fatty acid esters, e.g. polysorbates 20, 40, 60 and 80; polyoxyethylene castor oil derivatives, e.g. Cremophor RH40™; polyoxyethylene stearates and poloxamers.

In certain embodiments, one or more plasticisers will be present in the solid dispersion in an amount of 0.1% to 50%, preferably ≤5% (e.g. 1 to 2%) by weight of the solid dispersion. The presence of a plasticiser may enhance processability of the solid dispersion, for example when a melt extrusion process is used. Examples of suitable plasticisers include: acetyltributyl citrate, acetyltriethyl citrate, benzyl benzoate, chlorbutanol, dextrin, dibutyl phthalate, diethyl phthalate, dimethyl phthalate, glycerine, glycerine monostearate, mannitol, mineral oil, lanolin alcohols, palmitic acid, polyethylene glycol, polyvinyl acetate phthalate, propylene glycol, 2-pyrrolidone, sorbitol, stearic acid, triacetin, tributyl citrate, triethanolamine and triethyl citrate.

The term "solid dispersion" as used herein means systems in which an active agent is dispersed in an excipient carrier. With respect to the state of the drug in the systems, solid dispersions in this sense can include compositions in which the drug is dispersed as discrete domains of crystalline or amorphous drug, or as individual molecules within an excipient carrier. With respect to the complete drug-excipient composite, solid dispersions can be relatively large solid masses such as pellets, tablets, films or strands; or they can exist as free flowing powders consisting of micro- or nano-sized primary particles or aggregates thereof. The bulk state of the solid dispersion composition depends largely upon the mode of processing (Miller, D. A., McGinty, J. W., Williams III, R. O. Solid Dispersion Technologies. Microencapsulation of Oil-in-Water Emulsions 172 (2008) pp 451-491).

In the present invention the definition of a solid dispersion does not encompass physical mixtures from dry or wet mixing or dry blending operations.

Methods for preparing solid dispersions are known in the art and typically comprise the steps of dissolving the drug and the polymer in a common solvent and evaporating the solvent. The solvent can be routinely selected according to the polymer used. Examples of solvents are: acetone, acetone/dichloromethane, methanol/dichloromethane, acetone/water, acetone/methanol, acetone/ethanol, dichloromethane/ethanol or ethanol/water. Methods for evaporating solvent include rotary evaporation, spray drying, lyophilisation and thin film evaporation. Alternatively solvent removal may be accomplished by cryogenic freezing followed by lyophilisation. Other techniques may be used such as melt extrusion, solvent controlled precipitation, pH controlled precipitation, supercritical fluid technology and cryogenic co milling.

This invention further discloses a method of making the 4-[3-(4-cyclopropanecarbonyl-piperazine-1-carbonyl)-4-fluoro-benzyl]-2H-phthalazin-1-one: copovidone solid dispersion. Such a method comprises (i) dissolving a suitable amount of 4-[3-(4-cyclopropanecarbonyl-piperazine-1-carbonyl)-4-fluoro-benzyl]-2H-phthalazin-1-one and matrix polymer in a common solvent; and (ii) removing the solvent. Pharmaceutical compositions comprising the dispersion can be made, for example by adding such things as stabilizers and/or additional excipients as required. In a particular embodiment, the solvent is removed by spray drying.

According to another aspect of the invention the 4-[3-(4-cyclopropanecarbonyl-piperazine-1-carbonyl)-4-fluoro-benzyl]-2H-phthalazin-1-one: copovidone solid dispersion is made by melt extrusion. Such method comprises adding the 4-[3-(4-cyclopropanecarbonyl-piperazine-1-carbonyl)-4-fluoro-benzyl]-2H-phthalazin-1-one, or a pharmaceutically acceptable salt or solvate thereof, and copovidone polymer, and any additional optional excipients, including plasticisers, to a melt extrusion apparatus which then heats and mixes and finally extrudes the solid dispersion product. The extruder heats the mixture to a temperature high enough to melt the mixture but low enough so as to not degrade the constituents.

According to another aspect of the invention there is provided a method of producing a solid amorphous dispersion of 4-[3-(4-cyclopropanecarbonyl-piperazine-1-carbonyl)-4-fluoro-benzyl]-2H-phthalazin-1-one comprising simultaneously exposing 4-[3-(4-cyclopropanecarbonyl-piperazine-1-carbonyl)-4-fluoro-benzyl]-2H-phthalazin-1-one or a pharmaceutically acceptable salt or solvate thereof and at least one matrix polymer, wherein the matrix polymer exhibits low hygroscopicity and high softening temperature, to hot melt extrusion.

According to another aspect of the invention there is provided a method of making a solid dispersion product of 4-[3-(4-cyclopropanecarbonyl-piperazine-1-carbonyl)-4-fluoro-benzyl]-2h-phthalazin-1-one, comprising:
(a) providing a powdered or granulated premix comprising:
 (i) 5-60% by weight of 4-[3-(4-cyclopropanecarbonyl-piperazine-1-carbonyl)-4-fluoro-benzyl]-2h-phthalazin-1-one; and,
 (ii) 40-95% copovidone;
(b) melting the premix, without addition of solvent, in a kneader or an extruder extruder to obtain a homogeneous melt, and
(c) shaping and solidifying the melt to obtain a solid dispersion product.

In one embodiment, the solid dispersion product is formed into a suitable dosage form ready for oral administration.

In another embodiment, the solid dispersion product is ground up, mixed with one or more additional excipients or ingredients, and tableted or encapsulated into a suitable dosage form.

When referring to a solid dispersion we do not exclude the possibility that a proportion of the 4-[3-(4-cyclopropanecarbonyl-piperazine-1-carbonyl)-4-fluoro-benzyl]-2H-phthalazin-1-one may be dissolved within the matrix polymer, the exact proportion, if any, will depend upon the particular polymer selected.

In the formulations of the invention, at least some of the 4-[3-(4-cyclopropanecarbonyl-piperazine-1-carbonyl)-4-fluoro-benzyl]-2H-phthalazin-1-one may be present in amorphous form in the solid dispersion with the matrix polymer. The provision of the 4-[3-(4-cyclopropanecarbonyl-piperazine-1-carbonyl)-4-fluoro-benzyl]-2H-phthalazin-1-one in amorphous form is additionally advantageous, since it further increases the solubility and dissolution rate of the 4-[3-(4-cyclopropanecarbonyl-piperazine-1-carbonyl)-4-fluoro-benzyl]-2H-phthalazin-1-one, thereby enhancing the increase in therapeutic potential achieved with the present invention. Whether or not drug is present in amorphous form can be determined by conventional thermal analysis or X-ray diffraction. In one embodiment, at least 25% of the 4-[3-(4-cyclopropanecarbonyl-piperazine-1-carbonyl)-4-fluoro-benzyl]-2H-phthalazin-1-one in the formulation is present in amorphous form, as measured using XRPD. More preferably, this amount is at least 30%, 40%, 50%, 75%, 90%, 95%, as measured using XRPD. The most preferred embodiment is where 100% of the 4-[3-(4-cyclopropanecarbonyl-piperazine-1-carbonyl)-4-fluoro-benzyl]-2H-phthalazin-1-one in the formulation is in amorphous form. In reality, current XRPD tools and techniques may only be able to detect >5% crystalline form, and thus the inability to detect crystalline form may mean that the sample is between 95% and 100% amorphous.

XRPD may be augmented by emerging nanometer-scale characterisation techniques: Pair-wise Distribution Function (transformation of the X-ray diffraction pattern to a normalised scattering function) may facilitate the detection of nanocrystallinity; Solid State NMR proton spin diffusion studies may be used to detect phase separation, as may Atomic Force Microscopy and Nanothermal analysis. Such techniques are comparative rather than absolute but are useful tools in the development and optimisation of pharmaceutical solid dispersion formulations.

In a further embodiment, the drug is in stable amorphous form, by which is meant that the stability (ability to remain in amorphous form and resist converting to crystalline form) of the amorphous state of Compound 1 is extended in the solid dispersion formulation of the invention relative to the stability of the amorphous state of Compound 1 on its own.

In a preferred embodiment, the formulations and doses are mucosally administrable, i.e. administrable to mucosal membranes for absorption across the membranes. To this end, suitable routes of administration include administration by inhalation, as well as oral, intranasal and rectal administration. Oral administration is particularly preferred. A tablet, capsule or other form of the formulation would be chosen by the skilled addressee according to the route of administration. Other routes of administration, e.g. parenteral are however not excluded.

The 4-[3-(4-cyclopropanecarbonyl-piperazine-1-carbonyl)-4-fluoro-benzyl]-2H-phthalazin-1-one is useful to provide a poly-ADP-ribose polymerase (PARP) inhibitory effect. This effect is useful for treating cancer, for example breast or ovarian cancer, and particularly cancers that possess a defective homologous recombination (HR) dependent DNA double-stranded break (DSB) repair pathway, such as BRCA1+ and/or BRCA2+ve cancers.

Another aspect of the invention is directed to a 4-[3-(4-cyclopropanecarbonyl-piperazine-1-carbonyl)-4-fluoro-benzyl]-2H-phthalazin-1-one composition, comprising 4-[3-(4-cyclopropanecarbonyl-piperazine-1-carbonyl)-4-fluoro-benzyl]-2H-phthalazin-1-one in solid dispersion with copovidone, and comprising one or more additional compounds useful in the treatment of cancer.

Particularly, useful "additional" anti-cancer compounds include DNA damage promoting agents. A DNA damage promoting agent is a compound (such as a small organic molecule, peptide or nucleic acid) which increases the amount of DNA damage in a cell, either directly or indirectly, for example through inhibition of DNA repair. The DNA damage promoting agent is often a small organic molecule compound.

Suitable DNA damage promoting agents include agents which damage DNA in a cell (i.e. DNA damaging agents), for example alkylating agents such as methyl methanesulfonate (MMS), temozolomide, dacarbazine (DTIC), cisplatin, oxaliplatin, carboplatin, cisplatin-doxorubicin-cyclophosphamide, carboplatin-paclitaxel, cyclophosphamide, nitrogen mustard, melphalan, chlorambucil, busulphan, etoposide, teniposide, amsacrine, irinotecan, topotecan and rubitecan and nitrosoureas, topoisomerase-1 inhibitors like Topotecan, Irinotecan, Rubitecan, Exatecan, Lurtotecan, Gimetecan, Diflomotecan (homocamptothecins); as well as 7-substituted non-silatecans; the 7-silyl camptothecins, BNP 1350; and non-camptothecin topoisomerase-I inhibitors such as indolocarbazoles, topoisomerase-II inhibitors like Doxorubicin, Danorubicin, and other rubicins, the acridines (Amsacrine, m-AMSA), Mitoxantrone, Etopside, Teniposide and AQ4, dual topoisomerase-I and II inhibitors like the benzophenazines, XR 11576/MLN 576 and benzopyridoindoles, and antimetabolites such as gemcitabine, antifolates such as fluoropyrimidines like 5 fluorouracil and tegafur, raltitrexed, methotrexate, cytosine arabinoside, and hydroxyurea, and arsenic trioxide.

The patient can be a human, e.g. an adult or a child, but the treatment of other mammals is also contemplated.

Aspects of the present invention will now be illustrated with reference to the accompanying figures described below and experimental exemplification, by way of example and not limitation. Further aspects and embodiments will be apparent to those of ordinary skill in the art.

BRIEF DESCRIPTION OF DRAWINGS

FIG. 8(1) is the 50 μm×50 μm topographic (height)
FIG. 8(2) is the 50 μm×50 μm tip-deflection (error)
FIG. 8(3) is the 50 μm×50 μm phase (mechanical property)
FIG. 8(4) is the 10 μm×10 μm topographic (height)
FIG. 8(5) is the 10 μm×10 μm tip-deflection (error)
FIG. 8(6) is the 10 μm×10 μm phase (mechanical property)

FIG. 9(1) is the 50 μm×50 μm topographic (height)
FIG. 9(2) is the 50 μm×50 μm tip-deflection (error)
FIG. 9(3) is the 50 μm×50 μm phase (mechanical property)
FIG. 9(4) is the 10 μm×10 μm topographic (height)
FIG. 9(5) is the 10 μm×10 μm tip-deflection (error)
FIG. 9(6) is the 10 μm×10 μm phase (mechanical property)

FIG. 31 shows the protocol for the screening study of Compound 1 solid dispersions: [a] Poloxamer F127, PVP K30, Hydroxypropyl cellulose, Copovidone and Polyacrylic acid were not assessed in DCM/MeOH; [b] Only PVP K25, HPMC Phthalate and Kleptose were assessed without additive at 33% loading; [c] Kleptose/PVP K25 blend assessed using Acetone/MeOH solvent system only in ratios 5:70 and 10:65 at 25% drug loading and in ratios 5:45 and 10:40 at 50% drug loading, without additive; and [d] Kleptose/HPMC606 blend assessed as described above for Kleptose/PVP K25 blend

EXAMPLE 1. CHARACTERISTICS OF COMPOUND 1

1.1 Solubility

The solubility of crystalline Form A of Compound 1 was measured in water and a range of pH buffered solutions representing the physiological pH range. The physical form of any undissolved (or precipitated) Compound 1 was not assessed by XRPD after solubility determination. Solubility data are summarised in Table 1. The Form A crystalline form of Compound 1 is disclosed in WO2008/047082.

TABLE 1

Solubility of crystalline Compound 1 (Form A) in a range of buffers representing the physiological pH range (mg · mL$^{-1}$)

| Media | 1 hr | pH | 24 hr | pH |
|---|---|---|---|---|
| Water | 0.124 | 5.6 | 0.109 | 6.0 |
| 0.1M HCl | 0.128 | 1.2 | 0.114 | 1.2 |
| pH 3 Citrate Buffer | 0.124 | 2.9 | 0.112 | 2.9 |
| pH 6.8 Phosphate Buffer | 0.111 | 6.9 | 0.096 | 6.9 |
| pH 9 Buffer | 0.116 | 8.9 | 0.102 | 8.8 |
| 0.1M NaOH | 0.650 | 12.5 | 0.599 | 12.4 |

The solubility of Compound 1 was also measured in real and simulated gastrointestinal media (Table 2). Solubility in HIF and FeSSIF was notably higher than buffer solubilities reported in Table 1.

TABLE 2

Solubility of crystalline Compound 1 (Form A) real and simulated gastrointestinal media

| Media | Equilibrium solubility (mg · mL$^{-1}$), 24 hr |
|---|---|
| Simulated Gastric Fluid (SGF)[1] | 0.12 |
| Human Gastric Fluid (HGF)[2] | 0.15 |
| Fed State Simulated Intestinal Fluid (FeSSIF)[3] | 0.2 |
| Fasted State Simulated Intestinal Fluid (FaSSIF)[3] | 0.13 |
| Human Intestinal Fluid (HIF)[2] | 0.17 |

[1]SGF contains 3.2 g pepsin, 2.0 g sodium chloride, and 7.0 mL hydrochloric acid per liter.
[2]Pooled from healthy volunteers; supplied by Uppsala Universitet, Box 256, 751 05 Uppsala, Sweden
[3]Marques, M. Dissolution media simulating fasted and fed states. Dissolution Technologies (May 2004) pp 16.

1.2 Permeability

Figure 1:
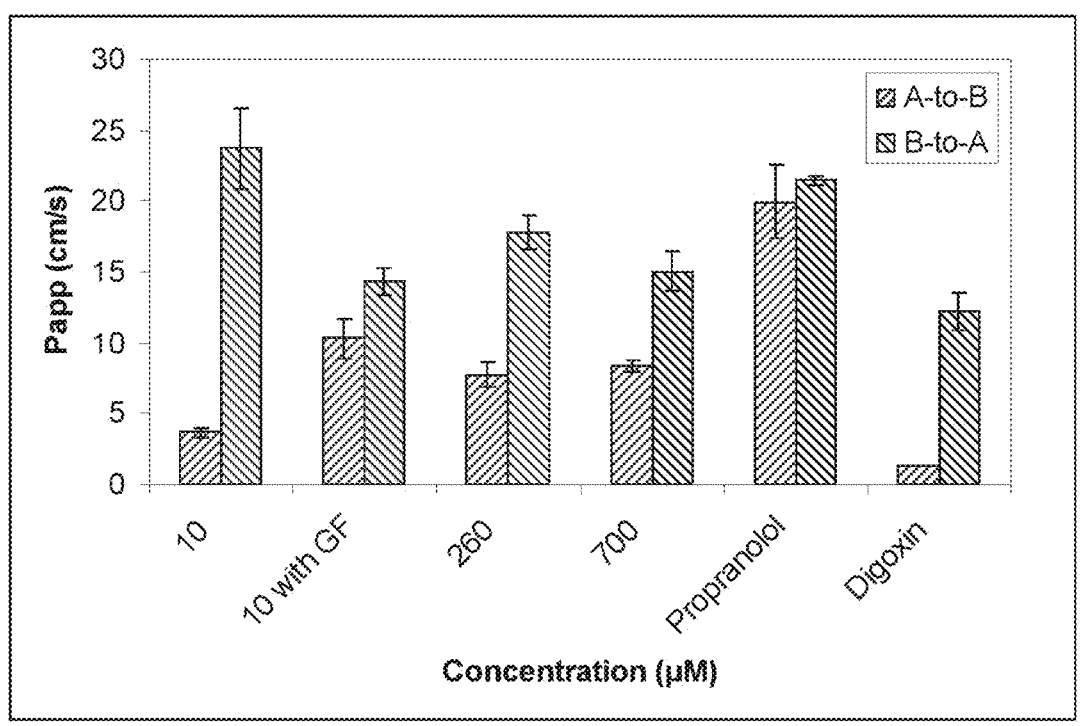
FIG. 1 shows permeability of Compound 1 across Caco-2 monolayers (n=3, ±s.d.)

Compound 1 was determined to be moderately permeable when compared to the high permeability marker propranolol, investigated using a validated Caco-2 cell line, results are summarised in Table 3 and FIG. 1. Compound 1 was shown to have propensity for efflux by P-gp at low concentrations (10 µM), which was inhibited by the selective P-gp inhibitor Elacridar (GF120918; GG918; N-(4-[2-(1,2,3,4-tetrahydro-6,7-dimethoxy-2-isoquinolyl)ethyl]phenyl)-9,10-dihydro-5-methoxy-9-oxo-4-acridine carboxamide, hydrochloride salt.

TABLE 3

Permeability of Compound 1 across Caco-2 monolayers (n = 3, ±S.D.), compared to the high permeability marker propranolol and the efflux marker digoxin

| | $P_{app}$ (cm · sec$^{-1}$) | | |
|---|---|---|---|
| Concentration (µM) | A-to-B | B-to-A | Efflux Ratio |
| 10 | 3.67 ± 0.34 | 23.70 ± 2.84 | 6.5 |
| 10 with Elacridar | 10.34 ± 1.38 | 14.29 ± 0.93 | 1.4 |
| 260 | 7.75 ± 0.88 | 17.75 ± 1.19 | 2.3 |
| 700 | 8.4 ± 0.41 | 15.06 ± 1.42 | 1.8 |
| Propranolol | 19.97 ± 2.57 | 21.48 ± 0.33 | 1.1 |
| Digoxin | 1.34 ± 0.03 | 12.22 ± 1.37 | 9.1 |

Key:
A = apical;
B = basolateral

See FIG. 1.

EXAMPLE 2. POLYMER CHARACTERISTICS

TABLE 4

Characteristics of polymers used in pharmaceutical solid dispersion formulations

| Polymer | Grade | Supplier | Hygro-scopicity (% w/w)[a] | Softening Point[b] Tg (° C.) | Tm (° C.) |
|---|---|---|---|---|---|
| Copovidone | Kollidon VA64 | BASF SE | 5 | 106 | N/A |
| Povidone | Kollidon 17PF | | 16 | 136 | N/A |

TABLE 4-continued

Characteristics of polymers used in pharmaceutical solid dispersion formulations

| Polymer | Grade | Supplier | Hygro-scopicity (% w/w)[a] | Softening Point[b] Tg (° C.) | Softening Point[b] Tm (° C.) |
|---|---|---|---|---|---|
| | Kollidon 25 | | | 155 | N/A |
| | Kollidon 30 | | | 168 | N/A |
| Hypromellose phthalate (HPMCP) | HP55S | Shin-Etsu Chemical Co., Ltd | 4 | 145 | N/A |
| | HP55 | | | 145 | N/A |
| Hypromellose acetate succinate (HPMCAS) | Aqoat LF | | 4 | 120 | N/A |
| | Aqoat LG | | | 120 | N/A |
| | Aqoat MG | | | 130 | N/A |
| 2-hydroxypropyl-β-cyclodextrin (HPBCD) | Kleptose HP | Roquette Freres | 7 | 278 | N/A |
| Hypromellose (HPMC) | Pharmacoat 606 | Shin-Etsu Chemical Co., Ltd | 4 | 175 | N/A |
| Poly(methacrylic acid, ethyl acrylate) 1:1 | Eudragit L100-55 | Evonik Degussa GmbH | 4 | 115 | N/A |
| Poly(methacrylic acid, methyl methacrylate) 1:1 | Eudragit L100 | | 6 | 160[#] | N/A |
| Poly(butylmethacrylate, (2-dimethylaminoethyl) methacrylate, methyl methacrylate) 1:2:1 acid, ethyl acrylate) 1:1 | Eudragit E100 | | 1 | 48 | N/A |
| Poly(methacrylic acid, methyl methacrylate) 1:2 | Eudragit S100 | | 11 | 160[#] | N/A |
| Polyethylene glycol (PEG) | PEG 6000 | Fluka AG | 2 | N/A | 55-63 |
| Poloxamer | Pluronic (Lutrol) F68 | BASF SE | 2 | N/A | 52-57 |
| | Pluronic (Lutrol) F127 | | | N/A | 52-57 |
| Hydroxypropyl cellulose (HPC) | Klucel EF | Hercules, Inc. | 5 | 130 | N/A |
| Cellulose acetate phthalate (CAP) | Aquacoat CPD | FMC Biopolymer | 6 | 176 | N/A |

Key:
N/A = Not Applicable
[a]Equilibrium water content at 50% Relative Humidity (literature values)
[b]Softening temperature expressed as glass transition temperature (Tg) or melting point (Tm) - suppliers data
[#]Accurate determination not possible due to chemical degradation

Figure 3:
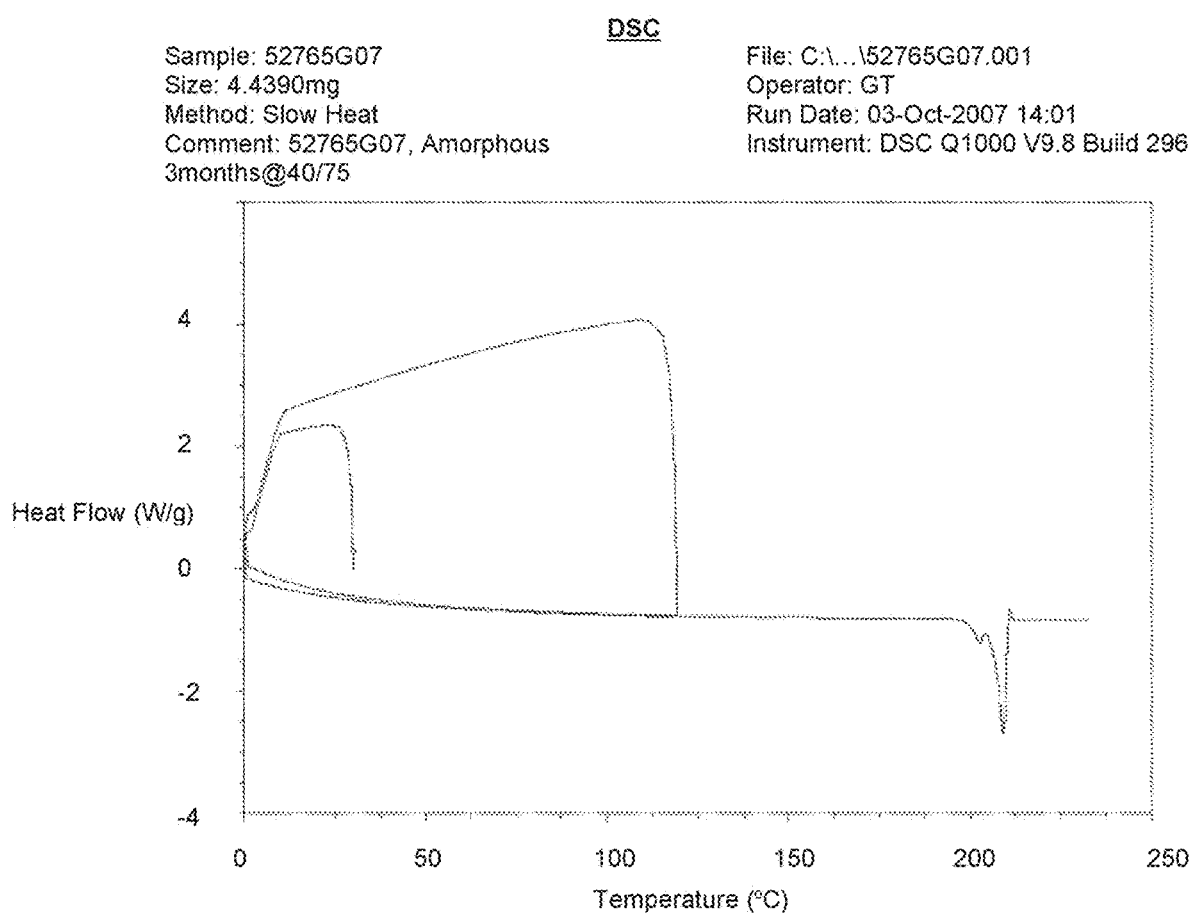
FIG. 3 shows a thermogram of a solid dispersion exhibiting a melt transition due to the presence of crystalline Compound 1

EXAMPLE 3. SCREENING STUDY—POLYMERIC DISPERSIONS 3.1 Protocol
See FIG. 31
3.2 Methodology A series of 4% w/w solutions, comprising binary mixtures of Compound 1 and each of the polymers in the proportions specified in the protocol, were prepared by weighing into 1.8 mL vials and dissolving in the specified solvent system. Further solutions comprising ternary mixtures of Compound 1, polymer and surfactant were prepared in a similar manner. Solvent was removed by evaporation at 40° C. under nitrogen (10 mL/min flow, 0.7 bar pressure) for 15 minutes followed by drying overnight under full vacuum to produce a solid dispersion.

The resulting samples were assessed using XRPD (Bruker GADDS diffractometer; data collection at room temperature using CuK$_α$ radiation in the 2θ region between 1.5 and 41.5°), immediately after preparation and after storage for up to 1 month at 30° C. and 60% RH.

3.3 Results

TABLE 5

Results for the screening study of Compound 1 solid dispersions

| Polymer | Solvent System | Drug (% w/w) | Additive | XRPD (crystalline Compound 1) After Prep. | 30° C./60% RH 1 week | 30° C./60% RH 1 month |
|---|---|---|---|---|---|---|
| PEG6000 | DCM/MeOH | 25 | None | N/D | Present | N/T |
| PEG6000 | DCM/MeOH | 50 | None | N/D | Present | N/T |
| PEG6000 | Acetone/MeOH | 25 | None | N/D | Present | N/T |
| PEG6000 | Acetone/MeOH | 50 | None | N/D | Present | N/T |
| PEG6000 | Acetone/MeOH | 33 | SLS | N/D | N/T | Present |
| PEG6000 | Acetone/MeOH | 33 | Tween 80 | N/D | N/T | Present |

TABLE 5-continued

Results for the screening study of Compound 1 solid dispersions

| Polymer | Solvent System | Drug (% w/w) | Additive | After Prep. | XRPD (crystalline Compound 1) 30° C./60% RH 1 week | 1 month |
|---|---|---|---|---|---|---|
| PEG6000 | Acetone/MeOH | 33 | Doc. Na | N/D | N/T | Present |
| Poloxamer F68 | DCM/MeOH | 25 | None | N/D | Present | N/T |
| Poloxamer F68 | DCM/MeOH | 50 | None | N/D | Present | N/T |
| Poloxamer F68 | Acetone/MeOH | 25 | None | N/D | Present | N/T |
| Poloxamer F68 | Acetone/MeOH | 50 | None | N/D | N/D | N/T |
| Poloxamer F68 | Acetone/MeOH | 33 | SLS | N/D | N/T | Present |
| Poloxamer F68 | Acetone/MeOH | 33 | Tween 80 | N/D | N/T | Present |
| Poloxamer F68 | Acetone/MeOH | 33 | Doc. Na | N/D | N/T | Present |
| Poloxamer F127 | Acetone/MeOH | 25 | None | N/D | Present | N/T |
| Poloxamer F127 | Acetone/MeOH | 50 | None | N/D | Present | N/T |
| PVP K25 | DCM/MeOH | 25 | None | N/D | N/D | N/T |
| PVP K25 | DCM/MeOH | 50 | None | N/D | N/D | N/T |
| PVP K25 | Acetone/MeOH | 25 | None | | Not harvested | |
| PVP K25 | Acetone/MeOH | 33 | None | N/D | N/D | N/T |
| PVP K25 | Acetone/MeOH | 50 | None | | Not harvested | |
| PVP K25 | Acetone/MeOH | 33 | SLS | N/D | N/T | N/D |
| PVP K25 | Acetone/MeOH | 33 | Tween 80 | N/D | N/T | N/D |
| PVP K25 | Acetone/MeOH | 33 | Doc. Na | N/D | N/T | N/D |
| PVP K30 | Acetone/MeOH | 25 | None | N/D | N/D | N/T |
| PVP K30 | Acetone/MeOH | 50 | None | N/D | N/D | N/T |
| HPMC-606 | DCM/MeOH | 25 | None | N/D | N/D | N/T |
| HPMC-606 | DCM/MeOH | 50 | None | N/D | N/D | N/T |
| HPMC-606 | Acetone/MeOH | 25 | None | | Not harvested | |
| HPMC-606 | Acetone/MeOH | 50 | None | | Not harvested | |
| HPMC-606 | Acetone/MeOH | 33 | SLS | N/D | N/T | N/D |
| HPMC-606 | Acetone/MeOH | 33 | Tween 80 | N/D | N/T | N/D |
| HPMC-606 | Acetone/MeOH | 33 | Doc. Na | N/D | N/T | N/D |
| HPMC Phthalate | DCM/MeOH | 25 | None | N/D | N/D | N/T |
| HPMC Phthalate | DCM/MeOH | 50 | None | N/D | N/D | N/T |
| HPMC Phthalate | Acetone/MeOH | 33 | None | | Not harvested | |
| HPMC Phthalate | Acetone/MeOH | 33 | None | | Not harvested | |
| HPMC Phthalate | Acetone/MeOH | 33 | SLS | N/D | N/T | N/D |
| HPMC Phthalate | Acetone/MeOH | 33 | Tween 80 | | Not harvested | |
| HPMC Phthalate | Acetone/MeOH | 33 | Doc. Na | N/D | N/T | N/D |
| Eudragit L100-55 | DCM/MeOH | 25 | None | N/D | Present | N/T |
| Eudragit L100-55 | DCM/MeOH | 50 | None | N/D | Present | N/T |
| Eudragit L100-55 | Acetone/MeOH | 25 | None | N/D | N/D | N/T |
| Eudragit L100-55 | Acetone/MeOH | 50 | None | N/D | N/D | N/T |
| Eudragit L100-55 | Acetone/MeOH | 33 | SLS | N/D | N/T | N/D |
| Eudragit L100-55 | Acetone/MeOH | 33 | Tween 80 | N/D | N/T | N/D |
| Eudragit L100-55 | Acetone/MeOH | 33 | Doc. Na | N/D | N/T | N/D |
| Eudragit E100 | DCM/MeOH | 25 | None | N/D | N/D | N/T |
| Eudragit E100 | DCM/MeOH | 50 | None | N/D | N/D | N/T |
| Eudragit E100 | Acetone/MeOH | 25 | None | N/D | N/D | N/T |
| Eudragit E100 | Acetone/MeOH | 50 | None | Present[1] | N/T | Present[1] |

TABLE 5-continued

Results for the screening study of Compound 1 solid dispersions

| Polymer | Solvent System | Drug (% w/w) | Additive | XRPD (crystalline Compound 1) After Prep. | 30° C./60% RH 1 week | 30° C./60% RH 1 month |
|---|---|---|---|---|---|---|
| Eudragit E100 | Acetone/MeOH | 33 | SLS | N/D | N/T | N/D |
| Eudragit E100 | Acetone/MeOH | 33 | Tween 80 | N/D | N/T | N/D |
| Eudragit E100 | Acetone/MeOH | 33 | Doc. Na | N/D | N/T | N/D |
| Kleptose HP | DCM/MeOH | 25 | None | N/D | N/D | N/T |
| Kleptose HP | DCM/MeOH | 50 | None | N/D | N/D | N/T |
| Kleptose HP | Acetone/MeOH | 25 | None | N/D | N/D | N/T |
| Kleptose HP | Acetone/MeOH | 33 | None | N/D | N/T | N/D |
| Kleptose HP | Acetone/MeOH | 50 | None | N/D | N/D | N/T |
| Kleptose HP | Acetone/MeOH | 33 | None | N/D | N/T | N/D |
| Kleptose HP | Acetone/MeOH | 33 | None | N/D | N/T | N/D |
| Kleptose HP | Acetone/MeOH | 33 | None | N/D | N/T | N/D |
| HPC | Acetone/MeOH | 25 | None | N/D | N/D | N/T |
| HPC | Acetone/MeOH | 50 | None | N/D | N/D | N/T |
| Copovidone | Acetone/MeOH | 25 | None | N/D | N/D | N/T |
| Copovidone | Acetone/MeOH | 50 | None | Present | Present | N/T |
| Kleptose/PVP K25 (70:5) | Acetone/MeOH | 25 | None | N/D | N/T | N/D |
| Kleptose/PVP K25 (45:5) | Acetone/MeOH | 50 | None | N/D | N/T | N/D |
| Kleptose/PVP K25 (65:10) | Acetone/MeOH | 25 | None | N/D | N/T | N/D |
| Kleptose/PVP K25 (40:10) | Acetone/MeOH | 50 | None | N/D | N/T | N/D |
| Kleptose/HPMC-606 (70:5) | Acetone/MeOH | 25 | None | N/D | N/D | N/T |
| Kleptose/HPMC-606 (45:5) | Acetone/MeOH | 50 | None | N/D | N/D | N/T |
| Kleptose/HPMC-606 (65:10) | Acetone/MeOH | 25 | None | N/D | N/D | N/T |
| Kleptose/HPMC-606 (40:10) | Acetone/MeOH | 50 | None | N/D | N/D | N/T |

Key:
N/D = not detected
N/T = not tested
[1]Test performed in a separate study from other Eudragit E100 entries The results of the screening study demonstrate that preparation of amorphous solid dispersions was possible for all of the polymers evaluated. However, solid dispersions produced using the low-melting poloxamers and polyethylene glycol were highly unstable, leading to the formation of crystalline drug within 1 month when stored at 30° C./60% relative humidity. No further evaluation of these polymers was performed. Solid dispersions produced with Eudragit E100 at 25% drug loading appeared to be amorphous and stable; however, crystallisation was immediately apparent at 50% drug loading. Literature reports indicate that dispersions produced with Eudragit E may exhibit significant crystallinity (e.g. see Qi et al. Int. J. Pharm. 354:158-167, 2008); and, in a comparative study, may be less chemically stable than solid dispersions produced using Povidone K25 (Dargel, E., Mielck, J. B. Acta Pharm. Technol. 35(4):197-209. 1989). No further evaluation of Eudragit E100 was performed. Solid dispersions produced with Eudragit L100-55 using a DCM/MeOH solvent system exhibited crystallisation after 1 week at 30° C./60% relative humidity, but those produced using an acetone/MeOH solvent system were stable. We found that solid dispersions produced with copovidone at 50% drug loading exhibited some crystallisation after 1 week at 30° C./60% relative humidity, but those produced at 25% drug loading were stable.

EXAMPLE 4. COMPOUND 1 FORMULATIONS 4.1 Immediate Release Tablet
4.1.1 Composition

TABLE 6

Composition of an immediate release tablet

| Ingredient | mg/tablet | % of core weight | Function |
|---|---|---|---|
| Compound 1 | 100.00 | 25.00 | Drug substance |
| Lactose | 238.00 | 59.50 | Filler |

TABLE 6-continued

Composition of an immediate release tablet

| Ingredient | mg/tablet | % of core weight | Function |
|---|---|---|---|
| Microcrystalline cellulose | 40.00 | 10.00 | Filler |
| Croscarmellose Na | 16.00 | 4.00 | Disintegrant |
| Sodium Lauryl Sulphate | 2.00 | 0.50 | Surfactant |
| Magnesium stearate | 4.00 | 1.00 | Lubricant |
| Core tablet weight | 400.00 | | |

4.1.2 Method of Preparation

Standard immediate release tablets were manufactured using a direct compression process. Crystalline compound 1 and the lactose, microcrystalline cellulose, Croscarmellose Na and Sodium Lauryl Sulphate were weighed into a glass vial to occupy approximately 75% of the volume of the vial and then mixed together in a tumble mixer for 30 minutes. The blended material was sieved through a 40 mesh (425 µm) sieve, then tumble mixed for a further 15 minutes. The magnesium stearate was then added and the blend was shaken manually for about 20 seconds. The resultant mixture was then dispensed into 400 mg portions and compressed into tablet cores, using a hand press equipped with 10 mm tooling and with a target compression force of 0.5 tonnes.

4.2 Microsuspension

4.2.1 Method of Preparation

Approximately 1 g of crystalline Compound 1 was weighed into a 10 mL volumetric flask and 0.5% HPMC (hydroxypropyl methyl cellulose or Hypromellose, USP substitution type 2910 having nominal apparent viscosity 4000 cP, such as DOW Methocel E4M or equivalent) solution was added to volume. The mixture was stirred overnight then quantitatively diluted to 100 mL with 0.5% HPMC solution to give a 10 mg/mL microsuspension. The mean volume diameter of the Compound 1 was determined to be 4.54 µm by laser diffraction using a Sympatec particle size analyser (Sympatec GmbH).

4.3 Gelucire Capsule
4.3.1 Formulation

TABLE 7

Quantitative composition of Compound 1 50 mg capsules

| Constituent | Amount per capsule (mg) | Amount (% w/w) | Function | Standard |
|---|---|---|---|---|
| Capsule contents | | | | |
| Compound 1 | 50.0 | 10.0 | Active | AstraZeneca |
| Lauroyl macrogolglyceride (Lauroyl polyoxylglyceride)[a] | 450.0 | 90.0 | Excipient, pharmaceutical aid | PhEur (NF[c]) |

TABLE 7-continued

Quantitative composition of Compound 1 50 mg capsules

| Constituent | Amount per capsule (mg) | Amount (% w/w) | Function | Standard |
|---|---|---|---|---|
| Capsule | | | | |
| Hypromellose capsule shell[b] | Size 0 | Each unit | Dosage form presentation | USP, Ph Eur |
| Titanium dioxide | 1.84 | Each unit | Opacifier | |
| Opacode black ink (S-1-7822/S-1-7823) | 0.0332 | Each unit | | |

[a]Supplied as Gelucire 44/14 grade.
[b]Supplied as Capsugel V Cap capsules

4.3.2 Method of Preparation

The lauroyl macrogolglyceride (lauroyl polyoxylglyceride) was melted at about 50-70° C. then weighed into a stainless steel vessel. Crystalline Compound 1 was added and the contents mixed to achieve a homogeneous suspension. Mixing was continued while the mixture was dispensed into capsules to a fill weight of 500 mg per capsule using a thermostatically-controlled automated capsule filling machine.

4.4 In Vitro Dissolution of Compound 1 Preparations

4.4.1 Test Method

Dissolution was performed according to the general procedure of the United States Pharmacopeia Apparatus I (Basket). An amount of material containing approximately 100 mg of Compound 1 was weighed accurately then transferred to a dissolution vessel containing 500 mL of TRIS buffer (0.05M tris(hydroxymethyl)aminomethane solution adjusted to pH 7.2 with hydrochloric acid) maintained at 37° C. and stirred at 100 rpm. After 15, 30, 45 and 60 minutes, 10 mL samples were withdrawn and filtered through 0.2 µm PVDF filters. Compound 1 concentration in the filtrate was determined by ultraviolet spectroscopy at a wavelength of 278 nm.

4.4.2 Results

TABLE 8

In vitro dissolution of Compound 1 preparations

| Sample | Dissolution (% Release) | | | | | | | |
|---|---|---|---|---|---|---|---|---|
| | 15 min | 30 min | 45 min | 60 min | 75 min | 90 min | 105 min | 120 min |
| Drug only | 15 | 28 | 43 | 51 | 58 | 62 | 68 | 71 |
| Tablet | 72 | 81 | 85 | 87 | 89 | 90 | 91 | 92 |
| Microsuspension | 70 | 75 | 77 | 78 | 79 | 79 | 80 | 80 |
| Gelucire capsule (10% drug loading) | 37 | 92 | 97 | 99 | 99 | 100 | 100 | 100 |

Figure 2:
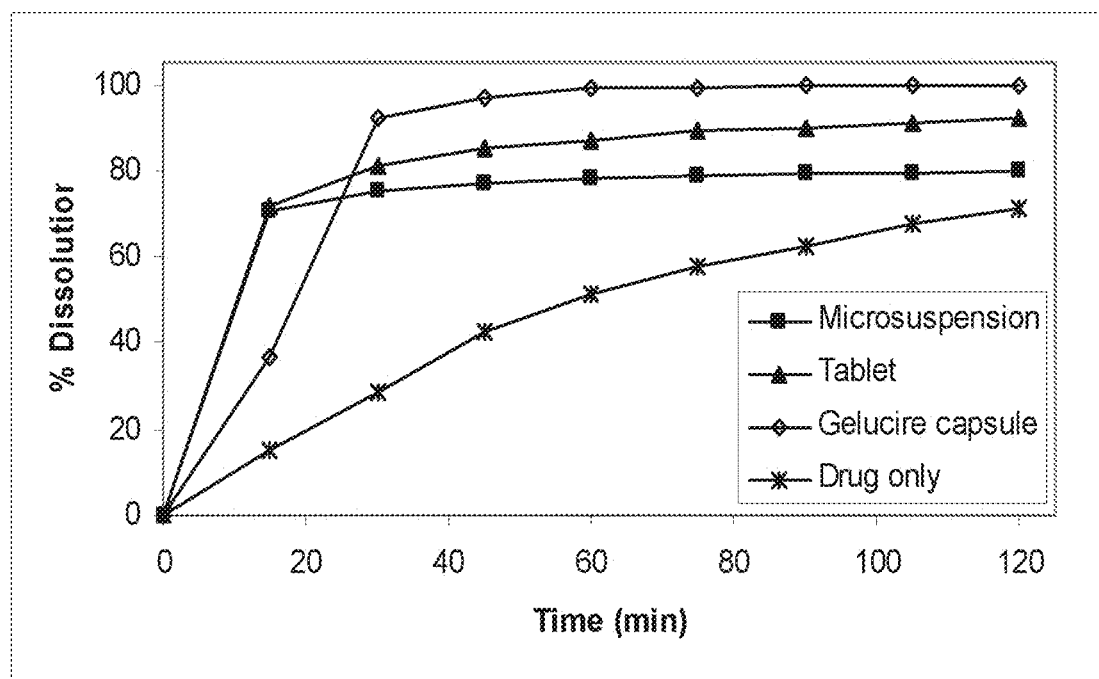
FIG. 2 shows in vitro dissolution of various Compound 1 formulations.

See FIG. 2.

4.5 Nanosuspension

4.5.1 Method of Preparation

Compound 1 was mixed with a few drops of vehicle (0.5% HPMC/0.1% Tween80) in a glass vial and "vortex" mixed for 1 minute, to wet and disperse the compound and to form a free flowing slurry. A further volume of vehicle was added to the slurry to produce a drug concentration of 50 mg/ml and the resulting slurry was then "vortex" mixed for approximately 1 minute to mix. The slurry at 50 mg/ml drug concentration was transferred to a zirconia milling pot. Zirconia milling beads (0.6-0.8 mm diameter) were added to the pot until the level of beads and slurry was equal. The pot was then sealed with a Teflon ring and lid (zirconia) and placed on a Fritsch P7 planetary mill. A second pot (as counter weight) was then placed on the mill. The pots were rotated on the mill at 800 rpm for 4×30 minutes runs (with 10 minutes between each run). The pots were then allowed to cool for a further 15 minutes and a sample of the resulting bead milled suspension taken for analysis. The nanosuspension was then separated from the milling beads, and diluted to a concentration of 10 mg/ml, ready for dosing. Nanosuspension particle size was measured using Fibre Optic Quasi Elastic Light Scattering (FOQUELS) from Brookhaven Instruments—laser wavelength of 635 nm. A mean effective diameter of 692+/−8 nm was measured. X-ray diffraction confirmed that the drug was essentially crystalline.

4.6 Solid Dispersion 4.6.1 Preparation by Solvent Evaporation Process

Solid dispersions having a 1:3 ratio by weight of Compound 1:polymer were prepared as follows:

0.75 g of Compound 1, prepared according to Example 9 [compound 168] in WO 2004/080976, and 2.25 g of polymer were weighed directly into a 250 ml round bottom flask and dissolved in 75 ml of methanol:dichloromethane (1:1). The solvent was removed on a rotary evaporator. The formulation was placed in a vacuum oven and dried under high vacuum at 40° C. overnight.

The formulation was retrieved from the flask and dry milled if necessary using a pestle and mortar. The formulation was then stored in a vacuum desiccator until needed.

In order to produce formulations having ratios other than 1:3, weights and volumes in the process were adjusted pro-rata to those described above.

4.6.2 Preparation by Melt Extrusion Process

Compound 1 was blended with polymer and glidant in the proportions defined in the manufacturing formula. The blend was extruded in a twin-screw extruder. During extrusion, a vacuum was applied to the extruder barrel to degas the melt. The extrudate was calendered by passing through two contra-rotating calender rollers, and then cooled prior to milling.

4.6.3 Stability Study 4.6.3.1 Protocol

Solid dispersions were prepared using the solvent evaporation process described previously (see 4.6.1), and amorphous Compound 1 was prepared according to Example 9 [compound 168] in WO 2004/080976. Samples were stored in closed HDPE bottles with polyethylene liners, with desiccant, for a period of 3 months under refrigeration (2-8° C.), long-term conditions (25° C./60% relative humidity) and accelerated conditions (40° C./75% relative humidity). In addition, samples were stored for a period of 1 month in an open petri dish at 40° C./75% relative humidity. Samples were tested prior to set-down, after 1 month and, for the samples in closed containers under long-term and accelerated conditions only, after 3 months.

4.6.3.2 Methodology

Dissolution

Dissolution was carried out in accordance with the general procedure of the United States Pharmacopeia using Apparatus II (paddle method). An amount of the solid dispersion containing about 100 mg of Compound 1 was weighed accurately then placed in 500 mL pH6.5 phosphate buffer at a temperature of 37° C. and a stirring speed of 75 rpm. After 5, 10, 20 and 45 minutes a 2 mL sample was removed and the Compound 1 content determined by HPLC.

TABLE 9

Chromatographic conditions for in vitro dissolution test

| Apparatus | Liquid chromatograph with UV detector |
|---|---|
| Column | Waters Sunfire C18, 4.6 mm × 50 mm (3.5 μm or equivalent) |
| Eluents | Eluent A: 0.1% TFA in water |
| | Eluent B: 0.1% TFA in acetonitrile |

| Gradient program | Time (min) | % A | % B |
|---|---|---|---|
| | 0 | 65 | 35 |
| | 0.8 | 65 | 35 |
| | 0.81 | 5 | 95 |
| | 1.8 | 5 | 95 |
| | 1.81 | 65 | 35 |
| | 3.5 | 65 | 35 |

| Flow rate | 1 mL/min approx. |
|---|---|
| Temperature | 35° C. |
| Wavelength | 276 nm |
| Injection volume | 10 μL |
| Run time | 3.5 min. |
| Compound 1 retention time | 1 min approx. |

Determination of Crystallinity by Differential Scanning Calorimetry

The sample was heated in a differential scanning calorimeter (TA Instruments Q1000) using a programme designed to drive off any water and/or solvents present, before cooling the sample and heating at a constant rate over a temperature range encompassing the melting transition of any crystalline material which may be present (Compound 1 Tm=210° C.) (see FIG. 3).

TABLE 10

Parameters for differential scanning calorimetry

| General parameters | |
|---|---|
| Sample weight (mg) | 2-10 |
| Pan type | Aluminium, pierced |
| Atmosphere | Nitrogen, 20-30 mL/min |
| Temperature programme | |
| Equilibration (30 minutes) | 30° C. |
| Cool to | 0° C. |
| Heat at 5° C./min | 120° C. |
| Cool | 0° C. |
| Heat at 5° C./min | 235° C. |
| Cool | |

4.6.3.3 Results

TABLE 11

Results for the stability study of Compound 1 polymeric dispersions

| | 2-8° C. | | 25° C./60% RH | | | | 40° C./75% RH | | | | | |
| | Closed | | Closed | | | | Closed | | | | Open | |
| | Initial | | 1 month | | 1 month | | 3 months | | 1 month | | 3 months | | 1 month | |
| Formulation | Diss | DSC | Diss | DSC | Diss | DSC | Diss | DSC | Diss | DSC | Diss | DSC | Diss | DSC |
|---|---|---|---|---|---|---|---|---|---|---|---|---|---|---|
| Kleptose 1:3 | 90 | N/D | 88 | N/D | 91 | N/D | 92 | N/D | 87 | N/D | 84 | N/D | NT | N/D |
| PVP 1:3 | 92 | N/D | 91 | N/D | 91 | N/D | 94 | N/D | 90 | N/D | 66 | X | NT | X |
| Amorphous Compound 1 | NT | N/D | NT | X | NT | X | NT | X | NT | X | NT | X | NT | X |
| Kleptose 1:2 | 81 | NT | 82 | N/D | 82 | N/D | X | N/D | 76 | N/D | 66 | N/D | 81 | N/D |
| PVP 1:2 | 81 | N/D | 81 | N/D | 77 | N/D | 86 | N/D | 85 | N/D | 55 | N/D | NT | X |
| HPMCP 1:3 | 99 | N/D | 91 | N/D | 90 | N/D | 87 | N/D | 87 | N/D | 83 | N/D | 91 | N/D |
| HPMCP 1:2 | 97 | N/D | 98 | N/D | 97 | N/D | 92 | N/D | 91 | N/D | 89 | N/D | 92 | N/D |

Key:
N/D = not detected
N/T = not tested
Diss = Dissolution (cumulative release) at 45 minutes, %
DSC = Crystallinity as determined by differential scanning calorimetry The results of the stability study demonstrate that solid dispersions produced using the relatively hygroscopic polymer povidone tended to crystallise when stored at 40° C./75% relative humidity, leading to a reduction in dissolution rate. Solid dispersions produced using 2-hydroxypropyl-β-cyclodextrin and hypromellose phthalate were stable under all tested conditions.

4.7. Copovidone Solid Dispersion (Uncoated Tablet Formulation)

4.7.1 Formulation

TABLE 12

Composition of Compound 1/copovidone solid dispersion uncoated tablet

| Components | Quantity (mg) | Quantity (%) | Function | Standard |
|---|---|---|---|---|
| Compound 1 | 200.00 | 25.00 | Active pharmaceutical ingredient | AstraZeneca |
| Copovidone | 460.00 | 57.50 | Polymeric carrier | NF and Ph Eur |
| Colloidal silicon dioxide | 14.64 | 1.83 | Glidant | NF and Ph Eur |
| Mannitol | 117.36 | 14.67 | Soluble filler | NF and Ph Eur |
| Sodium stearyl fumarate | 8.00 | 1.00 | Lubricant | NF and Ph Eur |
| Core tablet weight | 800.00 | | | |

4.7.2 Method of Preparation

A solid dispersion of Compound 1 and copovidone was prepared using the melt extrusion process described in 4.6.2. The milled extrudate was mixed with the external excipients and compressed into tablet form using a single punch hand press to achieve hardness in the range 80-100 N.

4.7.3 Stability Study—Uncoated Tablets 4.7.3.1 Protocol

Uncoated tablets prepared as described in 4.7.2 were stored in closed HDPE bottles with polyethylene liners, with desiccant, for a period of 4 months under long-term conditions (25° C./60% relative humidity) and accelerated conditions (40° C./75% relative humidity). Samples were tested prior to set-down, then after 1, 3 and 4 months.

4.7.3.2 In Vitro Evaluation

Crystallinity was determined by DSC as described in 4.6.3.2.

Dissolution Test

The dissolution method was adapted from that previously described for solid dispersion formulations (see 4.6.3.2). Dissolution was carried out in accordance with the general procedure of the United States Pharmacopeia using Apparatus II (paddle method). Individual dosage units were placed in 1000 mL of pH6.5 phosphate buffer at a temperature of 37° C. and a stirring speed of 75 rpm. After 15, 30, 60, 90, 120 and 180 minutes a 1 mL sample was removed and the Compound 1 content determined by HPLC:

TABLE 13

Chromatographic conditions for in vitro dissolution test for Compound 1/copovidone solid dispersion tablet

| Chromatographic conditions | | | |
|---|---|---|---|
| Apparatus | Liquid chromatograph with UV detector | | |
| Column | Waters Sunfire C18, 4.6 mm × 50 mm (3.5 μm or equivalent) | | |
| Eluents | Eluent A: 0.1% TFA in water | | |
| | Eluent B: 0.1% TFA in acetonitrile | | |
| Gradient program | Time (min) | % A | % B |
| | 0 | 75 | 25 |
| | 3.0 | 55 | 45 |
| | 3.5 | 0 | 100 |
| | 4.0 | 0 | 100 |
| | 7.0 | 75 | 25 |
| Flow rate | 1 mL/min approx. | | |
| Temperature | 40° C. | | |
| Wavelength | 276 nm | | |
| Injection volume | 10 μL | | |
| Run time | 7 min. | | |
| Compound 1 retention time | 2.9 min approx. | | |

Compound 1 Assay and Impurities by HPLC

The Compound 1 and total impurities contents were determined using High Performance Liquid Chromatography (HPLC). A sample solution was prepared containing approximately 0.4 mg/mL Compound 1, using 50:50 v/v acetonitrile/water as diluent. The sample solution was filtered using a 0.2 μm PVDF filter prior to analysis.

10 µL sample was injected into a mobile phase comprising 0.05% trifluoroacetic acid (TFA) in water (Eluent A)/0.05% TFA in acetonitrile (Eluent B), as defined by the gradient program in Table 14 below.

TABLE 14

Gradient programme - Compound 1 assay and impurities

| Gradient programme | Time mins) | % A | % B |
|---|---|---|---|
| | 0 | 90 | 10 |
| | 20 | 60 | 40 |
| | 28 | 5 | 95 |
| | 30 | 5 | 95 |
| | 30.1 | 90 | 10 |
| | 36 | 90 | 10 |

The mobile phase starts as defined at time zero, then the composition is modified by adjusting the proportion of eluents A and B gradually and linearly to the composition at each successive time-point.

Separation of impurities was performed using a column 15 cm long×4.6 mm internal diameter packed with Waters Sunfire C18 stationary phase having 3.5 µm particle size. The mobile phase flow rate was 1.0 mL/minute, temperature was controlled at 30° C., and impurity concentration was determined by comparison of absorbance at 276 nm, measured using a variable wavelength uv detector, with that of an external Compound 1 reference standard.

Water Content by Coulometric Karl Fischer Titration

Water content was determined by coulometric Karl Fischer titration using a Metrohm 684 Coulometer. Samples were ball milled prior to analysis and measurements were performed using a sample size of 200 mg.

4.7.3.3 Results 4.8. Copovidone Solid Dispersion (Film-Coated Tablet Formulation)

4.8.1 Formulation

TABLE 16

Composition of Compound 1/copovidone solid dispersion tablet

| Tablet core Components | Quantity (mg per tablet) | | Quantity (% core weight) | Function |
|---|---|---|---|---|
| | 25 mg tablet | 100 mg tablet | | |
| Compound 1 | 25.00 | 100.00 | 25.00 | Active pharmaceutical ingredient |
| Copovidone | 57.50 | 230.00 | 57.50 | Polymeric carrier |
| Colloidal silicon dioxide | 1.83 | 7.33 | 1.83 | Glidant |
| Mannitol | 14.67 | 58.67 | 14.67 | Soluble filler |
| Sodium stearyl fumarate | 1.00 | 4.00 | 1.00 | Lubricant |
| Core tablet weight | 100.00 | 400.00 | | |
| Tablet Coating | | | | |
| Hypromellose (HPMC 2910) | 2.19 | 8.75 | 62.5 | Film former |
| Titanium dioxide (E171) | 0.88 | 3.51 | 25.05 | Opacifier |
| Macrogol / PEG 400 | 0.22 | 0.88 | 6.25 | Plasticiser |
| Iron oxide yellow (E172) | 0.16 | 0.64 | 4.55 | Colouring agent |
| Iron oxide black (E172) | 0.06 | 0.23 | 1.65 | Colouring agent |
| Nominal Coating Weight | 3.50 | 14.00 | 3.50 | |

TABLE 15

Results of the stability study for Compound 1/copovidone solid dispersion tablet (200 mg, uncoated))

| | Initial | | 25° C./60% Relative Humidity | | | | | | 40° C./75% Relative Humidity | | | | | |
|---|---|---|---|---|---|---|---|---|---|---|---|---|---|---|
| | | | 1 month | | 3 months | | 4 months | | 1 month | | 3 months | | 4 months | |
| Crystallinity by DSC | N/D | | N/D | | N/D | | N/D | | N/D | | N/D | | N/D | |
| Dissolution (Time-point) | $X^1$ | $S^2$ | $X^1$ | $S^2$ | $X^1$ | $S^2$ | $X^1$ | $S^2$ | $X^1$ | $S^2$ | $X^1$ | $S^2$ | $X^1$ | $S^2$ |
| (15 min) | 14 | 3 | 15 | 2 | 19 | 7 | 20 | 5 | 17 | 2 | 14 | 1 | 17 | 2 |
| (30 min) | 32 | 5 | 33 | 3 | 41 | 15 | 45 | 10 | 38 | 2 | 33 | 3 | 37 | 4 |
| (60 min) | 60 | 8 | 62 | 4 | 68 | 13 | 81 | 15 | 70 | 2 | 62 | 7 | 68 | 5 |
| (90 min) | 77 | 5 | 82 | 8 | 85 | 6 | 96 | 7 | 88 | 3 | 80 | 7 | 85 | 2 |
| (120 min) | 84 | 2 | 89 | 6 | 92 | 3 | 100 | 4 | 93 | 5 | 88 | 5 | 91 | 2 |
| (180 min) | 87 | 1 | 91 | 4 | 93 | 1 | NT | | 95 | 4 | 91 | 4 | 94 | 1 |
| Water content (% w/w) | 1.3 | | 1.3 | | 1.6 | | 1.3 | | 1.4 | | 1.7 | | 1.8 | |
| Assay (%) | 99.6 | | 98.6 | | 101.1 | | 98.1 | | 100.4 | | 100.5 | | 100.1 | |
| Impurities (%) | 0.44 | | 0.44 | | 0.44 | | 0.43 | | 0.44 | | 0.44 | | 0.44 | |

[1]X is the mean % release (n = 3)

[2]S is the standard deviation (n = 3)

4.8.2 Method of Preparation

Compound 1 was blended with polymer and glidant in the proportions defined in the manufacturing formula. The blend was extruded in a twin-screw extruder. During extrusion, a vacuum was applied to the extruder barrel to degas the melt. The extrudate was calendered by passing through two contra-rotating calender rollers, and then cooled prior to milling. The extrudate was milled and subsequently mixed with the external excipients. The powder blend was compressed into tablet cores using a Rotary Press (Korsch XL 100 with 10 punch stations) to achieve a sufficient hardness (minimum 25 N).

The tablet cores were coated using a Driacoater Driam 600 coater with Opadry™ Green (Colorcon 03B21726, 130 g/Kg aqueous solution). The total coating solution applied is equivalent to 35 g of Opadry™ per Kg of tablet cores.

4.8.3 Stability Study—Film-Coated Tablets

4.8.3.1 Protocol

Film-coated tablets prepared as described in 4.8.2 were stored in closed HDPE bottles with polyethylene liners, with desiccant, for a period of 4 months under long-term conditions (25° C./60% relative humidity) and accelerated conditions (40° C./75% relative humidity). Samples were tested prior to set-down, then after 1 month 3 and 4 months.

4.8.3.2 In Vitro Evaluation

Water content, assay and impurities were determined using the methods described in Section 4.7.3.2.

Determination of Crystallinity by Hot-Stage Microscopy

Figure 4:
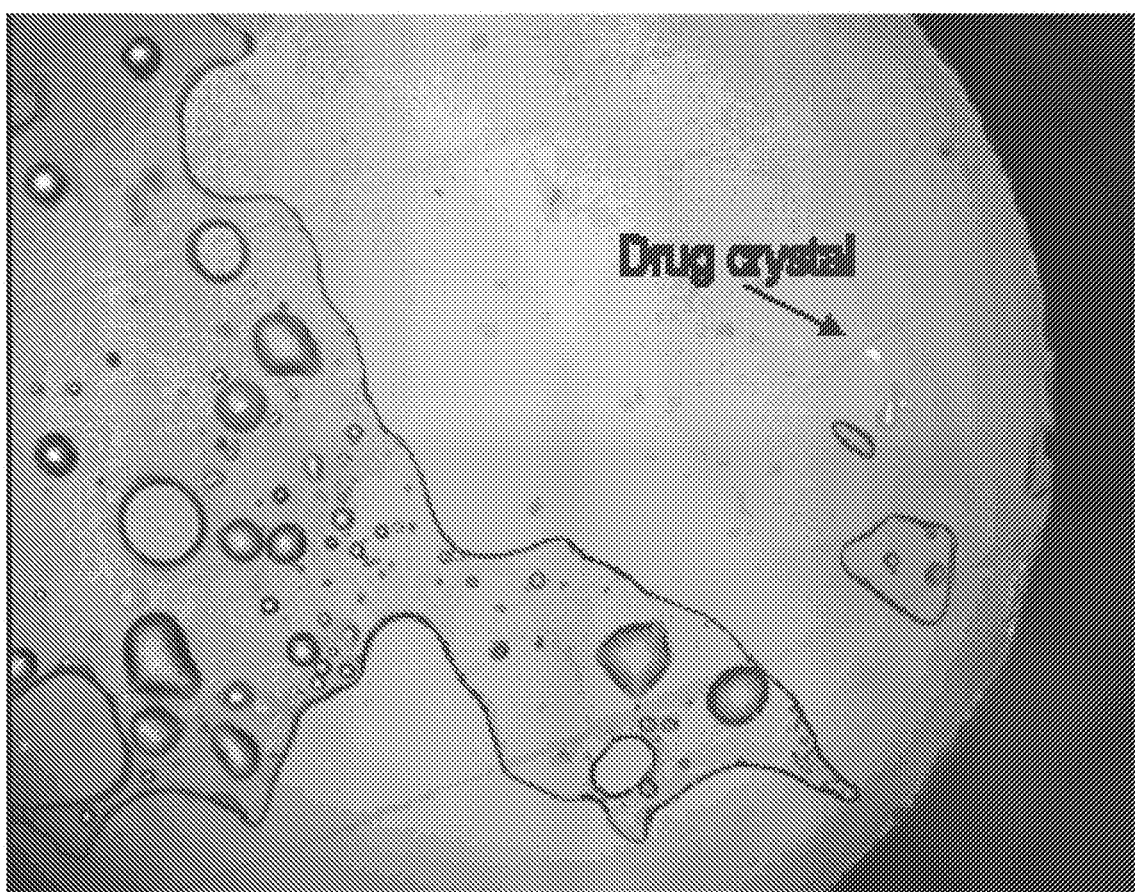
FIG. 4 shows an image of a tablet which exhibits a single crystal of Compound 1 in the hot-stage microscopy method

Ground tablets were examined by optical microscopy under cross-polarising conditions whilst being heated steadily across the melting point range of the excipients and Compound 1 to detect the presence of drug crystals. Any particles seen to be birefringent between 180° C. and 190° C. which subsequently melted at approximately 210° C. were classified as Compound 1. See FIG. 4 for an example of a drug crystal as seen under the microscope.

Dissolution Test

The dissolution method was adapted from that previously described for uncoated tablet formulations (see 4.7.3.2). Dissolution was carried out in accordance with the general procedure of the United States Pharmacopeia using Apparatus I (basket method). Individual dosage units were placed in 900 mL 0.3% SDS at a temperature of 37° C. and a stirring speed of 100 rpm. After 15, 30, 45, 60 and 90 minutes a sample was removed and the Compound 1 content determined by HPLC:

TABLE 17

Chromatographic conditions for in vitro dissolution test for Compound 1/copovidone solid dispersion tablet

| Chromatographic conditions | | | |
|---|---|---|---|
| Apparatus | Liquid chromatograph with UV detector | | |
| Column | Waters Symmetry C18, 4.6 mm × 75 mm × 3.5 µm | | |
| Eluents | Eluent A: 0.1% TFA in water<br>Eluent B: 0.1% TFA in acetonitrile | | |
| Gradient program | Time (min) | % A | % B |
| | 0 | 75 | 25 |
| | 3.0 | 55 | 45 |
| | 3.5 | 0 | 100 |
| | 7.0 | 75 | 25 |
| Flow rate | 1 mL/min approx. | | |
| Temperature | 40° C. | | |
| Wavelength | 276 nm | | |
| Injection volume | 10 µL | | |
| Run time | 7 min | | |
| Compound 1 retention time | 2.9 min approx. | | |

4.8.3.3 Results

TABLE 18

Results of the stability study for Compound 1/copovidone film-coated solid dispersion tablet (25 mg)

| | | | 25° C./60% Relative Humidity | | | | | | 40° C./75% Relative Humidity | | | | | |
|---|---|---|---|---|---|---|---|---|---|---|---|---|---|---|
| | | Initial | 4 weeks | | 13 weeks | | 26 weeks | | 4 weeks | | 13 weeks | | 26 weeks | |
| Crystallinity:<br>Hot-Stage Microscopy | | D (+) | N/D | | D (++) | | D (+++) | | N/D | | D (++) | | D (+++) | |
| Wide-Angle X-Ray Scattering | | N/D | N/T | | N/D | | N/D | | N/T | | N/D | | N/D | |
| Dissolution | (Time-point) | X¹ S² | X¹ | S² | X¹ | S² | X¹ | S² | X¹ | S² | X¹ | S² | X¹ | S² |
| | (15 min) | 41 3.6 | 38 | 3.2 | 41 | 3.8 | 41 | 2.9 | 39 | 2.8 | 41 | 2.1 | 39 | 3.5 |
| | (30 min) | 77 5.2 | 78 | 6.2 | 78 | 4.8 | 81 | 4.5 | 77 | 3.7 | 78 | 2.1 | 78 | 5.4 |
| | (45 min) | 98 3.9 | 99 | 3.5 | 99 | 3.4 | 102 | 2.3 | 98 | 3.9 | 98 | 1.4 | 101 | 2.4 |
| | (60 min) | 104 1.4 | 104 | 1.9 | 104 | 1.0 | 105 | 1.3 | 103 | 4.8 | 101 | 0.5 | 106 | 1.3 |
| | (90 min) | 104 1.1 | 104 | 1.4 | 104 | 1.0 | 105 | 1.5 | 103 | 4.5 | 101 | 0.4 | 106 | 1.0 |
| Water content (% w/w) | | 2.3 | 2.1 | | 2.2 | | 2.0 | | 1.9 | | 2.1 | | 2.2 | |
| Assay (%) | | 104.0 | 104.3 | | 103.5 | | 102.5 | | 102.0 | | 104.1 | | 106.0 | |
| Impurities (%) | | 0.52 | 0.51 | | 0.50 | | 0.50 | | 0.50 | | 0.50 | | 0.53 | |

Key:

N/D = not detected

D = detected; (+) 1-5 birefringent spots (++) 5-30 birefringent spots (+++) more than 30 birefringent spots N/T = not tested

[1]X is the mean % release (n = 3)

[2]S is the standard deviation (n = 3)

TABLE 19

Results of the stability study for Compound 1/copovidone film-coated solid dispersion tablet (100 mg)

|  |  | 25° C./60% Relative Humidity | | | 40° C./75% Relative Humidity | | |
| --- | --- | --- | --- | --- | --- | --- | --- |
| Crystallinity: | Initial | 4 weeks | 13 weeks | 26 weeks | 4 weeks | 13 weeks | 26 weeks |
| Hot-Stage Microscopy | D (+) | N/D | D (+++) | D (+++) | D (+) | D (+) | D (++) |
| Wide-Angle X-Ray Scattering | N/D | N/T | N/D | N/D | N/T | N/D | N/D |

| Dissolution (Time-point) | $X^1$ | $S^2$ | $X^1$ | $S^2$ | $X^1$ | $S^2$ | $X^1$ | $S^2$ | $X^1$ | $S^2$ | $X^1$ | $S^2$ | $X^1$ | $S^2$ |
| --- | --- | --- | --- | --- | --- | --- | --- | --- | --- | --- | --- | --- | --- | --- |
| (15 min) | 24 | 0.5 | 24 | 1.0 | 25 | 1.9 | 26 | 1.1 | 25 | 1.8 | 25 | 1.2 | 24 | 1.2 |
| (30 min) | 55 | 1.0 | 54 | 1.3 | 56 | 2.3 | 60 | 1.6 | 57 | 2.8 | 56 | 2.1 | 56 | 1.9 |
| (45 min) | 80 | 1.6 | 80 | 1.6 | 81 | 1.9 | 87 | 1.5 | 83 | 3.1 | 81 | 2.1 | 83 | 2.1 |
| (60 min) | 97 | 1.0 | 97 | 1.1 | 98 | 1.7 | 102 | 0.5 | 99 | 2.1 | 97 | 2.1 | 99 | 1.2 |
| (90 min) | 101 | 0.8 | 101 | 0.5 | 102 | 0.8 | 104 | 0.8 | 102 | 1.0 | 101 | 0.8 | 102 | 0.5 |
| Water content (% w/w) | 2.0 | | 1.7 | | 2.5 | | 1.6 | | 1.8 | | 2.2 | | 1.5 | |
| Assay (%) | 102.5 | | 100.5 | | 102.8 | | 102.2 | | 103.6 | | 100.8 | | 102.1 | |
| Impurities (%) | 0.50 | | 0.49 | | 0.50 | | 0.50 | | 0.51 | | 0.49 | | 0.50 | |

Key:
N/D = not detected
D = detected; (+) 1-5 birefringent spots (++) 5-30 birefringent spots (+++) more than 30 birefringent spots
N/T = not tested
[1] X is the mean % release (n = 3)
[2] S is the standard deviation (n = 3)

EXAMPLE 5 NANOMETER-SCALE CHARACTERISATION STUDIES 5.1 Solid State Nuclear Magnetic Resonance Study Solid dispersions of Compound 1 and copovidone, prepared with drug loadings of 10, 25, 35 and 40% using the melt extrusion process described in 4.6.2, were evaluated by solid state nuclear magnetic resonance spectroscopy (SSNMR) using methodology disclosed in Asano, A; Takegoshi, K.; Hikichi, K. Polymer (1994), 35(26), 5630-6. $^{13}$C cross-polarisation magic angle spinning SSNMR spectra were recorded at 100 MHz with a spin rate of 9 kHz using a Bruker Avance 400WB with a 4 mm HFX MAS probe. For each sample, with different drug loading, a series of spectra were acquired with different contact times ranging from 500 µs to 10 ms. Peak areas from different spectral regions were measured. These areas were selected to contain peaks corresponding to Compound 1 or copovidone. With increasing contact time peak area increases to a maximum value and then decays due to a process known as proton spin diffusion. This decay is characterised by a constant $T_{1\rho}$, which represents proton spin-lattice relaxation in the rotating frame of reference. For a phase-separated system, on a length scale longer than the spin-diffusion length scale, the relaxation rates for this decay process are identical to those observed for the individual components. For a mixed system, a single value of $T_{1\rho}$ is observed as a weighted average of the individual components.

For the samples with Compound 1 loading between 10 & 40% each magnetization decay could be fitted to a single exponential function with very similar $T_{1\rho}$ values observed. This suggests a similar relaxation pathway for the drug and polymer and infers a single phase.

TABLE 20

Results of the Solid State NMR study

| | $T_{1\rho}$/ms | |
| --- | --- | --- |
| Compound 1 loading | Peaks due to Compound 1 (119.5-140.0 ppm) | Peaks due to co-povidone (167.0-183.0 ppm) |
| 40% | 9.9 | 9.7 |
| 35% | 10.2 | 9.4 |

TABLE 20-continued

Results of the Solid State NMR study

| | $T_{1\rho}$/ms | |
| --- | --- | --- |
| Compound 1 loading | Peaks due to Compound 1 (119.5-140.0 ppm) | Peaks due to co-povidone (167.0-183.0 ppm) |
| 25% | 13.2 | 8.6 |
| 10% | 15.5 | 9.4 |

5.2 Pair-Wise Distribution Function Study

Solid dispersions of Compound 1 and copovidone, prepared with drug loadings of 10, 25, 35 and 40% using the melt extrusion process described in 4.6.2, were evaluated using X-ray powder diffraction and Pair-wise Distribution Functions (PDFs) were derived for each sample.

5.2.1 Data Collection

X-ray powder diffraction data were collected on the Bruker D8 diffractometer, which has a Copper source generating X-rays with a wavelength of 1.5418 Å (Göbel mirrors used to provide parallel beam optics remove the kβ leaving a beam with an average wavelength of kα1 and kα2) using a voltage of 40 kV and a filament emission of 40 mA. Samples were measured in reflection mode and the diffraction pattern collected using a scanning position-sensitive detector.

A diffractogram of the zero background wafer was obtained, under vacuum. 50 mg (+/−5 mg) of each sample was weighed out and dispersed onto a zero background holder, ensuring near complete coverage. The sample was added to the TTK chamber, which was then placed under vacuum to a pressure of <5×10-2 mbar. XRPD data were collected over approximately 20-30 minutes: data acquisition parameters of 4-80°2θ in steps of 0.007091° counting for 0.2 s/step were used for each sample.

A peak in the patterns at 6.6°2θ is caused by the sample holder and was removed in each case through subtraction of a blank run (i.e. an empty sample holder) which is measured on the day of the experiment.

5.2.2 Computational Methods—Pair-Wise Distribution Function

PDFs were calculated for each sample (S. J. L. Billinge and M. G. Kanatzidis, Chem. Commun., 2004, 749-760; S. Bates et. al., Pharmaceutical Research, 2006, 23(10) 2333-2349; S. Bates et. al., J. Pharmaceutical Sciences, 2007, 96(5), 1418-1433) The measured X-ray diffraction pattern (known as the scattering function) was transformed to a normalized scattering function S(Q) by carrying out a number of corrections to the data related to both the sample and experimental set-up. PDFs are then generated from the sine Fourier transformation of s(Q), equation 1.

$$G(r) = \frac{2}{\pi} \int_0^\infty Q[S(Q) - 1]\sin(Qr)dQ \quad \text{Equation 1}$$

Q is the magnitude of the scattering vector and is derived from $Q = 4\pi \sin(q)/\lambda$ The PDF is a plot of G(r) against interatomic distance and shows the probability of finding an atom at given distance 'r' from another atom. X-ray amorphous materials which are nanocrystalline possess long range ordering and thus the probability of finding an atom out at long distances is relatively high. In contrast, truly amorphous materials do not possess any long range ordering and the probability of finding an atom out at long distances is relatively low.

PDFs were generated from each of X-ray diffraction pattern measured using the software PDFgetX2 (X. Qui et. al., J. Appl. Cryst. 2004, 37, 678)

5.2.3 Results

Figure 5:
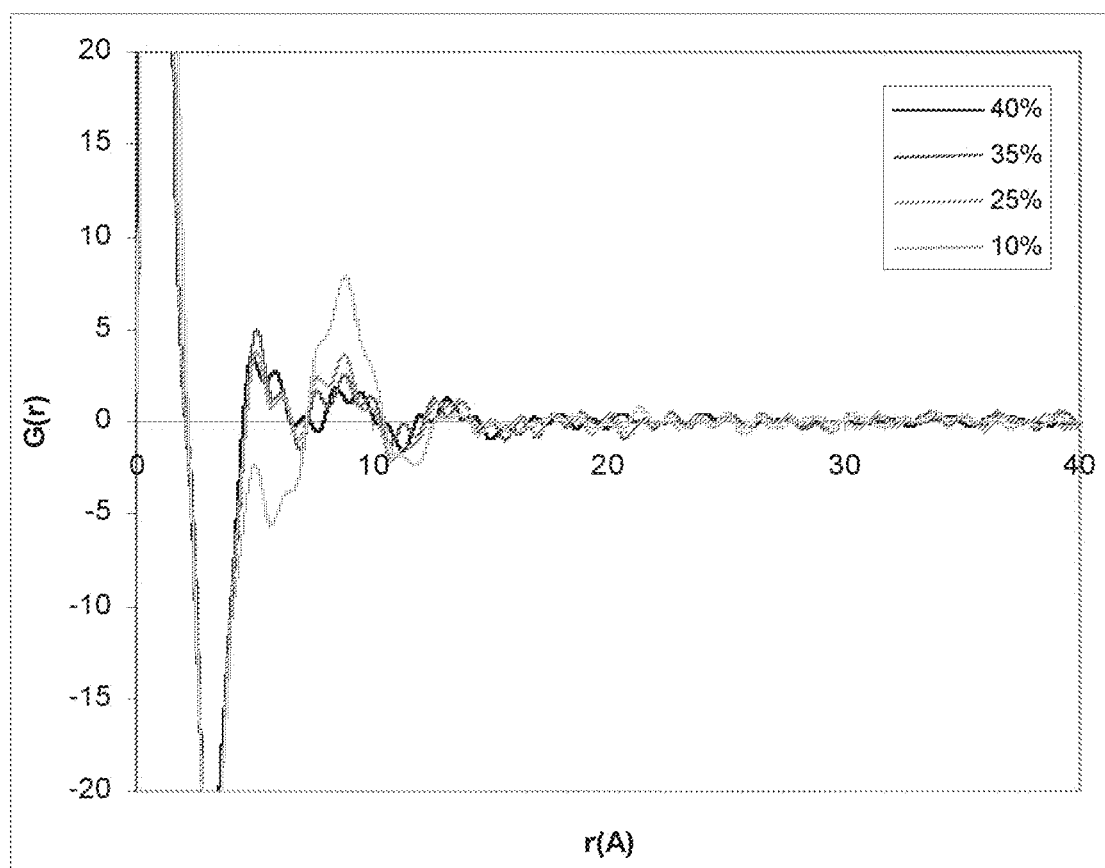
FIG. 5 shows PDF spectra for solid dispersions of Compound 1 and copovidone at various drug loadings

As shown in FIG. 5. there is little evidence of ordering beyond 15 Å for solid dispersions of Compound 1 and copovidone for any of the drug loadings investigated. This confirms that these solid dispersions are amorphous and do not exhibit significant long-range order.

5.2.4 Linear Combination of PDFs

5.2.4.1 Method

PDFs of the separate components of the formulation, amorphous Compound 1 and copovidone, were generated. These PDFs were then combined in the correct ratios (70% copovidone and 30% amorphous Compound 1) to give a simulated PDF trace for a physical mixture of the two. The traces obtained in 5.2.2. were compared to this simulated trace.

5.2.4.2 Results

Figure 6:
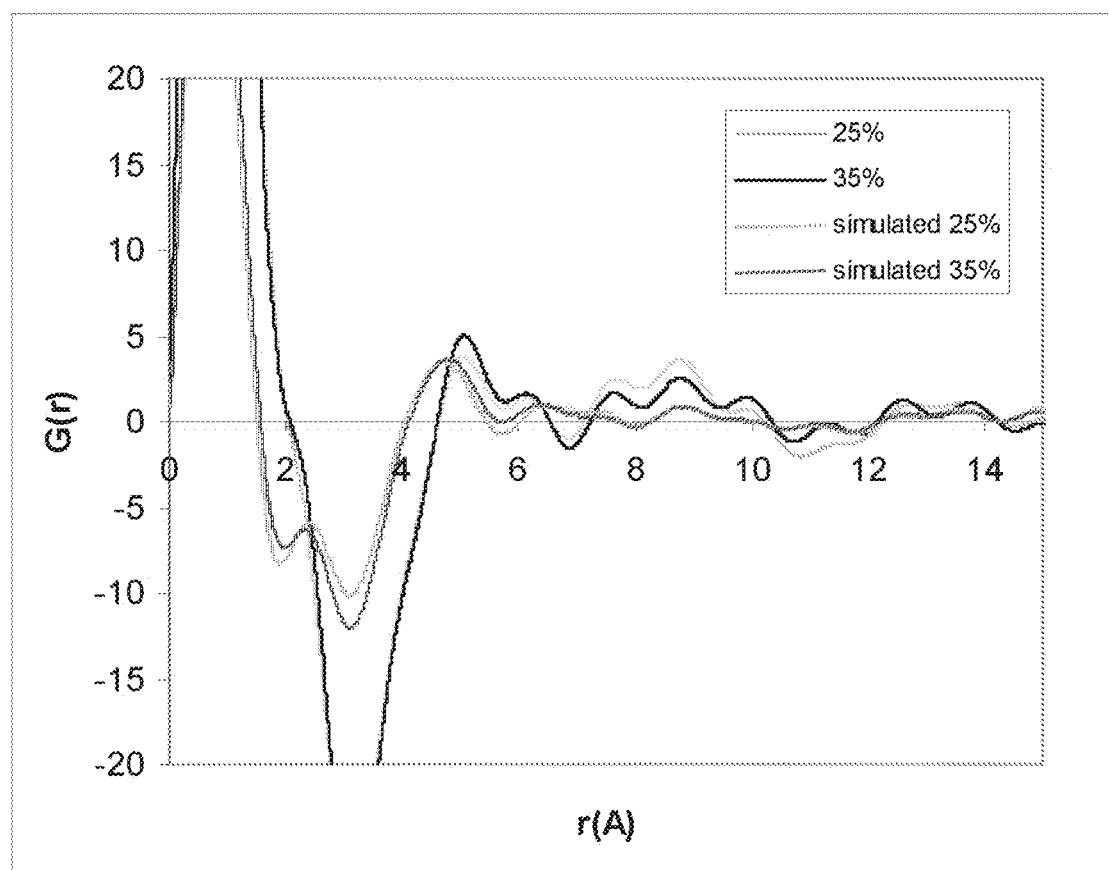
FIG. 6 shows a comparison of PDF spectra for solid dispersions of Compound 1 and copovidone with simulated spectra for physical mixtures at various drug loadings FIGS. 7(1)-7(6) show TM-AFM topographic (height), tip-deflection (error) and phase (mechanical property) images from 50 μm×50 μm and 10 μm×10 μm scans for solid dispersions of compound 1 and copovidone at 10% drug loading:—

As shown in FIG. 6, a physical mixture of amorphous Compound 1 and copovidone would exhibit a characteristic pattern between 1 and 5 Å, comprising dual minima for G(r) at approximately 2 Å and approximately 3 Å; solid dispersions of Compound 1 and copovidone exhibit a single accentuated minimum at approximately 3 Å. These data indicate that solid dispersions of Compound 1 and copovidone are true molecular dispersions.

5.3 Nano-Thermal Characterisation Study

Solid dispersions of Compound 1 and copovidone, prepared with drug loadings of 10, 30 and 40% using the melt extrusion process described in 4.6.2, were evaluated using Atomic Force Microscopy (Gan, Y. Surface Science Reports (2009), 64(3), 99-121; Fulghum, J. E.; McGuire, G. E.; Musselman, I. H.; Nemanich, R. J.; White, J. M.; Chopra, D. R.; Chourasia, A. R. Analytical Chemistry (1989), 61(12), 243R-69R) and using localised thermal analysis (Harding, L.; King, W. P.; Dai, X.; Craig, D. Q. M.; Reading, M. Pharmaceutical Research (2007), 24(11), 2048-2054.)

5.3.1 Methods

The work was carried out on a TA Instruments 2990 Micro-Thermal Analyzer based on a Veeco Explorer atomic force microscope. Preliminary imaging of the samples was carried out in Tapping Mode (TM-AFM) using Veeco 1660-00 high resonance frequency (HRF) silicon probes. Micro-thermal analysis (micro-TA) was carried out using Wollaston wire thermal probes. Nano-thermal analysis (nano-TA) was carried out using Anasys Instruments AN2-300 ThermaLever™ doped silicon probes controlled by an Anasys Instruments NanoTA1 AFM accessory. The Wollaston probe was temperature-calibrated using poly(ethylene) terephthalate (PET) film (melting temperature=240° C.) and room temperature. A 3-point temperature calibration was 'carried out for the ThermaLever probe using polycaprolactone (PCL, Tm=55° C.), HDPE (Tm=115° C.) and PET melting temperature standards. The calibration of each probe was checked before and after a sample was analysed. Unless stated otherwise, the heating rate used in all the localised thermal analysis runs was 20° C./s.

All the samples were analysed in the as-received state— i.e. the unmodified surface of the moulded pellets.

5.3.2 Results

Figure 7:
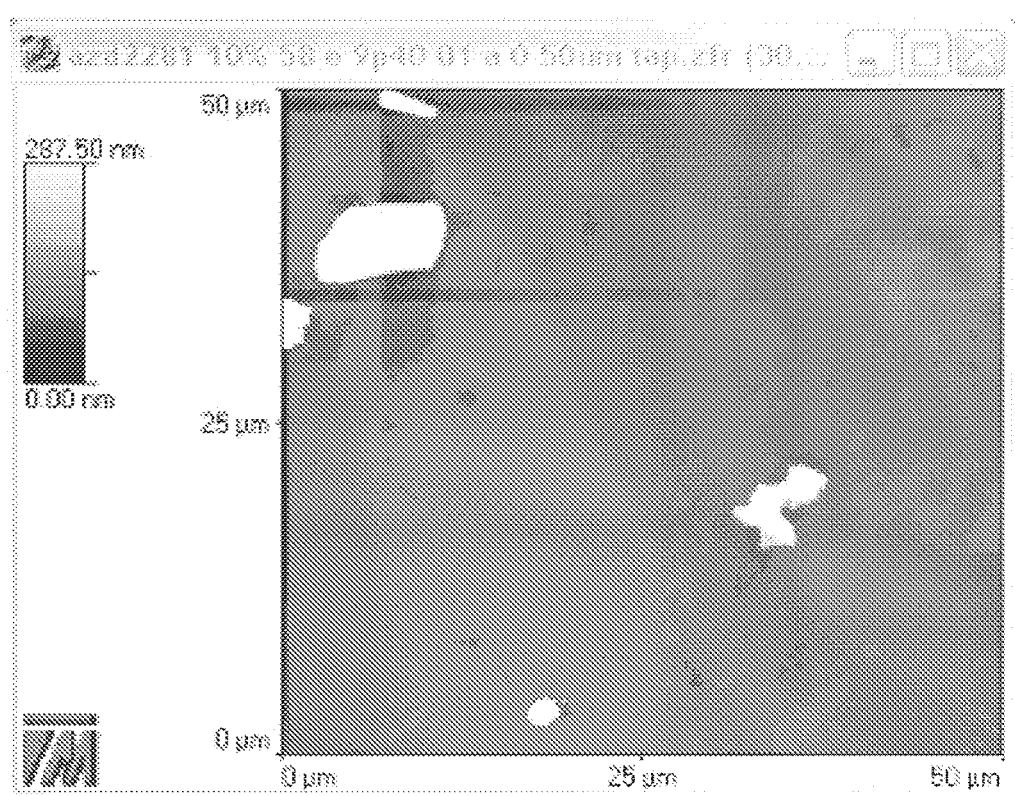
FIG. 7(1) is the 50 μm×50 μm topographic (height)
FIG. 7(2) is the 50 μm×50 μm tip-deflection (error)
FIG. 7(3) is the 50 μm×50 μm phase (mechanical property)
FIG. 7(4) is the 10 μm×10 μm topographic (height)
FIG. 7(5) is the 10 μm×10 μm tip-deflection (error)
FIG. 7(6) is the 10 μm×10 μm phase (mechanical property)
Figure 7:
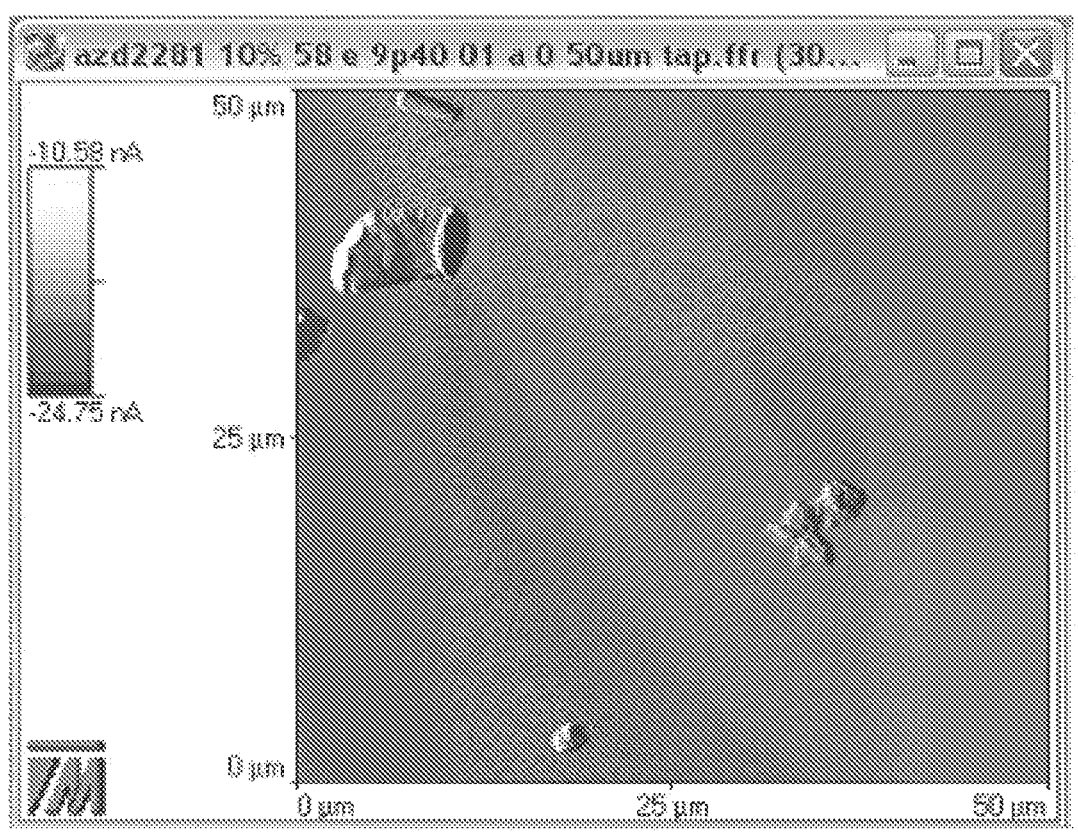
Figure 7:
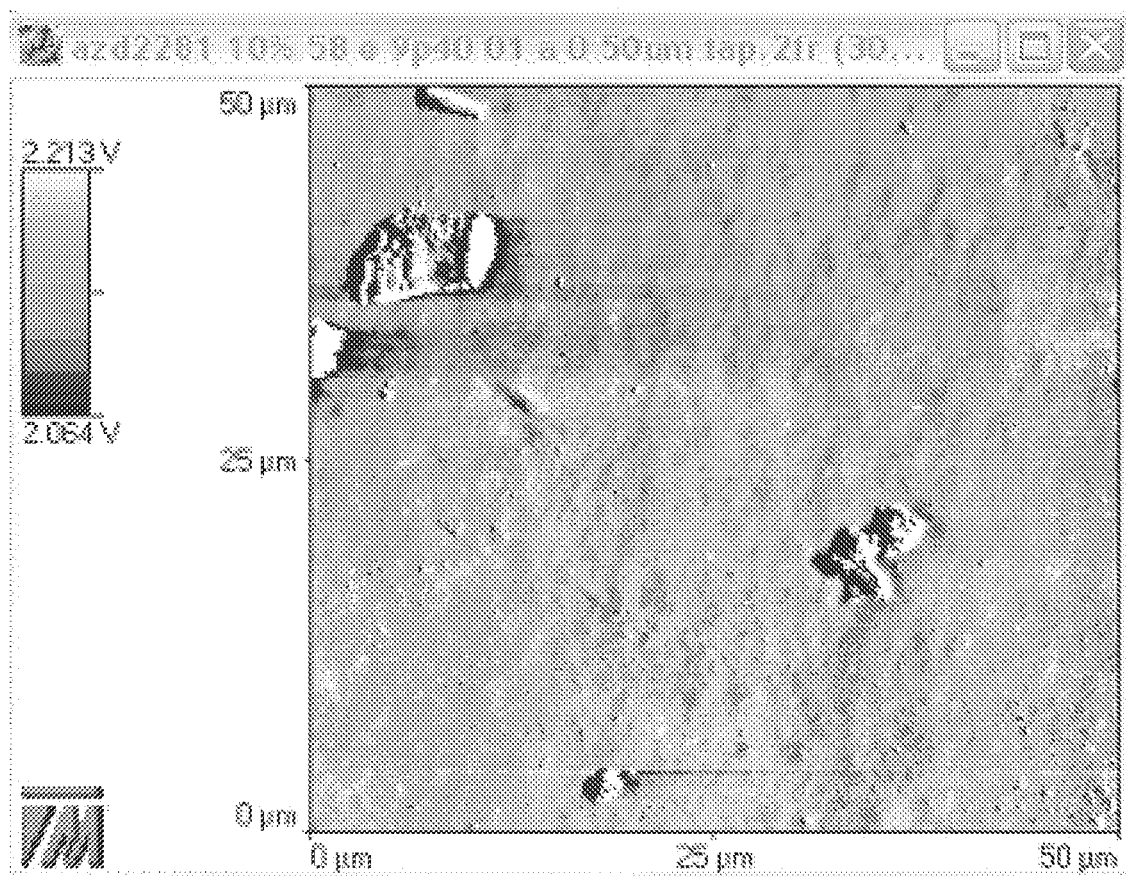
Figure 7:
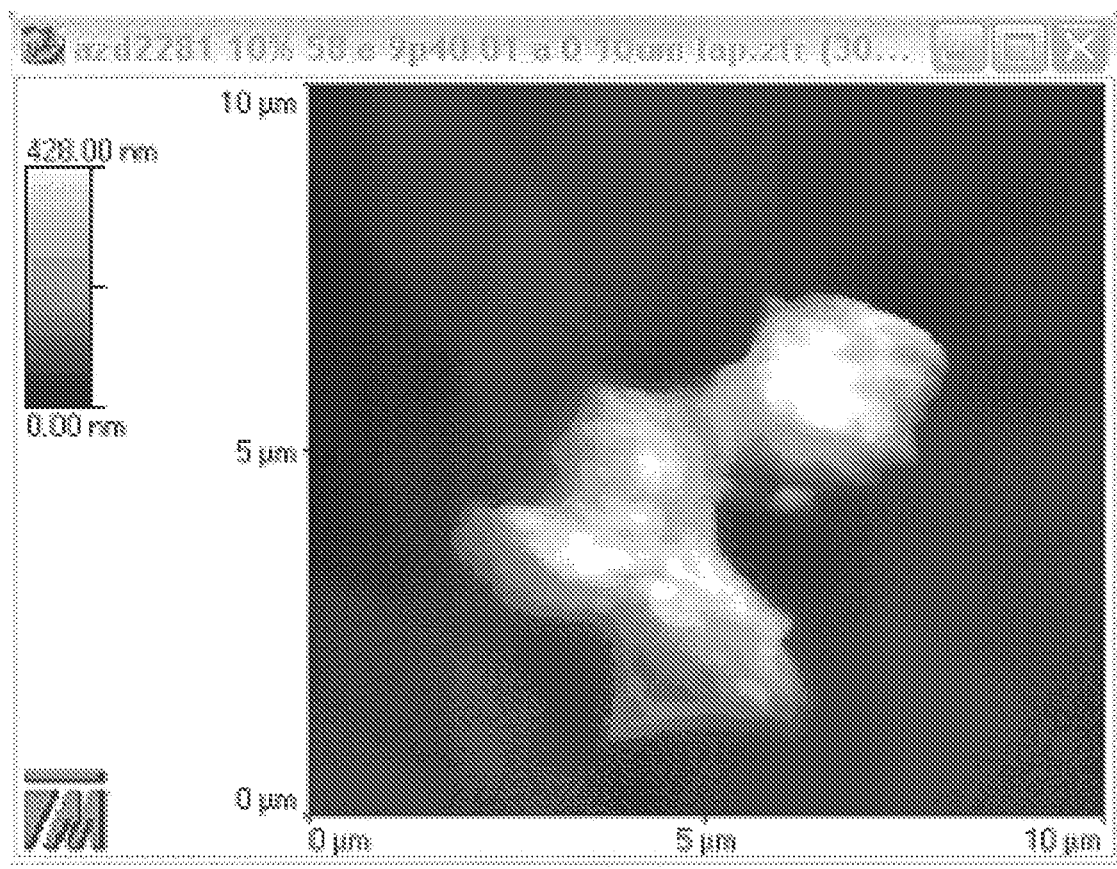
Figure 7:
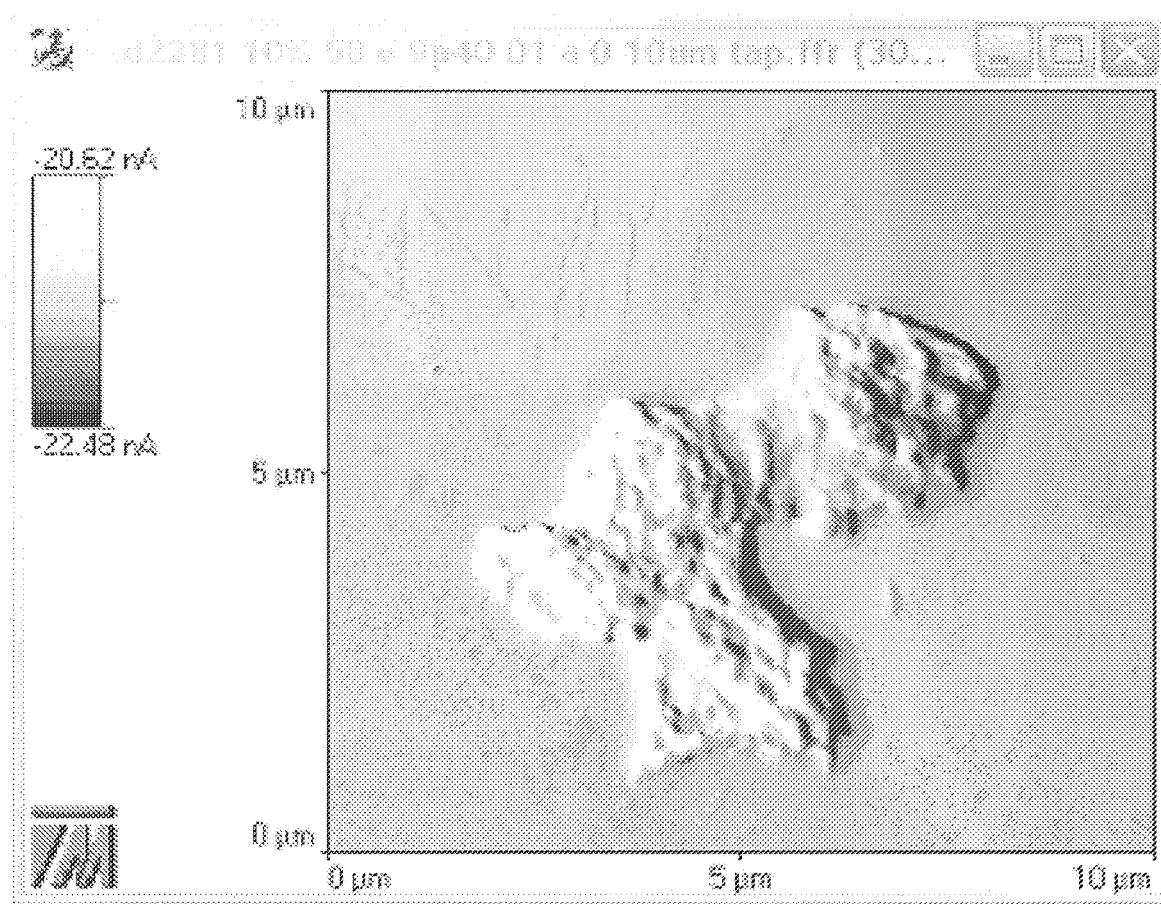
Figure 7:
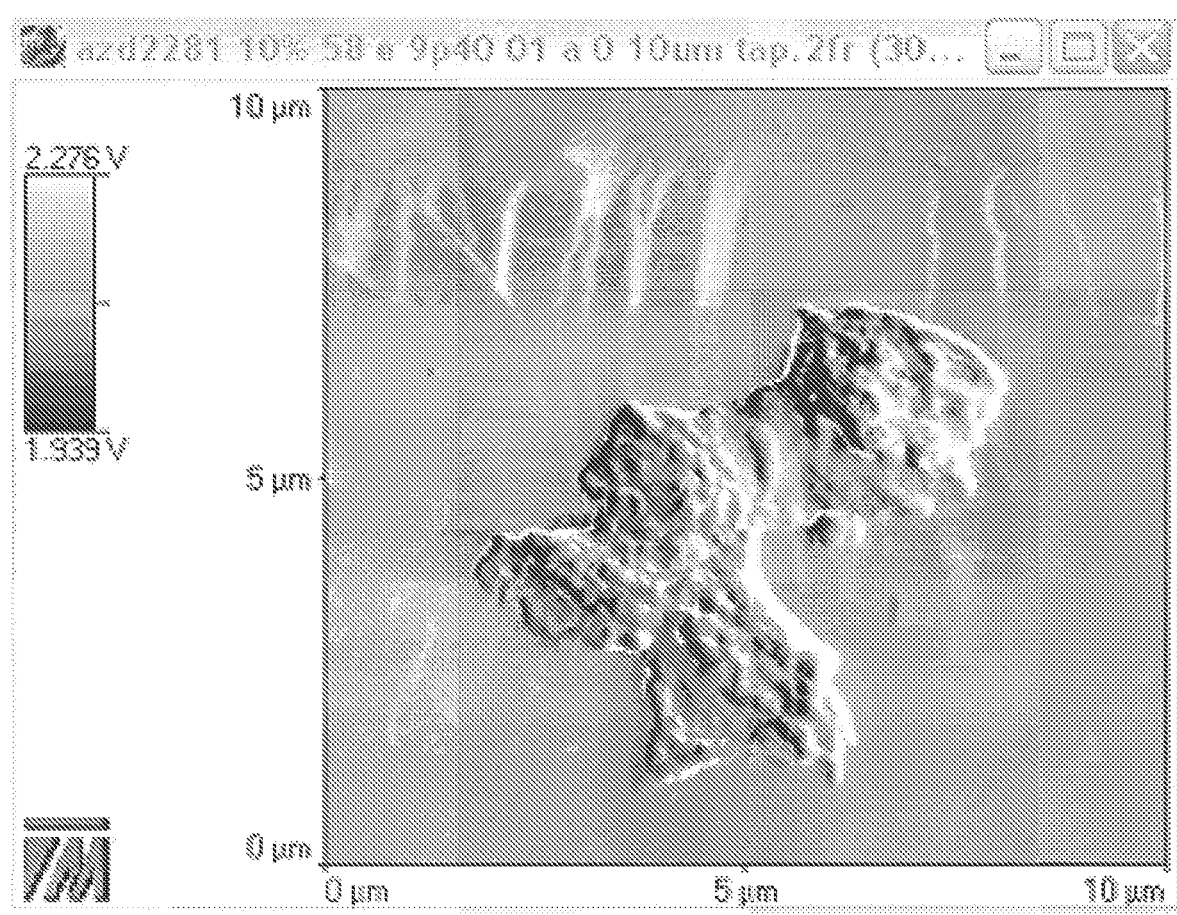
Figure 8:
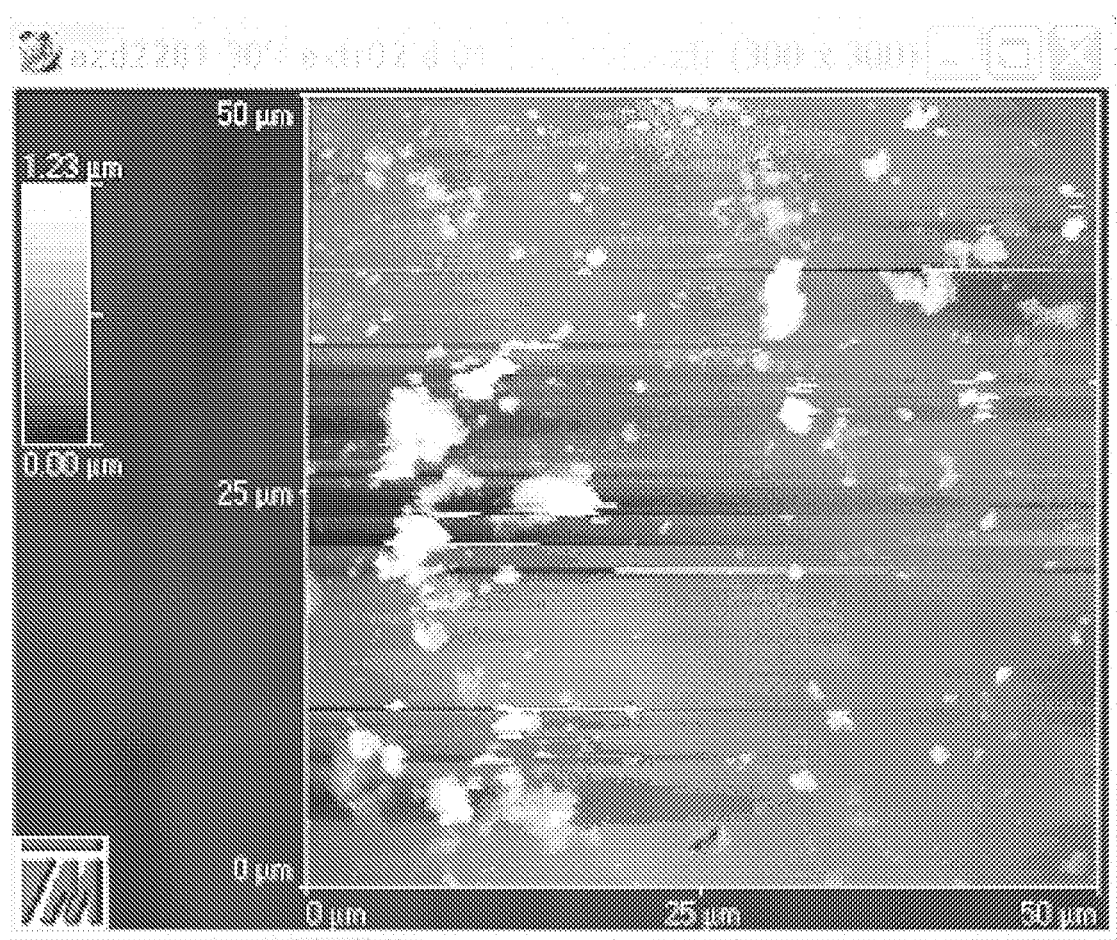
FIGS. 8(1)-8(6) show TM-AFM topographic (height), tip-deflection (error) and phase (mechanical property) images from 50 μm×50 μm and 10 μm×10 μm scans for solid dispersions of compound 1 and copovidone at 30% drug loading:—
Figure 8:
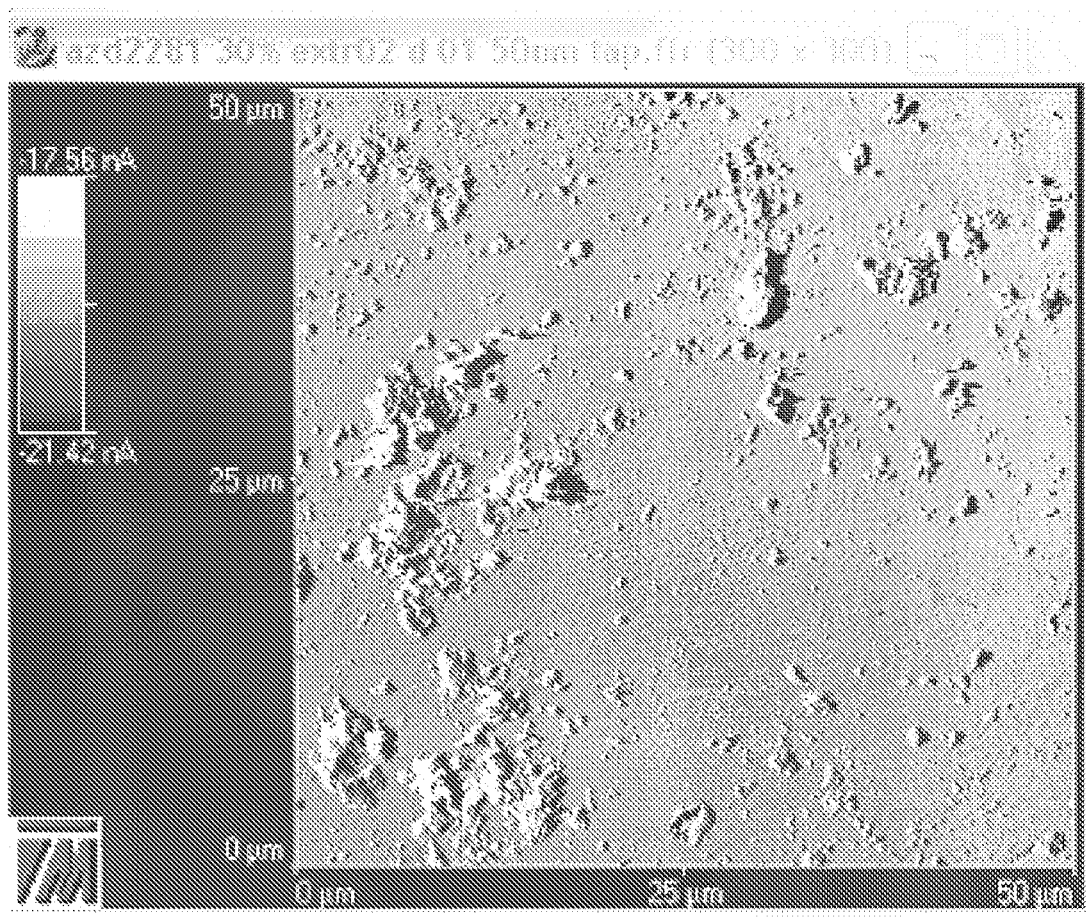
Figure 8:
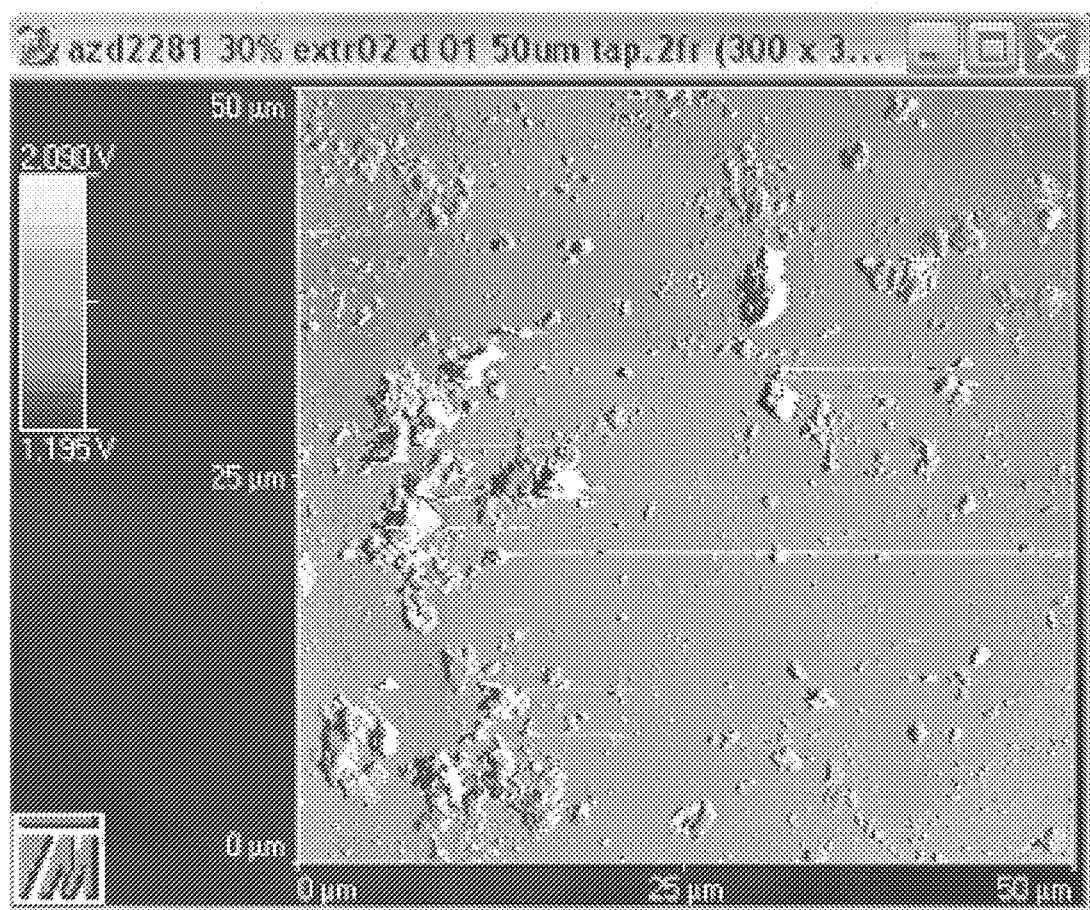
Figure 8:
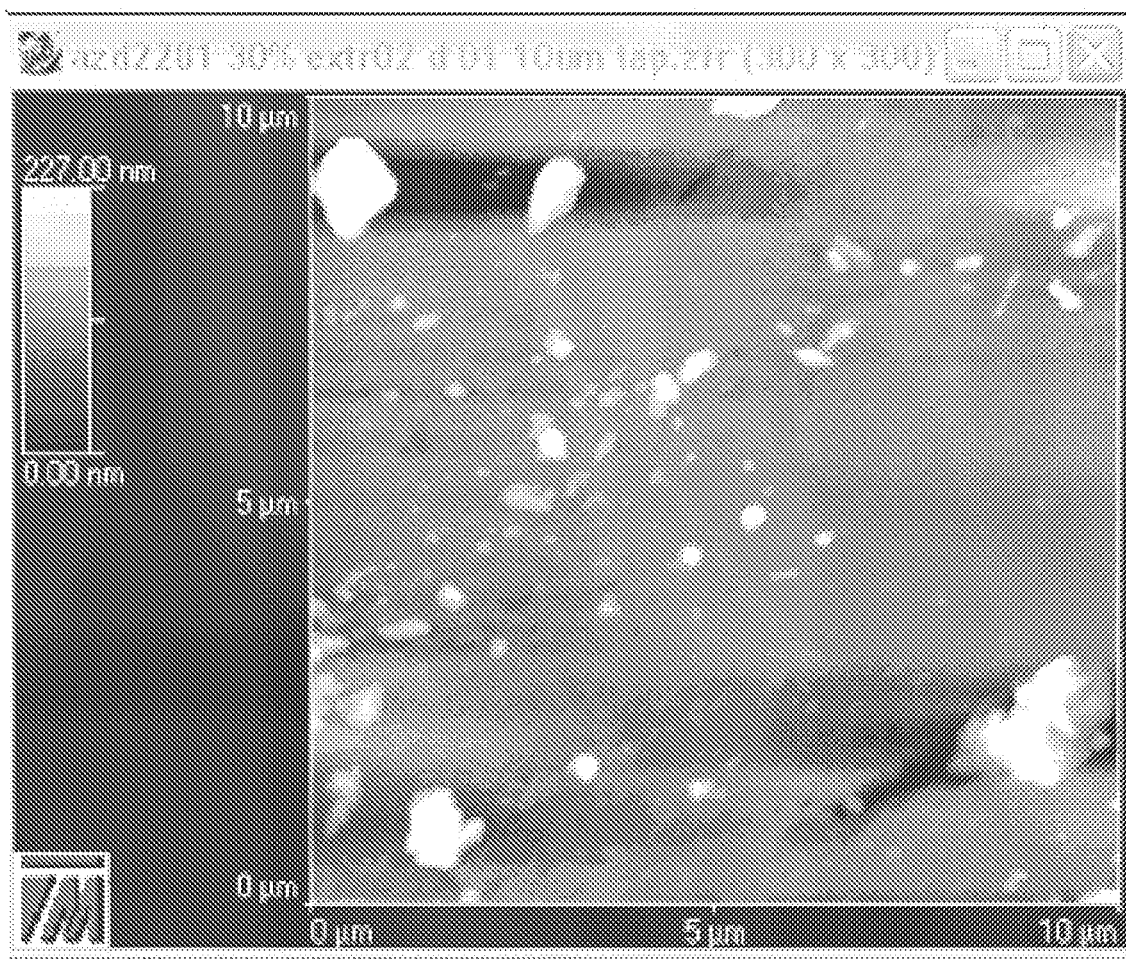
Figure 8:
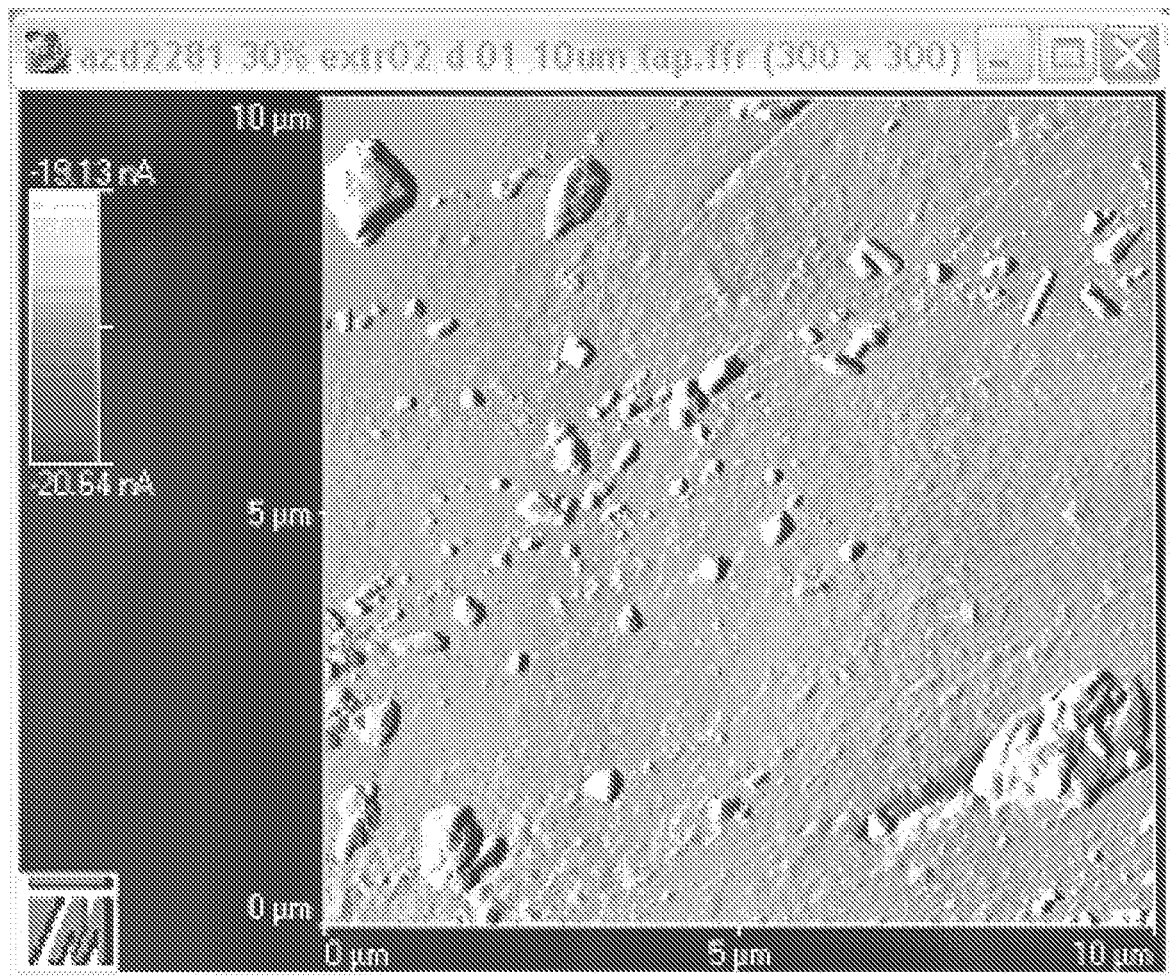
Figure 8:
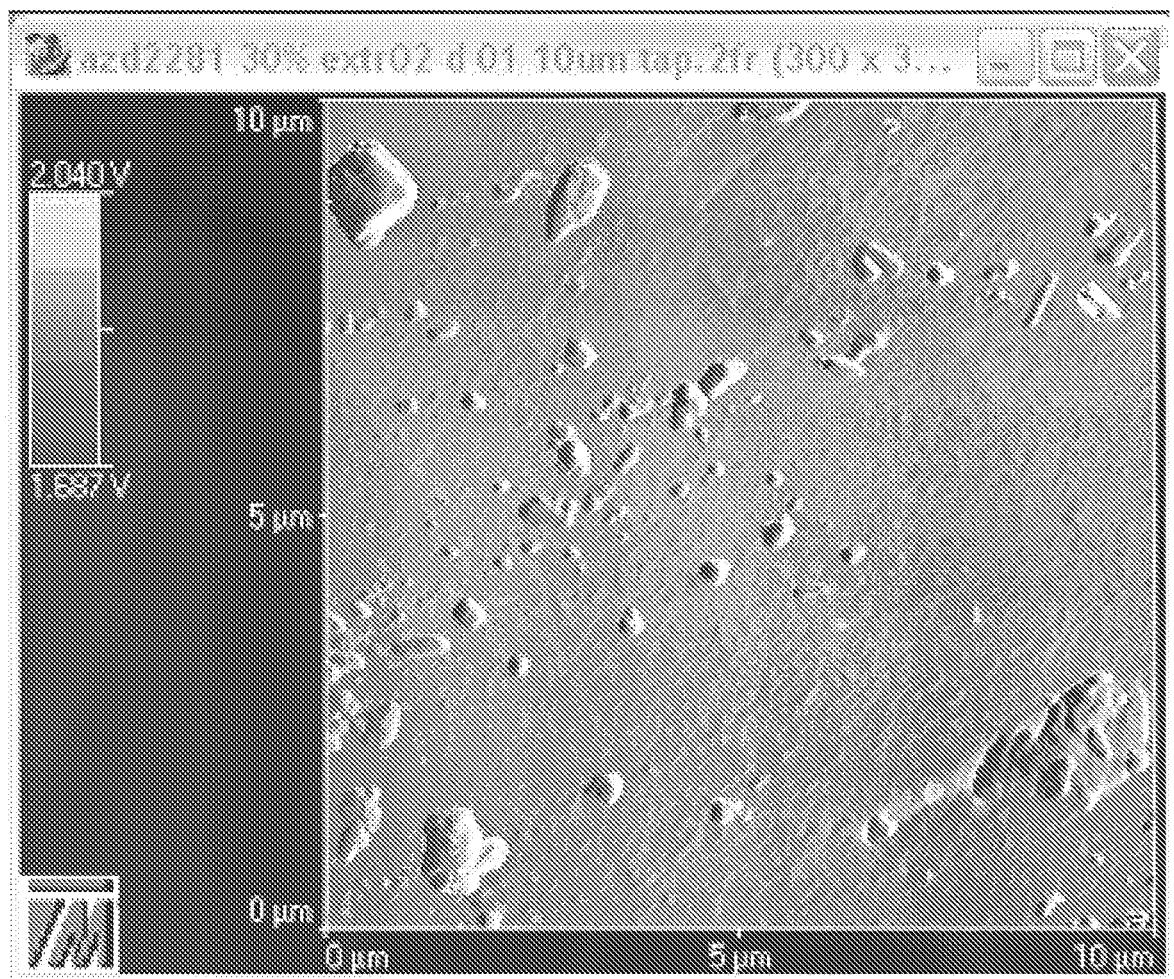
Figure 9:
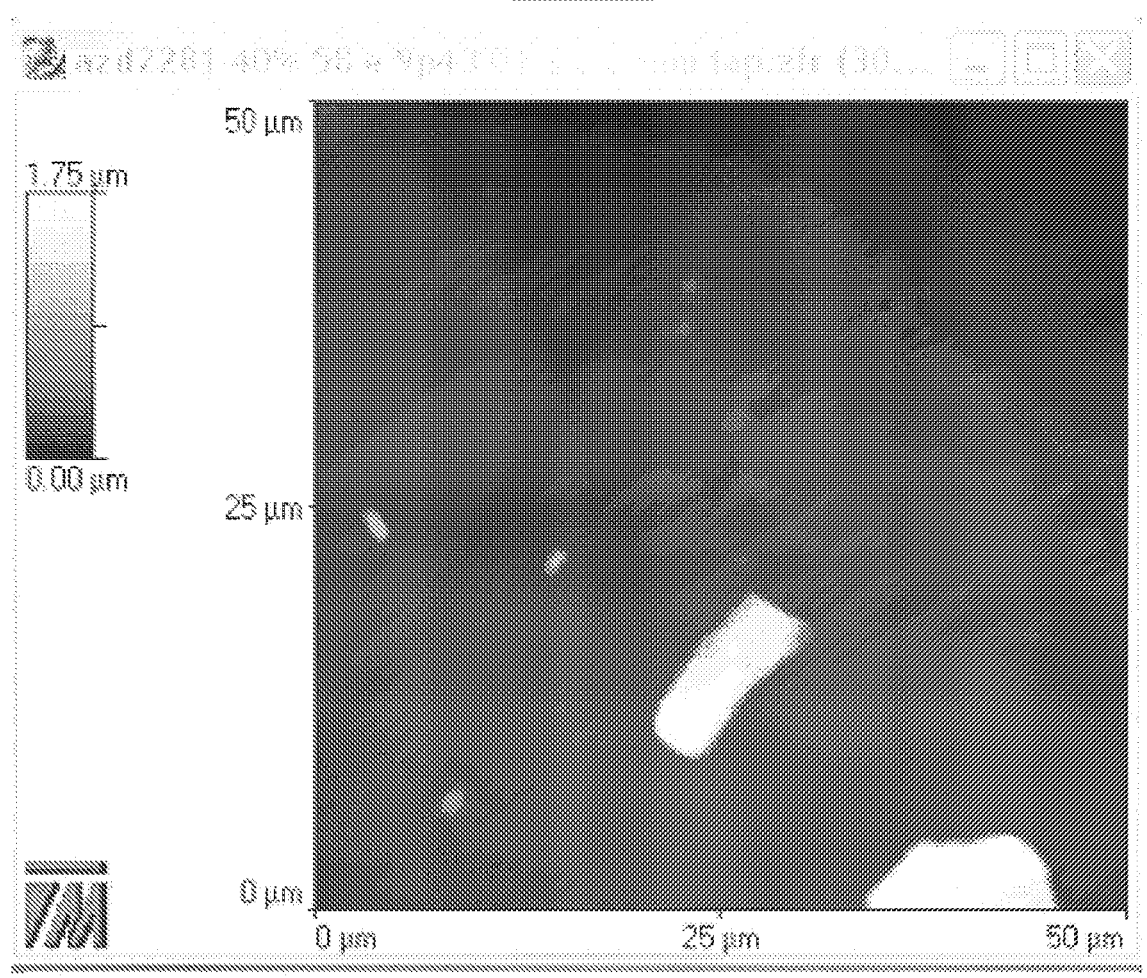
FIGS. 9(1)-9(6) show TM-AFM topographic (height), tip-deflection (error) and phase (mechanical property) images from 50 μm×50 μm and 10 μm×10 μm scans for solid dispersions of compound 1 and copovidone at 40% drug loading:—
Figure 9:
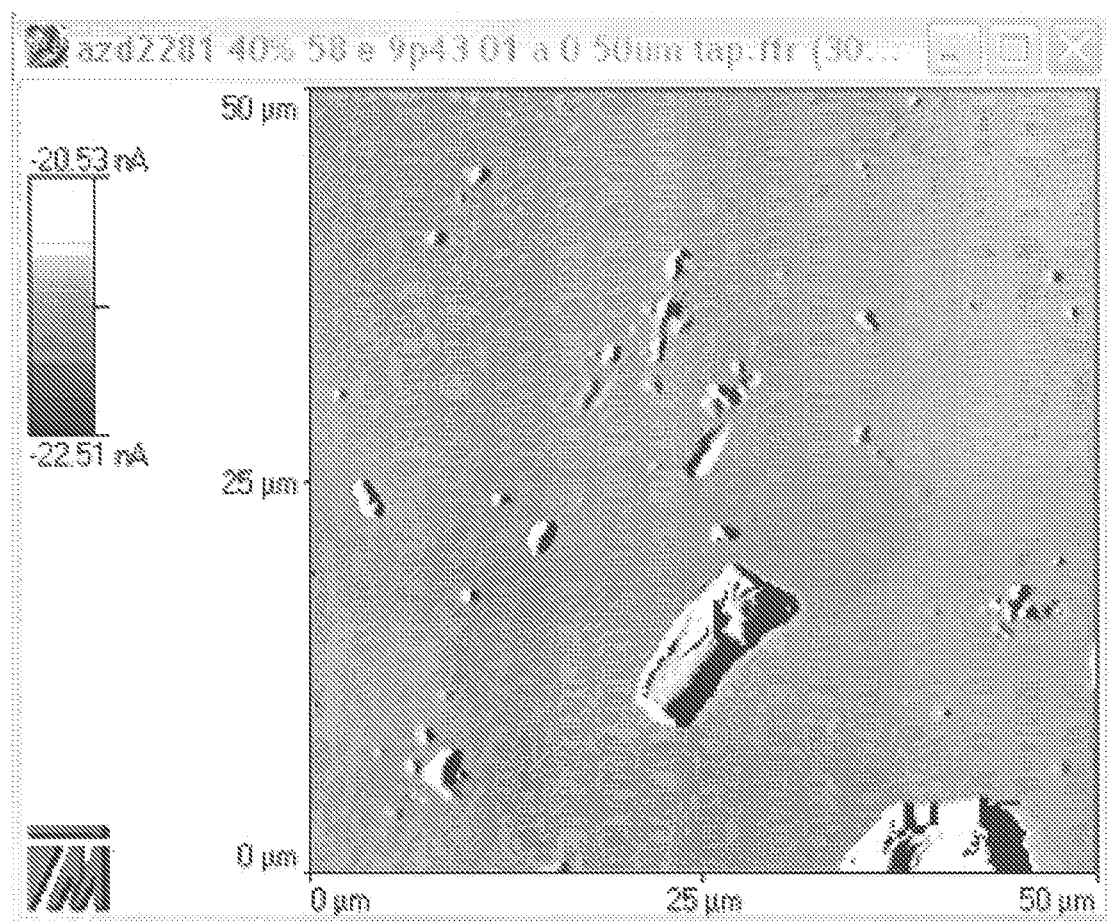
Figure 9:
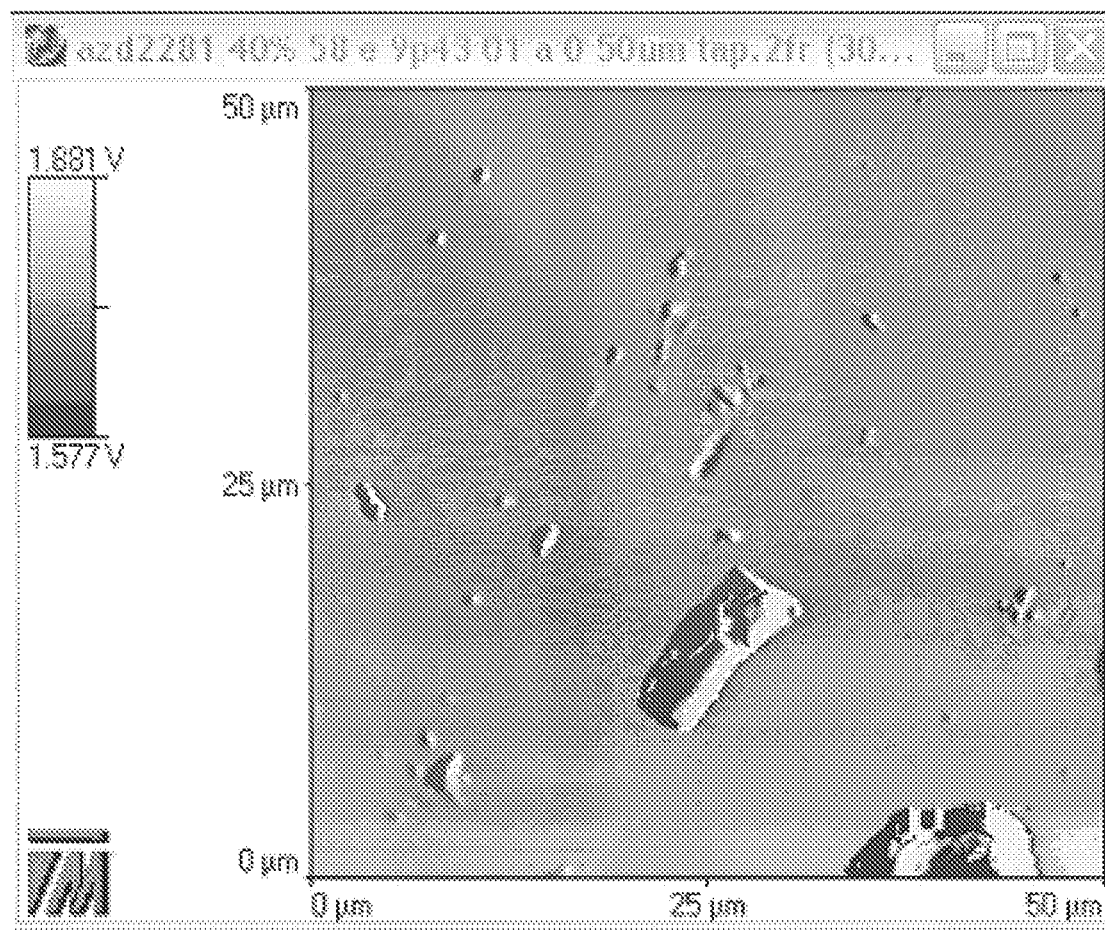
Figure 9:
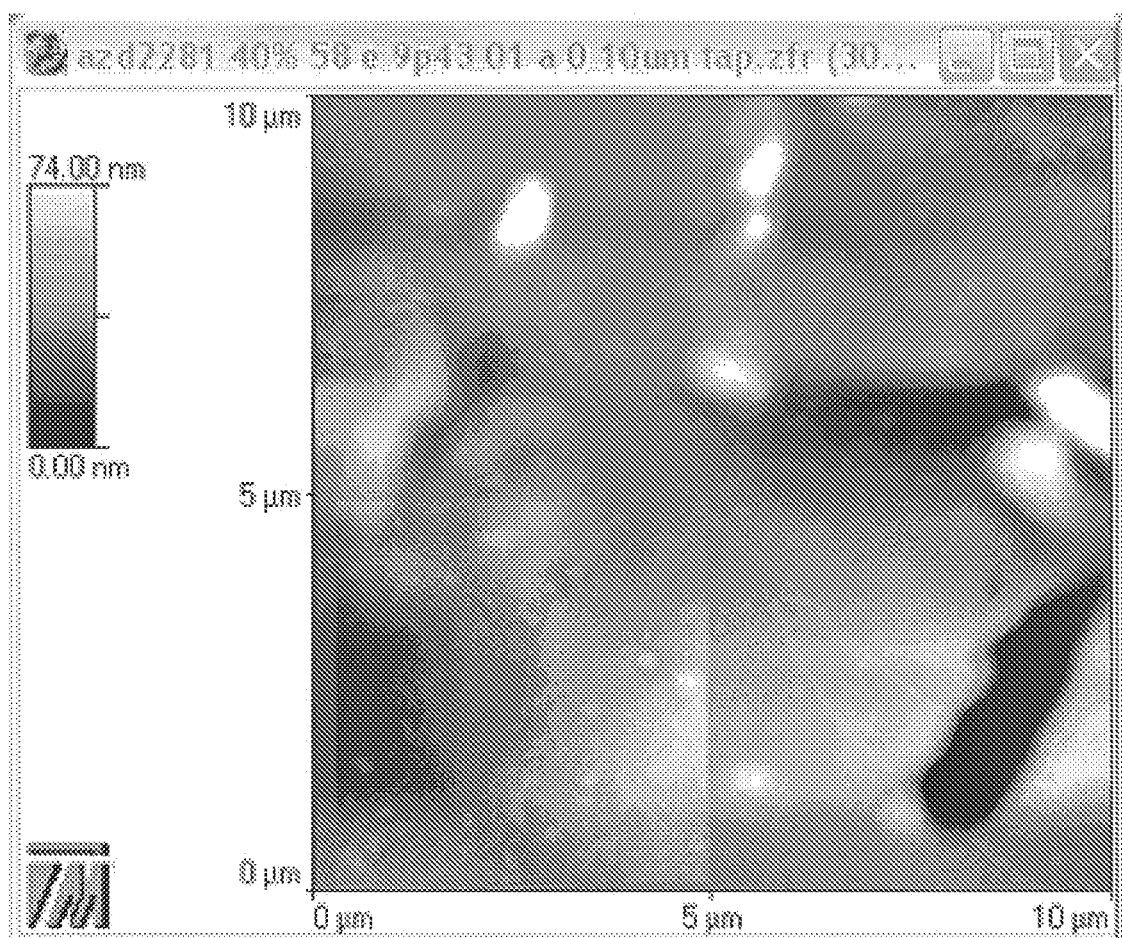
Figure 9:
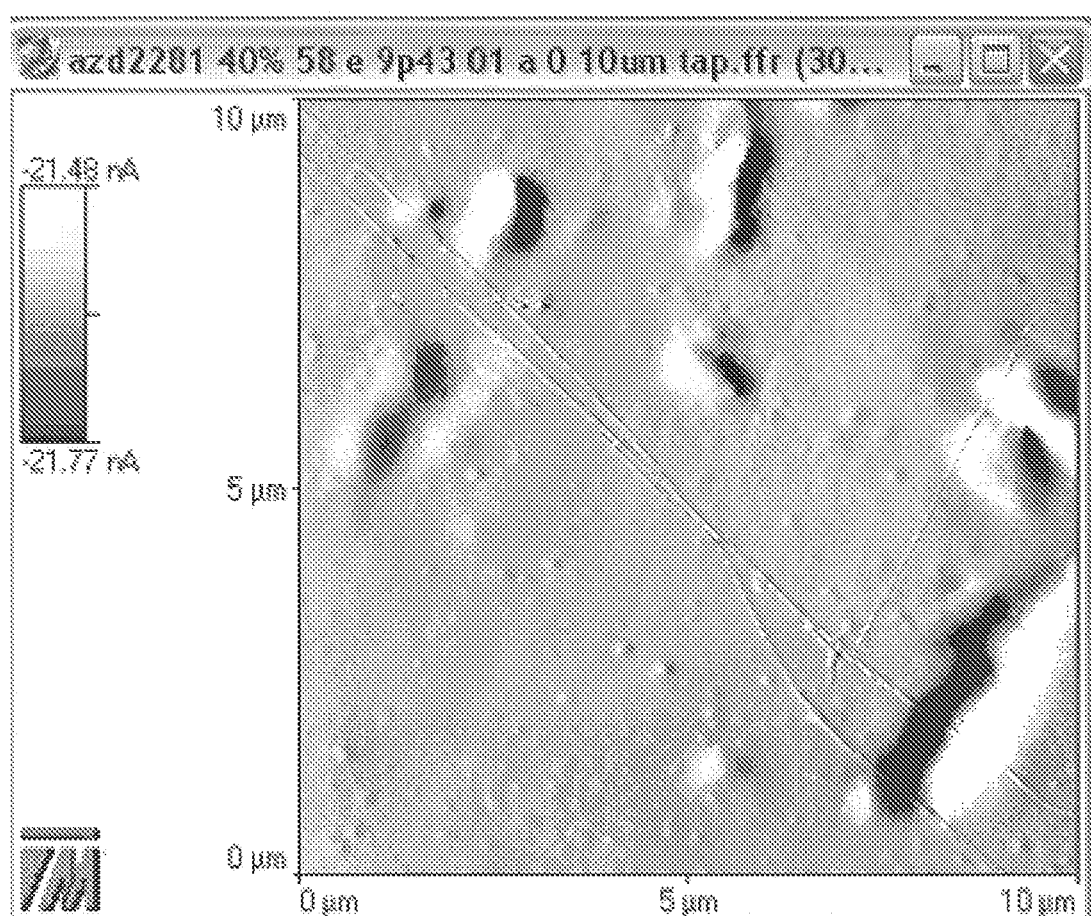
Figure 9:
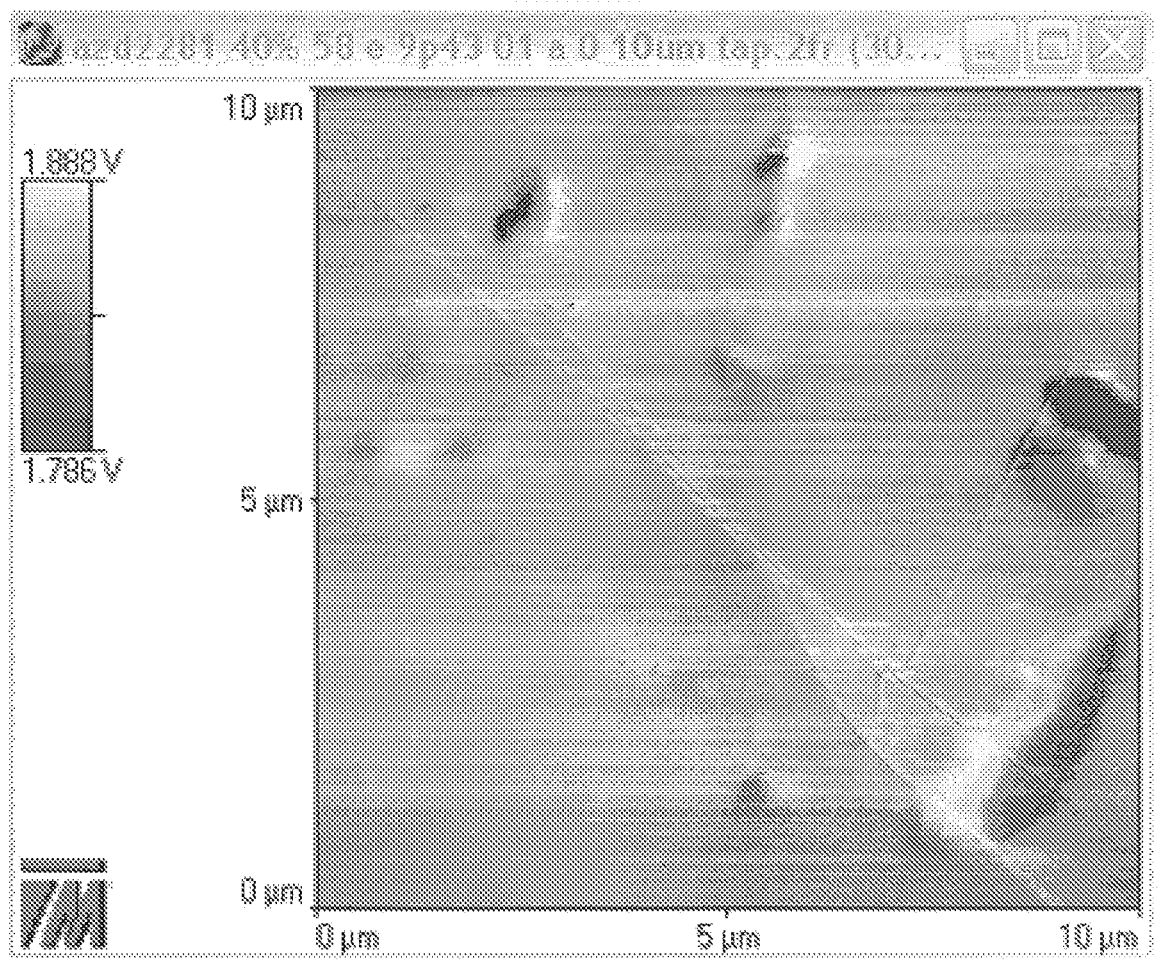

The samples at various drug loadings all exhibited surface features to a variable degree, but none showed any evidence of phase separation within the matrix, as illustrated in FIG. 7 (10% drug loading), FIG. 8 (30% drug loading) and FIG. 9 (40% drug loading).

5.4 Crystallisation Study

The effect of water on the crystallinity of Compound 1 was investigated for the milled extrudate prepared using the melt extrusion process described in 4.6.2 and for the tablet composition shown in Table 12 and prepared as described in 4.7.2. The study was carried out using aqueous slurries both in the absence and presence of a proprietary coating composition, Opadry™ Green (Colorcon 03B21726, 130 g/Kg aqueous solution). Tablets were ground prior to the slurry experiments commencing.

5.4.1 Experimental Conditions

The following materials were weighed into 25 mL vials:

TABLE 21

Preparation of slurries for crystallisation study

| | Weight (mg) | | |
|---|---|---|---|
| Exp | Ground tablet | Milled extrudate | Opadry |
| 1 | 83.0 | — | 199.2 |
| 2 | — | 67.7 | 208.2 |
| 3 | 91.0 | — | — |
| 4 | — | 68.0 | — |

20 mL of water heated to 50° C. was added to each vial. The resulting slurries remained stirring at 50° C. for 48 hours.

Analysis of the resultant slurry material by XRPD identified Form H as the primary crystal form of Compound 1. Compound 1 Form H has an X-ray diffraction pattern ($\lambda=1.5418$ Å) containing specific peaks at:

TABLE 22

XRPD data for Compound 1 Form H

| Peak | 2θ°(±0.1°) |
|---|---|
| 1 | 6.5 |
| 2 | 6.9 |

TABLE 22-continued

XRPD data for Compound 1 Form H

| Peak | 2θ°(±0.1°) |
|---|---|
| 3 | 8.4 |
| 4 | 12.8 |

Compound 1 Form H may also have the following additional peaks an X-ray diffraction pattern (λ=1.5418 Å):

TABLE 23

Additional XRPD data for Compound 1 Form H

| Peak | 2θ°(±0.1°) |
|---|---|
| 5 | 15.1 |
| 6 | 16.5 |
| 7 | 16.8 |
| 8 | 19.9 |
| 9 | 20.3 |

Compound 1 Form H may also be characterised by any combination of three or more peaks selected from the first list of 4 peaks above.

Figure 10:
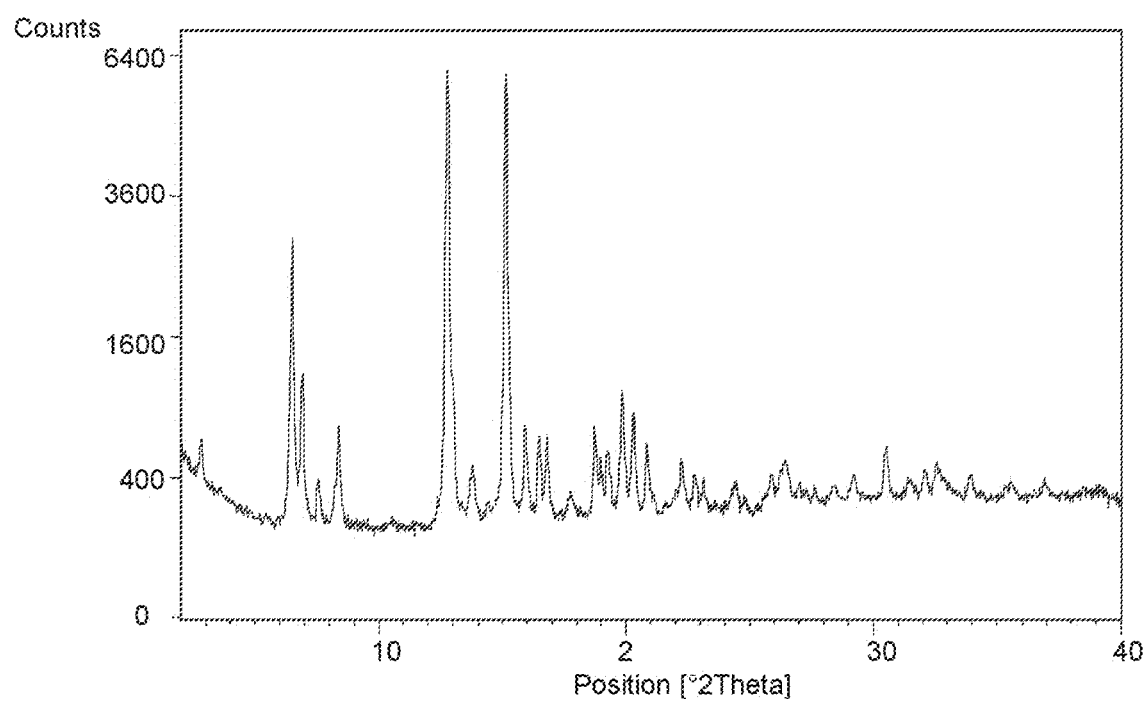
FIG. 10 shows an XRPD diffractogram for Compound 1 Form H

A representative powder XRPD pattern of compound 1 Form H is shown in FIG. 10.

Compound 1 Form H gives a weight loss via TGA that is consistent with a monohydrate with some additional physisorbed water. In the example given the total amount of water present is 4.7% by weight; the theoretical weight loss for a monohydrate of compound 1 is 4.0% w/w.

Figure 11:
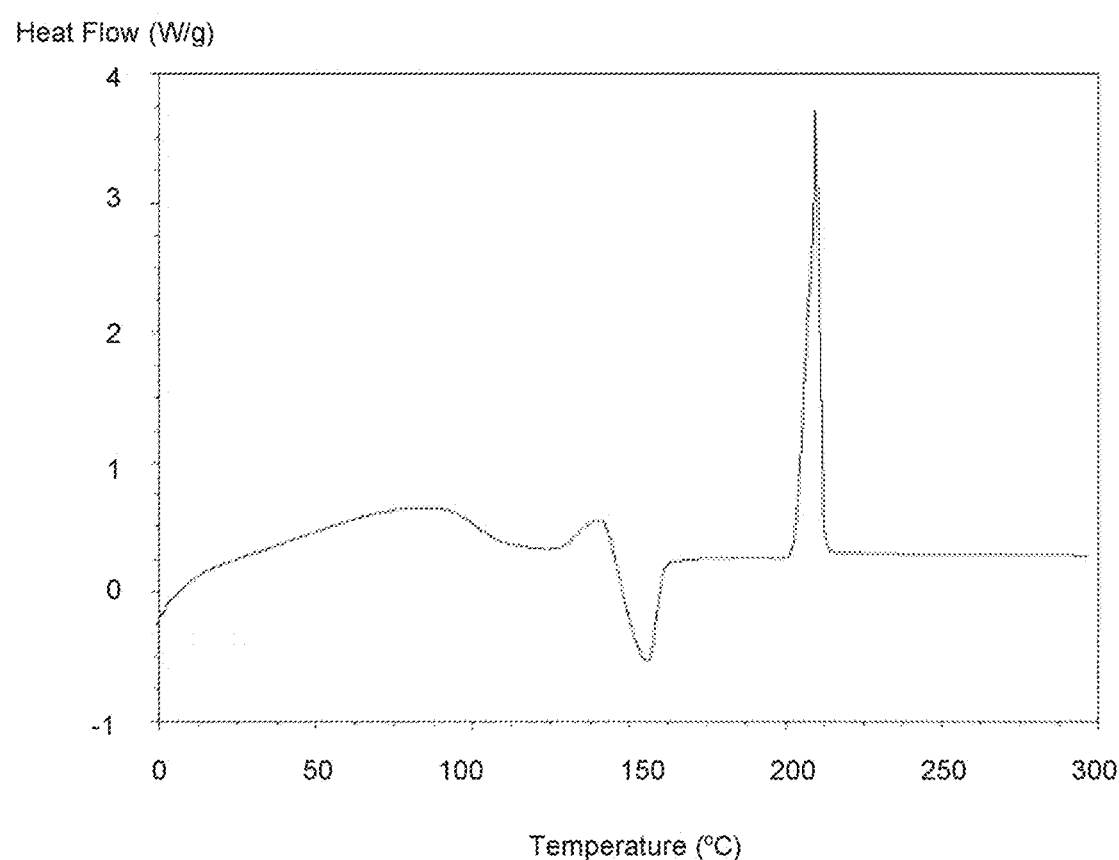
FIG. 11 shows a representative DSC trace for Compound 1 Form H

Compound 1 Form H may also be characterised using DSC. Compound 1 Form H when heated from 0° C. to 300° C. at 10° C. per minute displays a broad dehydration endotherm up to 115° C., followed by phase transitions between 125-175° C. A sharp endotherm is observed with an onset at 208.0° C.±1° C., this being consistent with Form A. A representative DSC trace for compound 1 as Form H is shown in FIG. 11.

Figure 12:
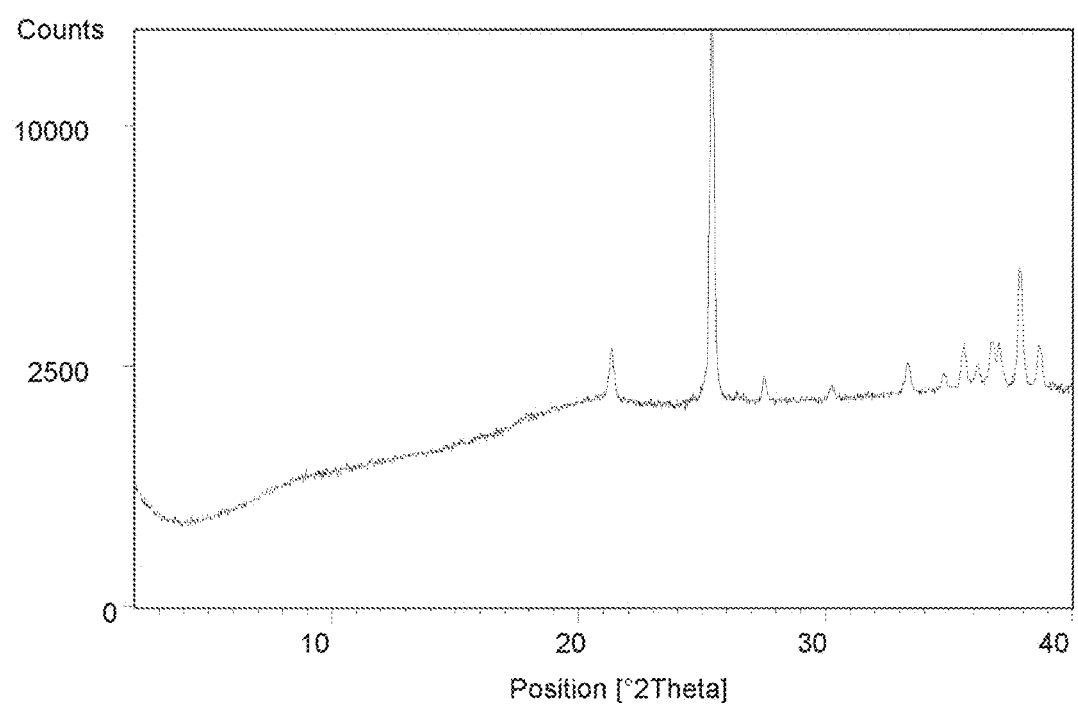
FIG. 12 shows an XRPD diffractogram for Opadry

In the absence of Opadry™ the resulting material gave strong XRPD reflections consistent with Form H, whereas in the presence of Opadry™ the intensity of the Form H XRPD diffraction pattern was considerably reduced. This is not the result of interference, as the XRPD diffraction pattern of Opadry™ shown in FIG. 12 indicates there are no significant peaks present below 25°2θ. Therefore, the very low intensity of the reflections observed indicates the presence of only small quantities of Form H. This may suggest that Opadry™ may exert a stabilising effect upon amorphous solid dispersions of Compound 1. This grade of Opadry™ was selected for use in the preparation of the film-coated tablet formulation described in 4.8.

5.5 Two-Dimensional Correlation Spectroscopy Study 5.5.1 Introduction

Two-dimensional correlation spectroscopy (2D-COS) is a method in which an external perturbation is applied to a system and monitored by some spectrometric device. Spectral intensity is plotted as a function of spectral variables (e.g. wavelength, frequency or wavenumber). Two orthogonal axes of spectral variables define the 2D spectral plane, and the spectral intensity may be plotted along a third axis (Noda, I., Dowrey, A. E., Marcott, C., Story, G. M., Ozaki, Y. Appl. Spectrosc. 54 (7) 2000 pp 236A-248A; Noda, I. Appl. Spectosc. 44 (4) 1990 pp 550-561).

In a synchronous 2D correlation spectrum, intensity is representative of the simultaneous or coincidental changes of spectral intensity variations measured across the range of perturbation. A synchronous spectrum is symmetrical with regard to the diagonal corresponding to equal values for the chosen spectral variable; correlation peaks appear at both diagonal and off-diagonal positions. The diagonal peaks, referred to as autopeaks, represent the intensity variation for specific values of the chosen spectral variable across the range of perturbation, whereas the off-diagonal peaks, referred to as cross peaks, represent simultaneous or coincidental changes of spectral intensities observed at two different values of the chosen spectral variable. Such synchronised changes may indicate a coupling or interaction.

In contrast, in the asynchronous spectrum, intensity represents sequential or successive changes. The asynchronous spectrum is anti-symmetrical with respect to the diagonal and has no autopeaks, consisting exclusively of cross peaks which develop only if the two spectral features change out of phase. This feature may be used to differentiate overlapped bands arising from spectral signals of different origins, such as different components acting independently in a complex mixture.

For both synchronous and asynchronous correlation spectra, sensitivity may be improved, at the expense of an increase in noise, by subtraction of the average spectrum from each individual spectrum in the perturbation data set Thus 2D-COS may be used to establish the nature and extent of any correlations in the spectral variations which arise in response to the perturbation and which may be indicative of intra- or inter-molecular interactions within the sample matrix. In the context of a pharmaceutical solid dispersion, a high level of interaction between the drug and the matrix polymer will tend to promote the formation of a stable and homogeneous dispersion whereas the absence of such interaction, or the existence of competitive intramolecular coupling, will have a contrary effect.

5.5.2 Method

The effect of a change in concentration of Compound 1 and various polymers in solid dispersions prepared by the solvent evaporation process described in 4.6.1 was studied using infrared spectroscopy. The spectra were collected on a Thermo Nicolet Magna 550 series II spectrometer. 2D-COS spectra were collected for solid dispersion compositions of Compound 1 and matrix polymers as shown in Table 24.

TABLE 24

List of polymers with percent of mixtures]

| Composition | | Matrix polymer | | | | |
|---|---|---|---|---|---|---|
| API % | Polymer % | Hypromellose acetate succinate (Aqoat MG) | Copovidone (Kollidon VA64) | Hypromellose phthalate (HP55S) | Hypromellose (Pharmacoat 606) | Povidone (Kollidon 25) |
| 10 | 90 | T | T | T | T | T |
| 20 | 80 | T | T | T | T | T |

TABLE 24-continued

List of polymers with percent of mixtures]

| Composition | | Matrix polymer | | | | |
|---|---|---|---|---|---|---|
| API % | Polymer % | Hypromellose acetate succinate (Aqoat MG) | Copovidone (Kollidon VA64) | Hypromellose phthalate (HP55S) | Hypromellose (Pharmacoat 606) | Povidone (Kollidon 25) |
| 23 | 77 | T | T | T | T | T |
| 25 | 75 | T | T | T | T | T |
| 26 | 74 | T | T | T | T | T |
| 28 | 72 | T | T | N/T | T | T |
| 30 | 70 | T | T | N/T | T | T |

T = tested
N/T = not tested

Each spectrum was normalised to the most intense band using proprietary software (Omnic 8.0). The spectra were then converted into a comma separated value (CSV) file, transferred to MS Excel™ and formatted for Matlab® (The MathWorks™) wherein 2D synchronous and asynchronous spectra were generated.

5.5.3 Results

Hypromellose Acetate Succinate (Aqoat MG)

Figure 13:
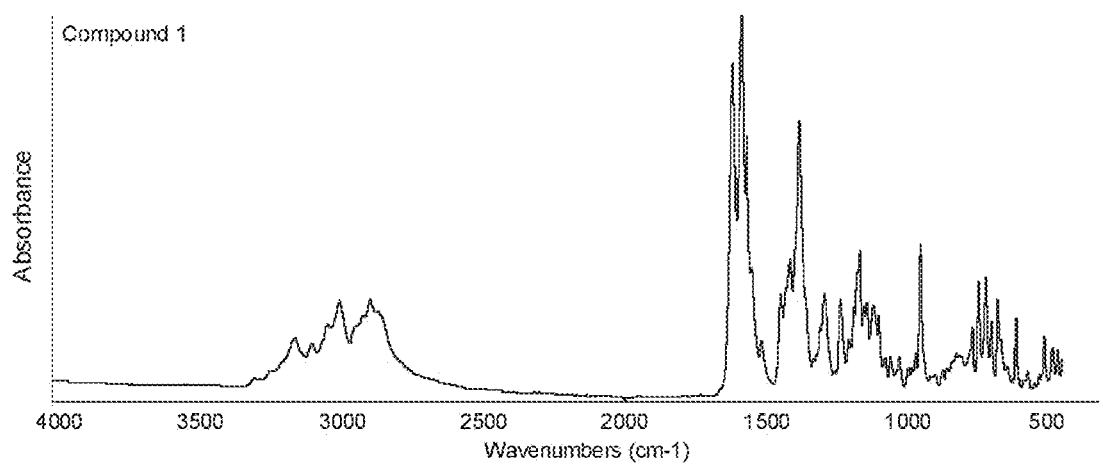
FIG. 13 shows an infrared spectrum of Compound 1
Figure 14:
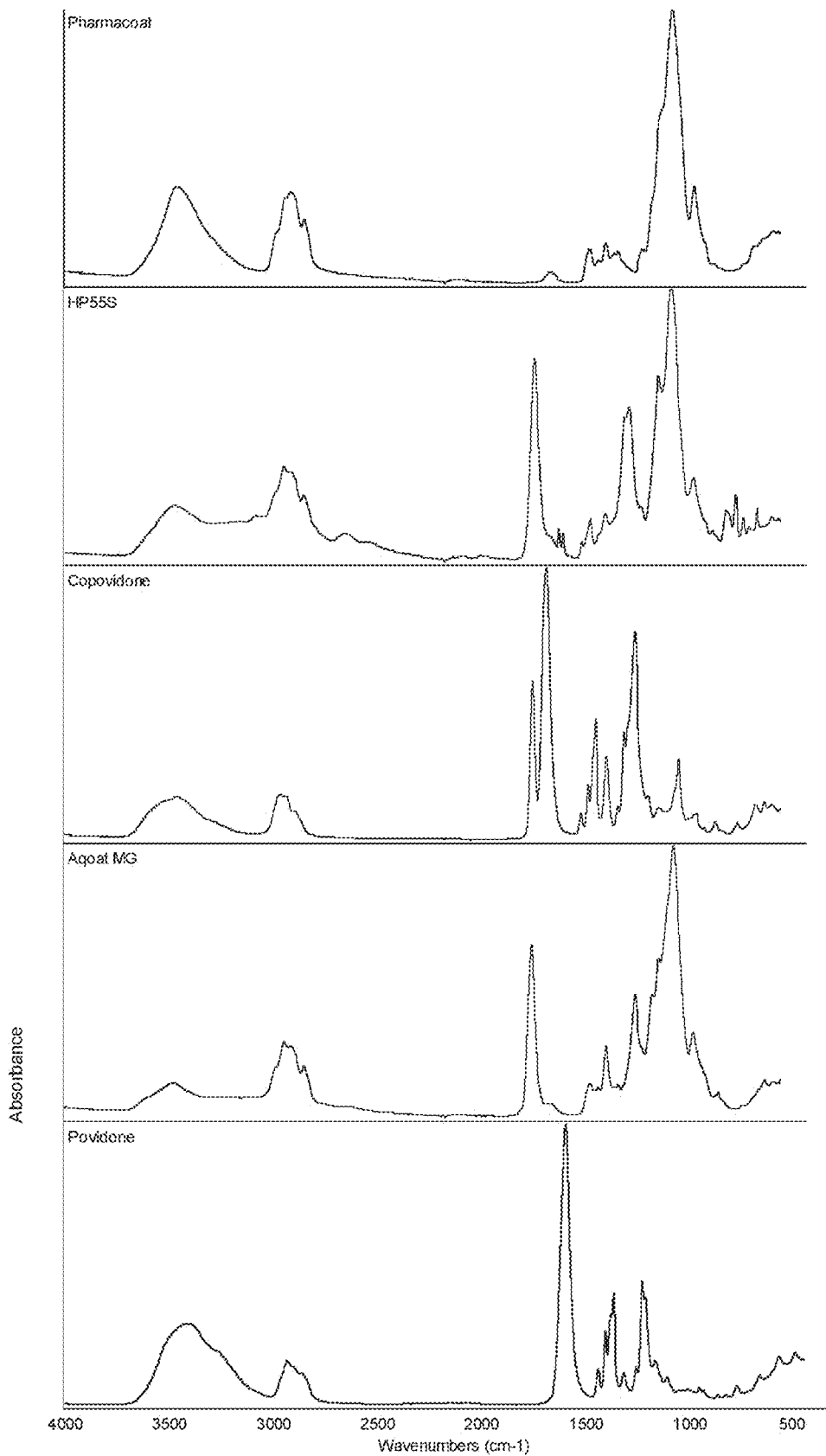
FIG. 14 shows infrared spectra of Aqoat MG, HP55S, Pharmacoat, Povidone and Copovidone
Figure 15:
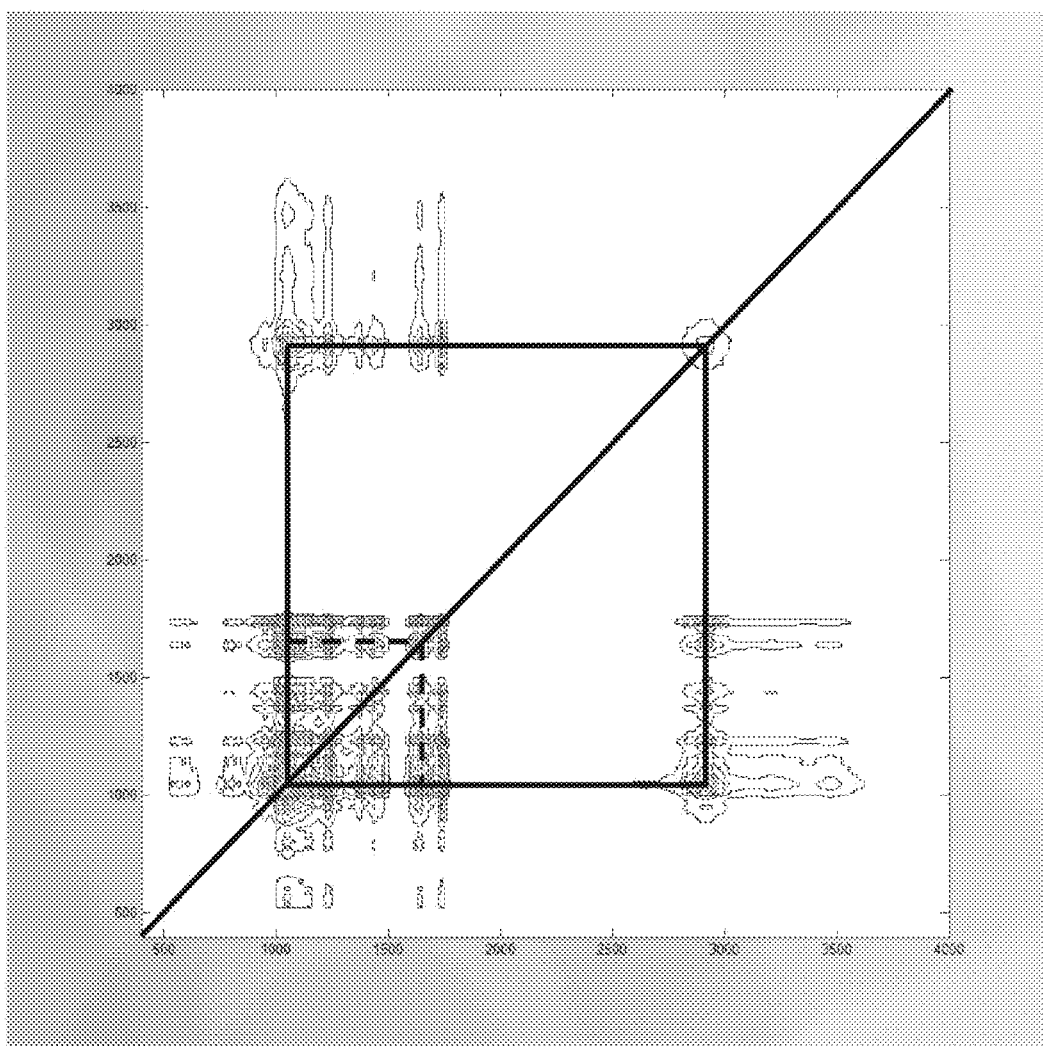
FIG. 15 shows a synchronous spectrum of Aqoat MG annotated with correlation squares
Figure 16:
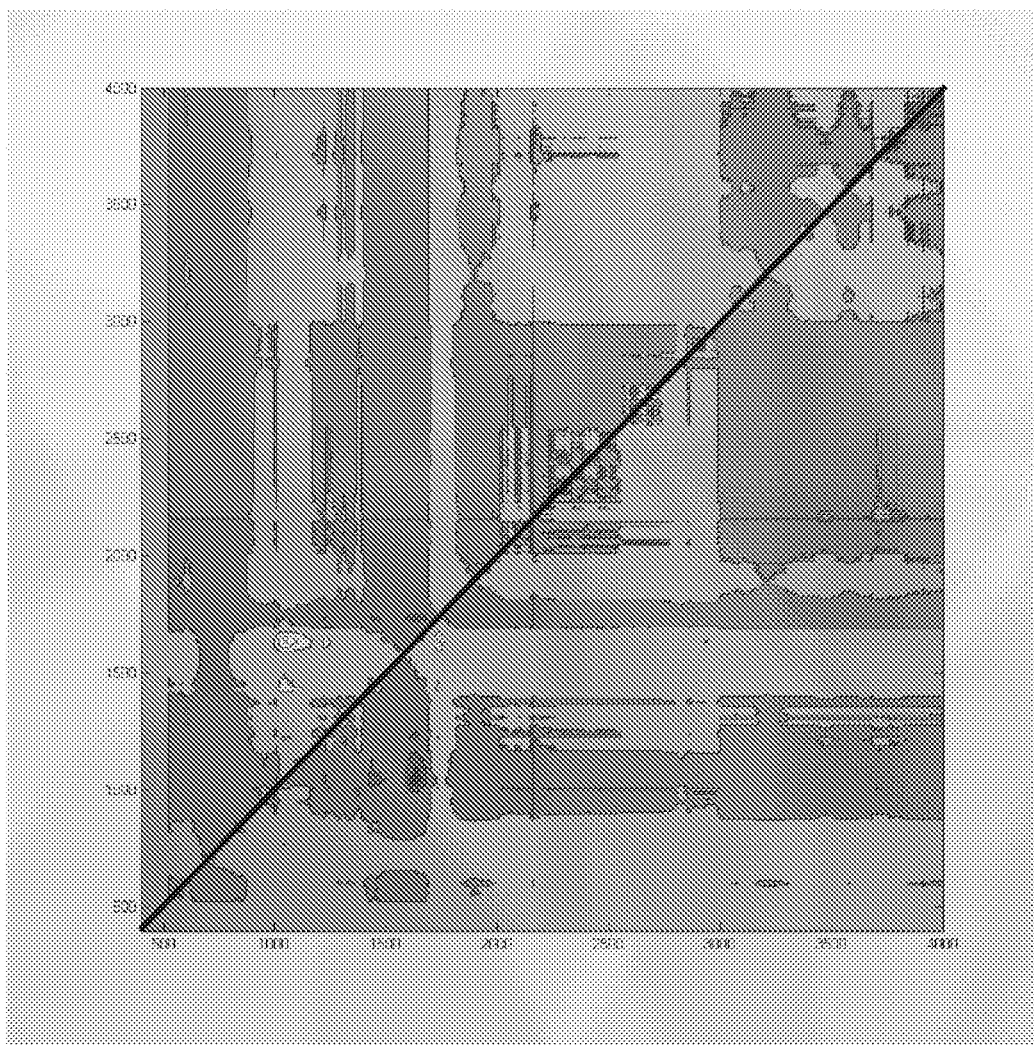
FIG. 16 shows an asynchronous spectrum of Aqoat MG

In the spectrum of Compound 1, the most intense band is located at 1630 cm$^{-1}$ (FIG. 13). In the Aqoat MG spectrum the most intense band is located at 1050 cm$^{-1}$ (FIG. 14). In the synchronous spectrum (FIG. 15) cross peaks are evident at 1050 cm$^1$, 1650 cm$^{-1}$ and 1050 cm$^1$, 2700 cm$^{-1}$; however the asynchronous spectrum (FIG. 16) indicates that these interactions are intramolecular (polymer/polymer) in nature.

Hypromellose Phthalate (HP55S)

Figure 17:
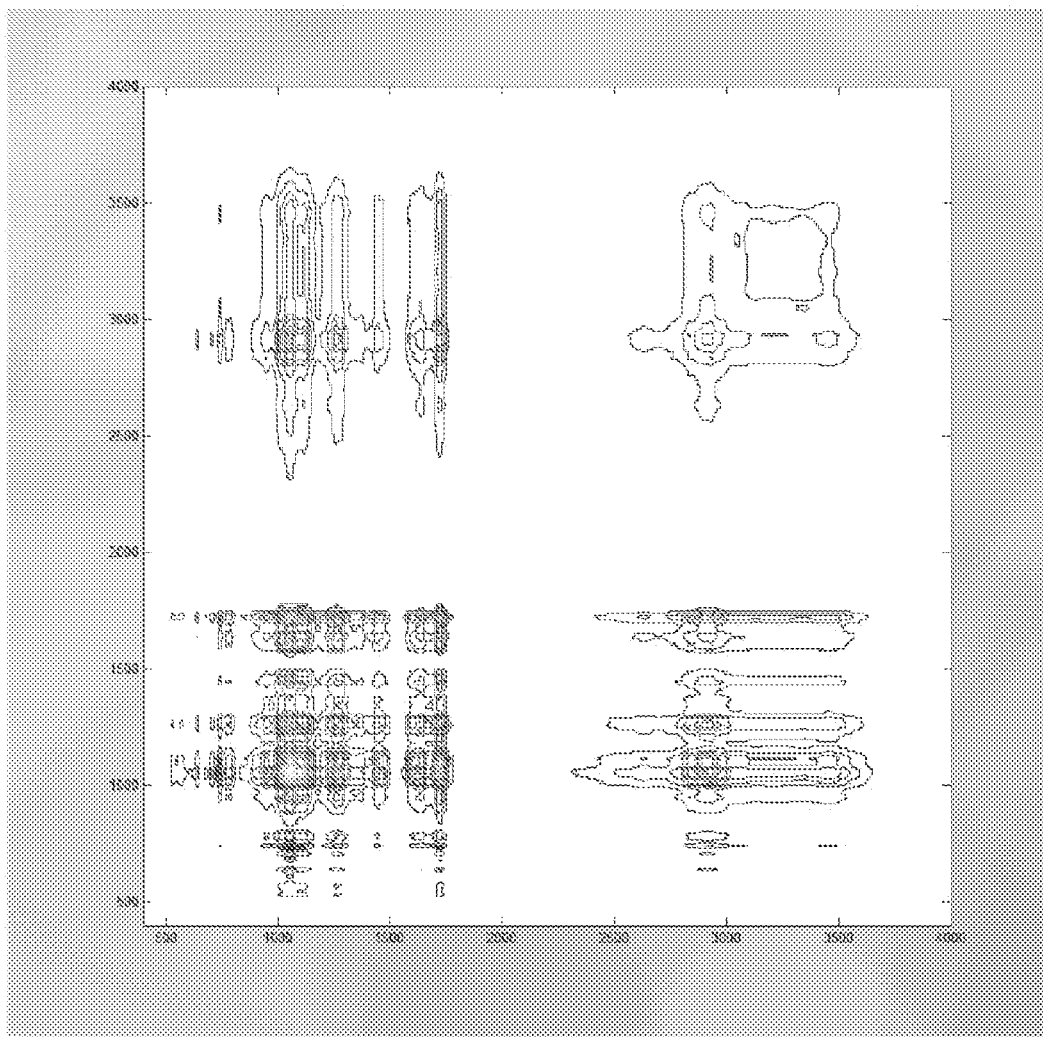
FIG. 17 shows a synchronous spectrum of HP55S
Figure 18:
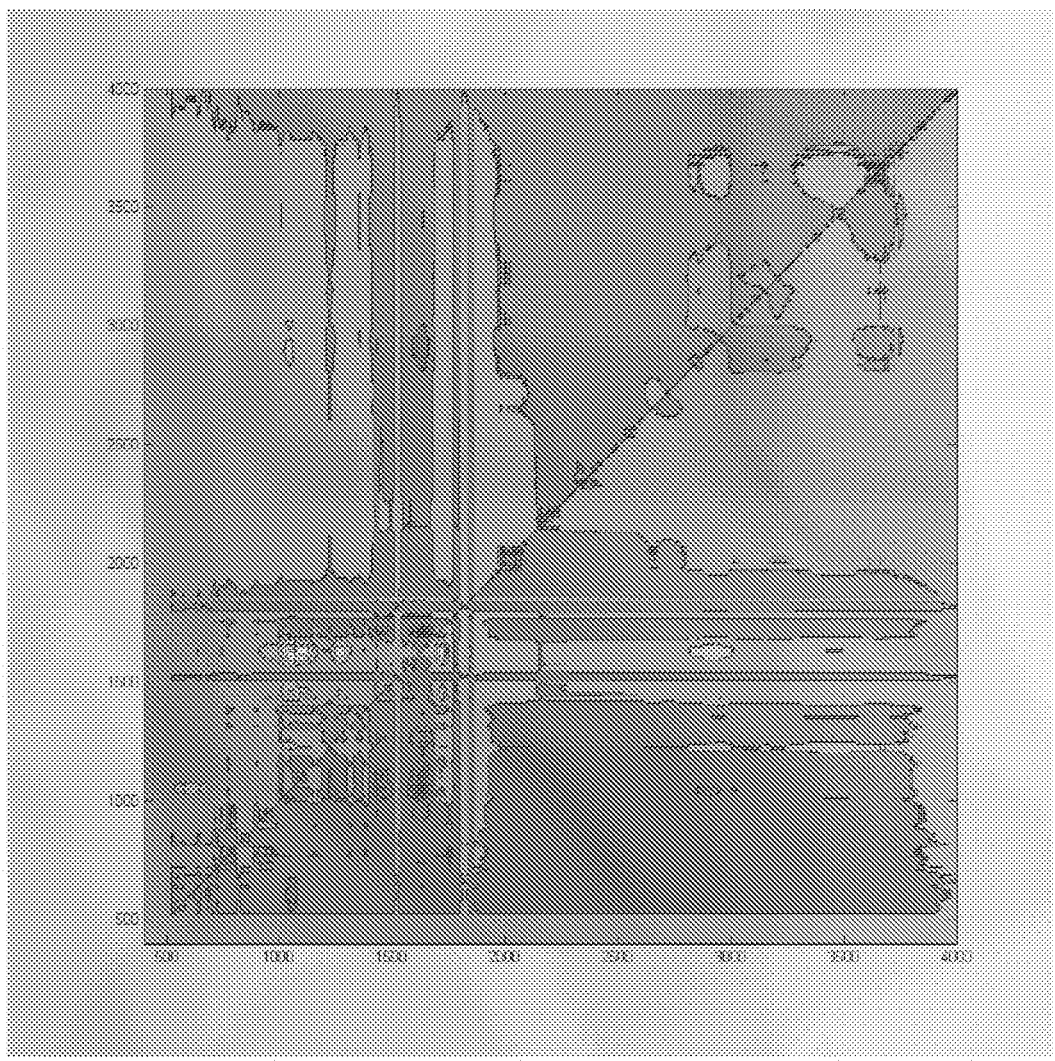
FIG. 18 shows an asynchronous spectrum of HP55S
Figure 19:
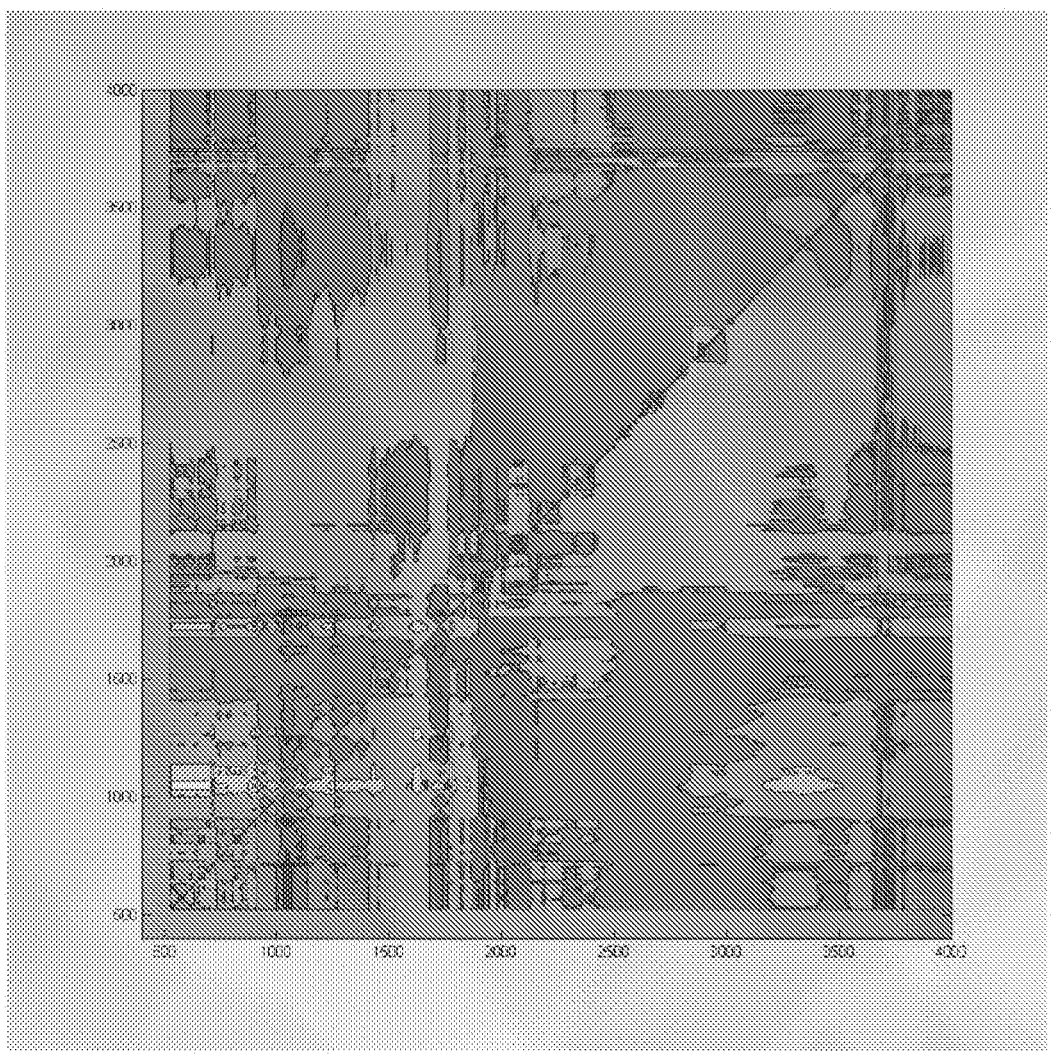
FIG. 19 shows an a synchronous spectrum of HP55S (high sensitivity)

The Infrared spectrum for HP55S exhibits a strong spectral feature at just above 1000 cm$^{-1}$, as shown in FIG. 14. The synchronous (FIG. 17) and asynchronous (FIGS. 18 and 19) correlation spectra indicate weak mixed intra- and inter-molecular interactions in the range 1600 to 1800 cm$^{-1}$.

Hypromellose (Pharmacoat 606)

Figure 20:
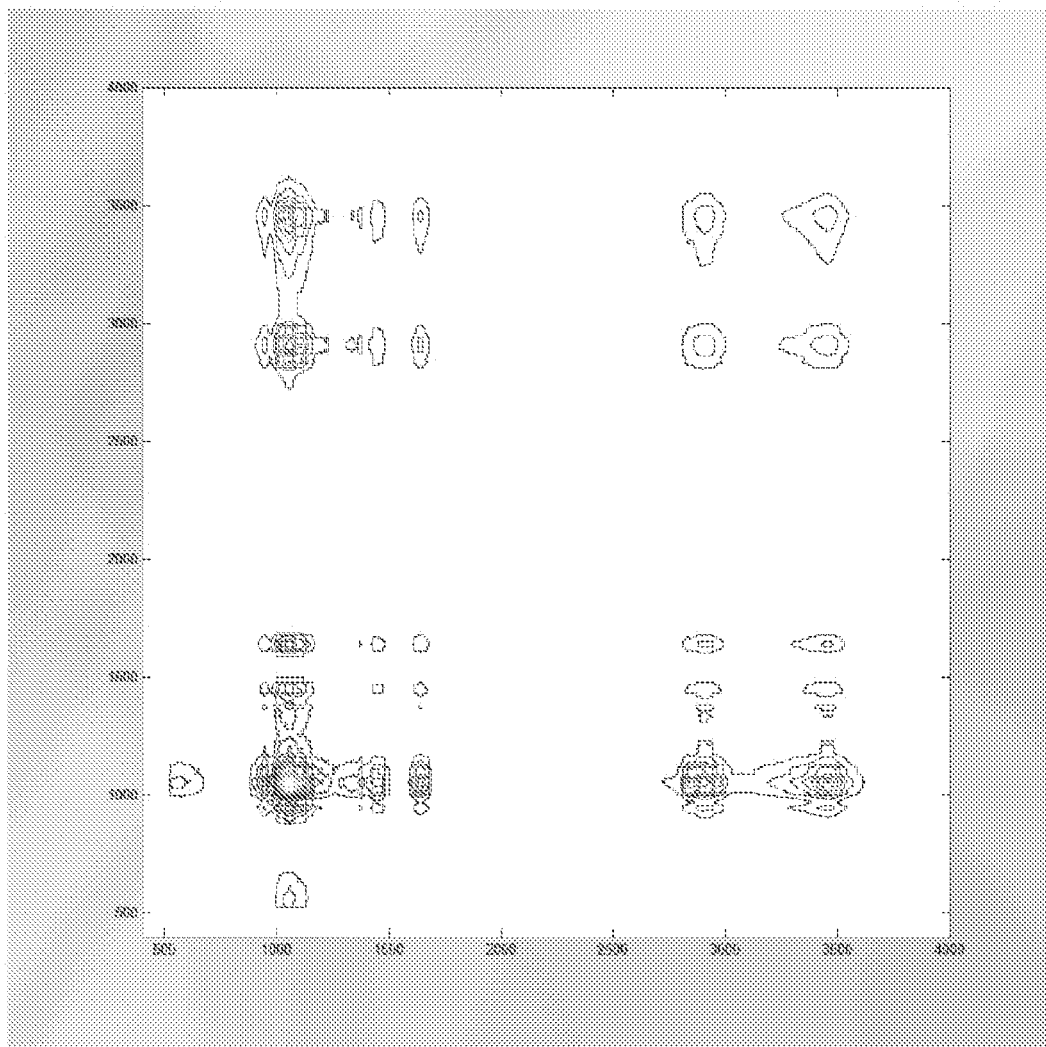
FIG. 20 shows a synchronous spectrum of Pharmacoat
Figure 21:
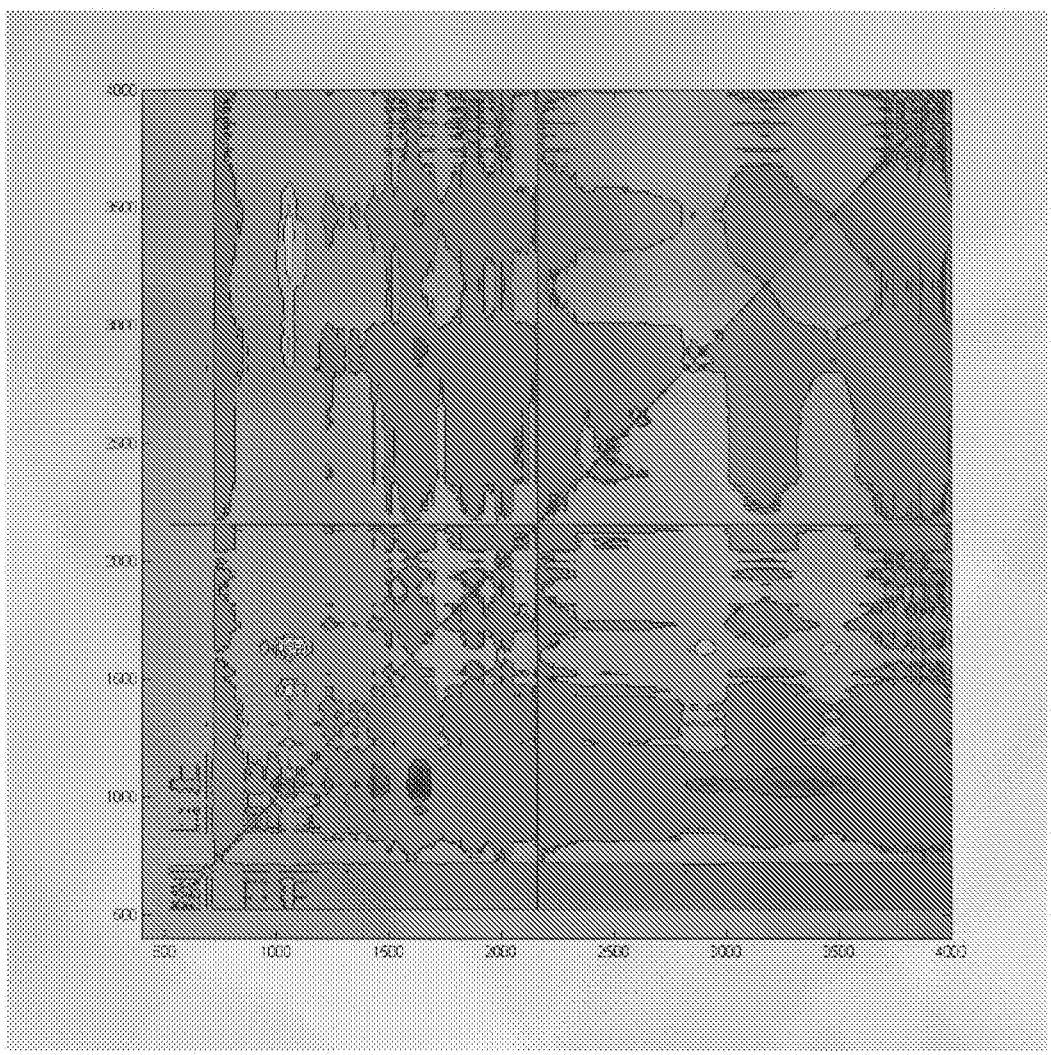
FIG. 21 shows an asynchronous spectrum of Pharmacoat
Figure 22:
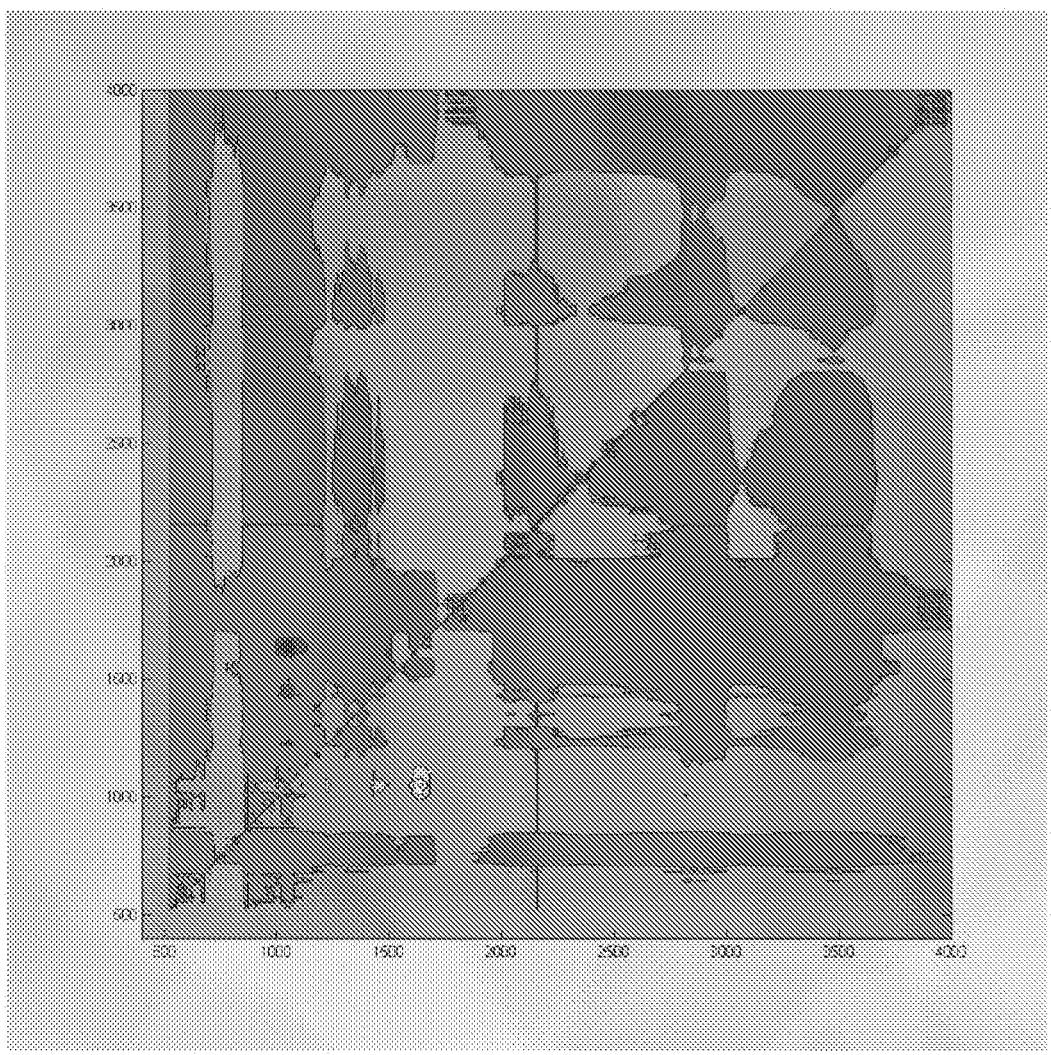
FIG. 22 shows an asynchronous spectrum of Pharmacoat (high sensitivity)

As for HP55S, the infrared spectrum for Pharmacoat exhibits a strong spectral feature at just above 1000 cm-1, (FIG. 14). The synchronous (FIG. 20) and asynchronous (FIGS. 21 and 22) correlation spectra indicate weak mixed intra- and inter-molecular interactions in the range 1600 to 1800 cm$^{-1}$. The intensity of intermolecular (drug-polymer) interaction for Pharmacoat is somewhat greater than for HP55S.

Povidone (Kollidon 25)

Figure 23:
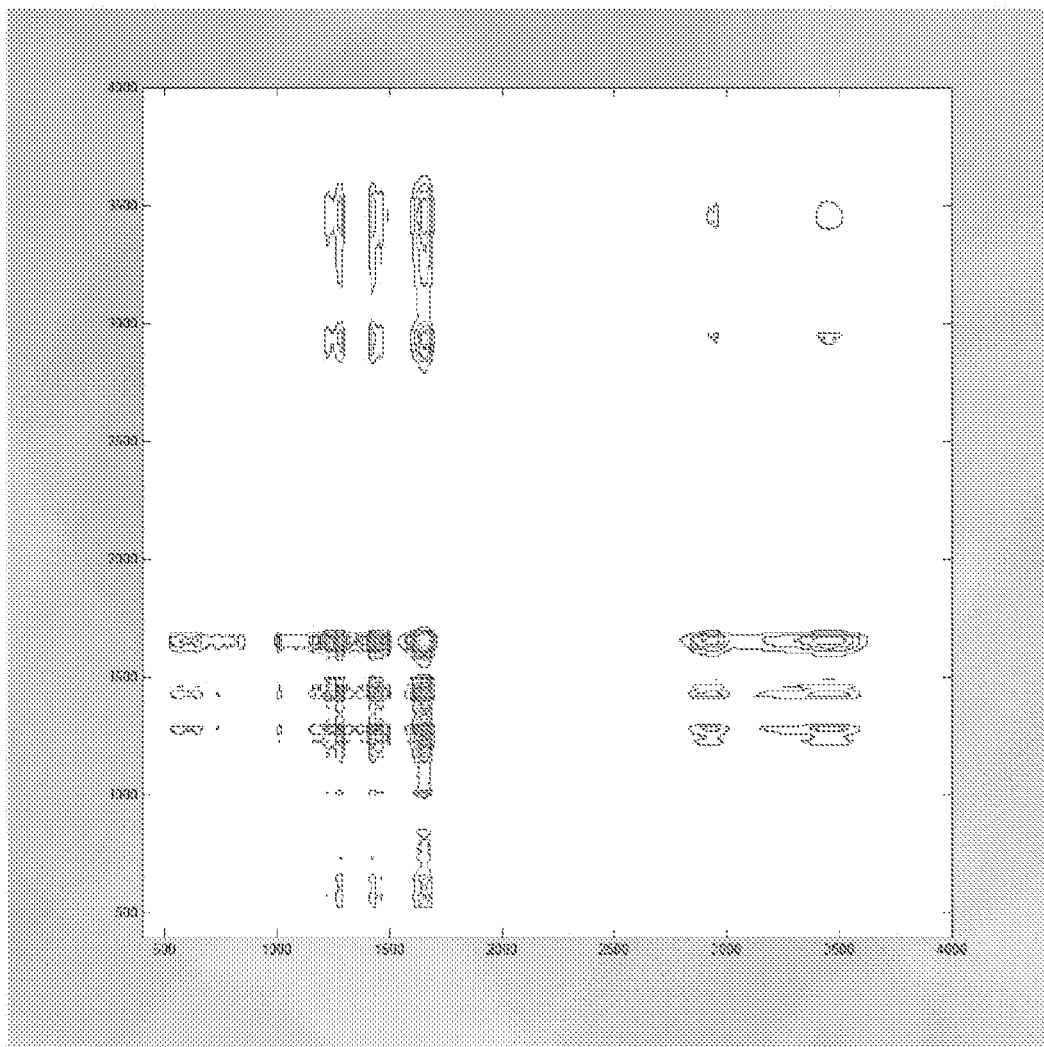
FIG. 23 shows a synchronous spectrum of Povidone
Figure 24:
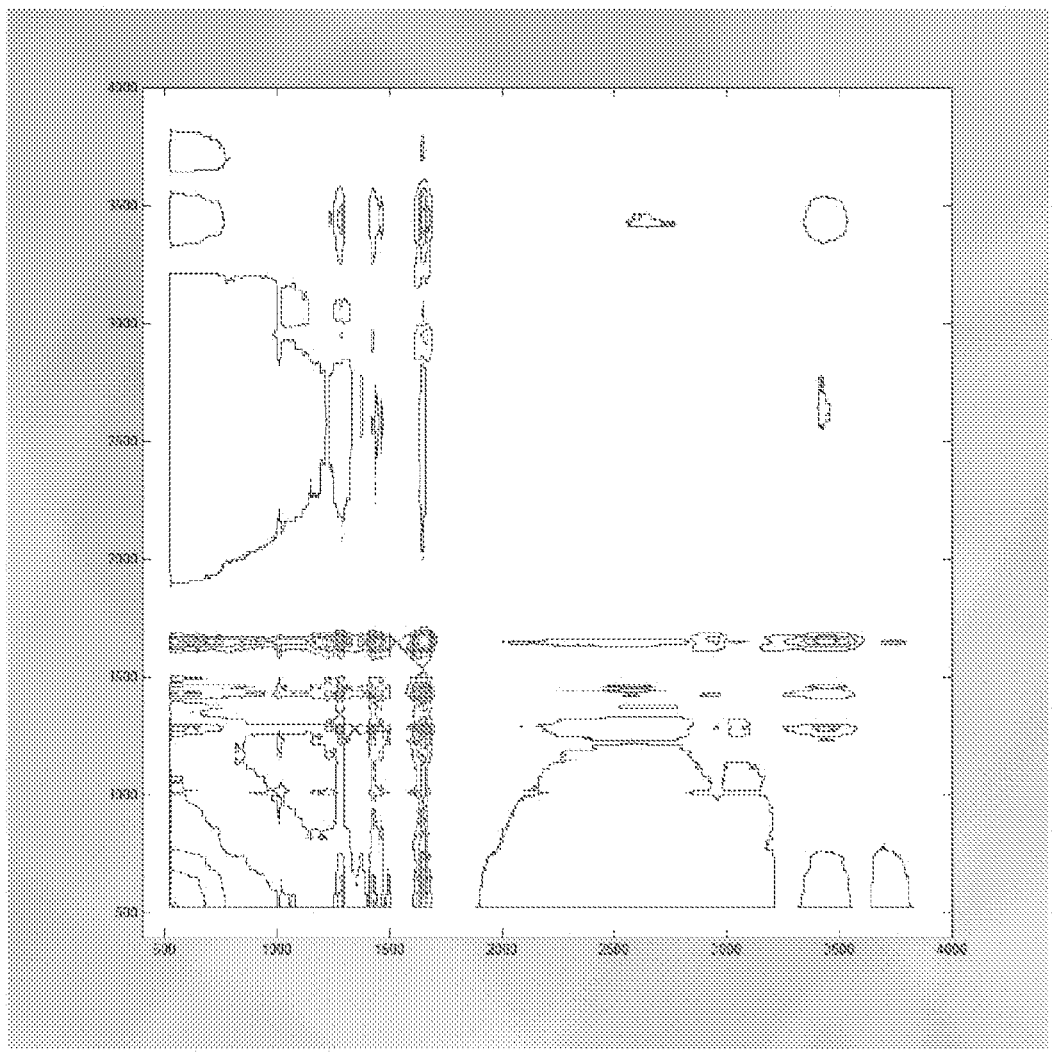
FIG. 24 shows a synchronous spectrum of Povidone (high sensitivity)
Figure 25:
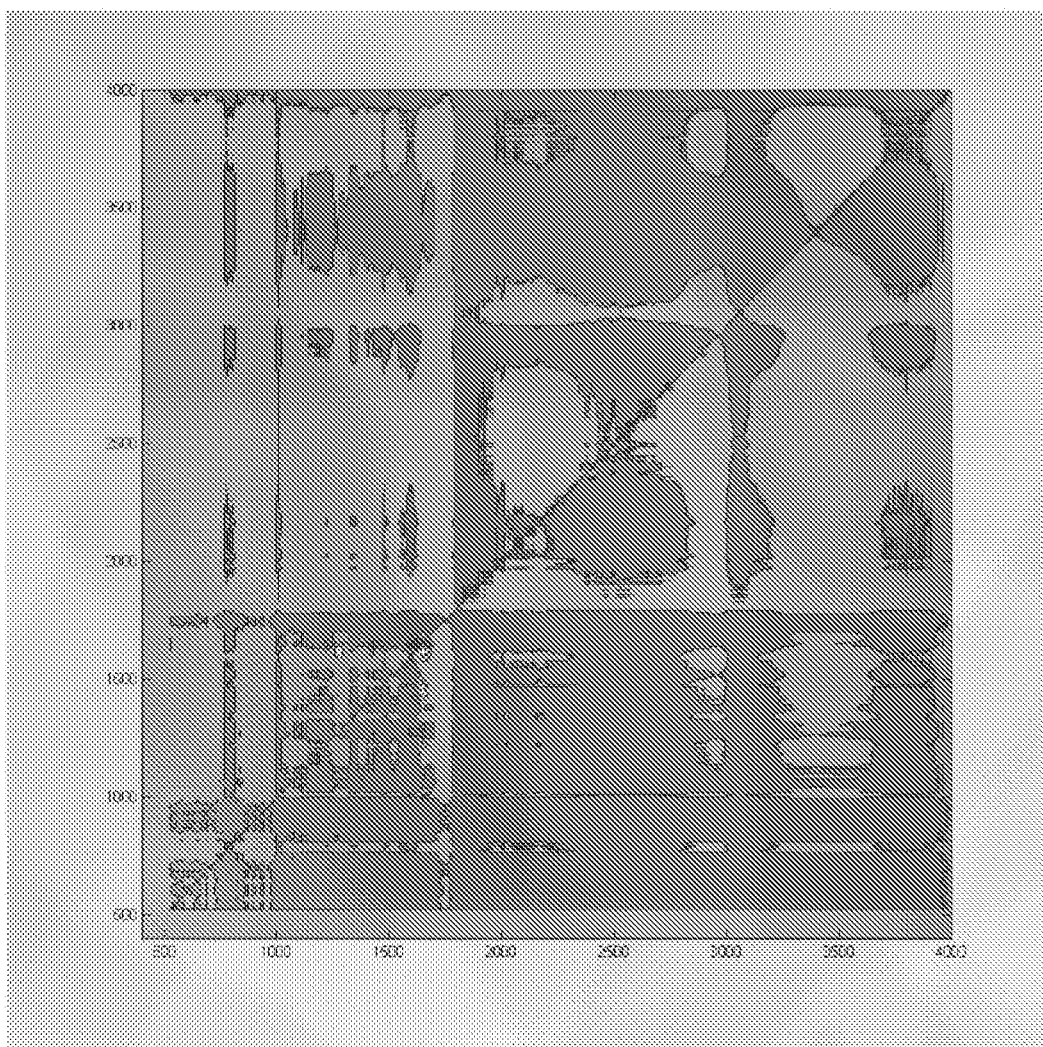
FIG. 25 shows an asynchronous spectrum of Povidone
Figure 26:
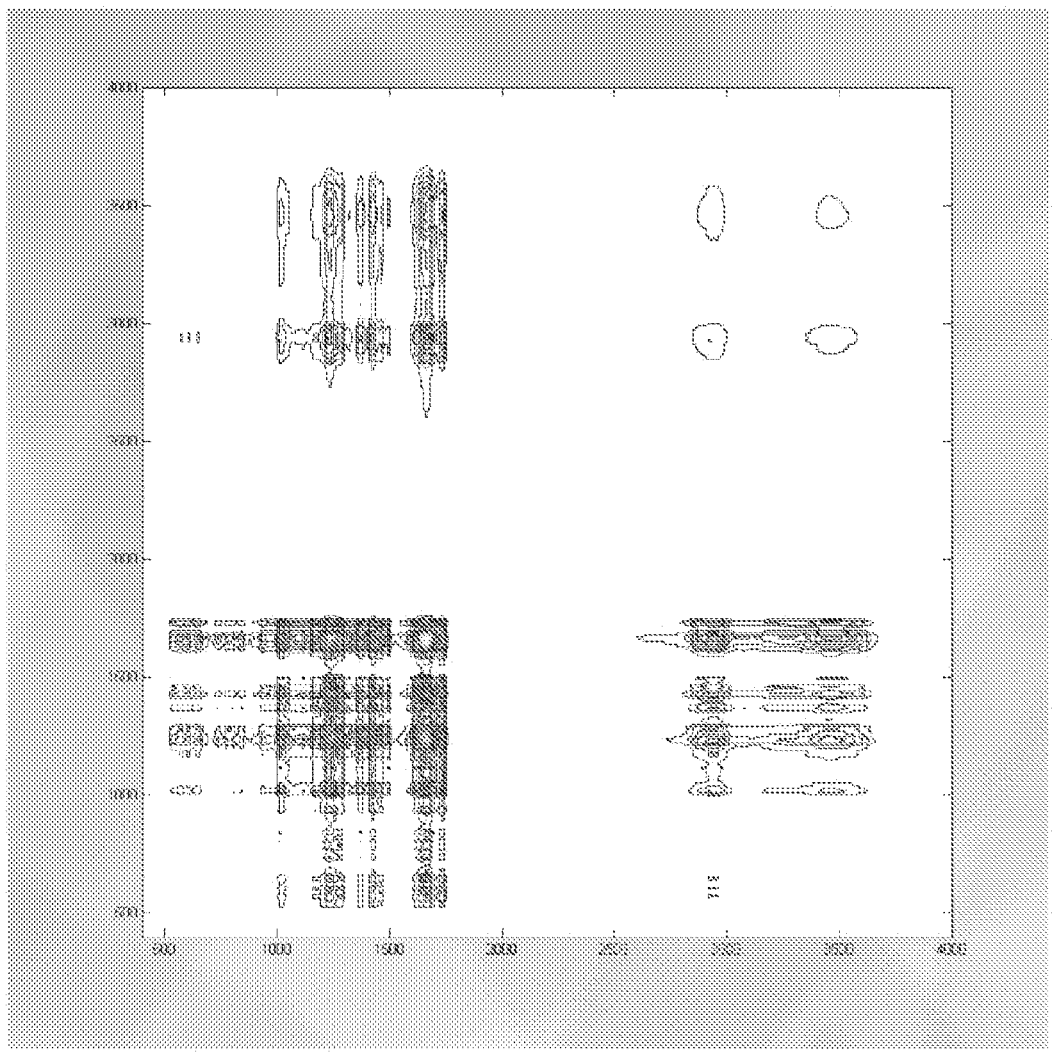
FIG. 26 shows a synchronous spectrum of Copovidone
Figure 27:
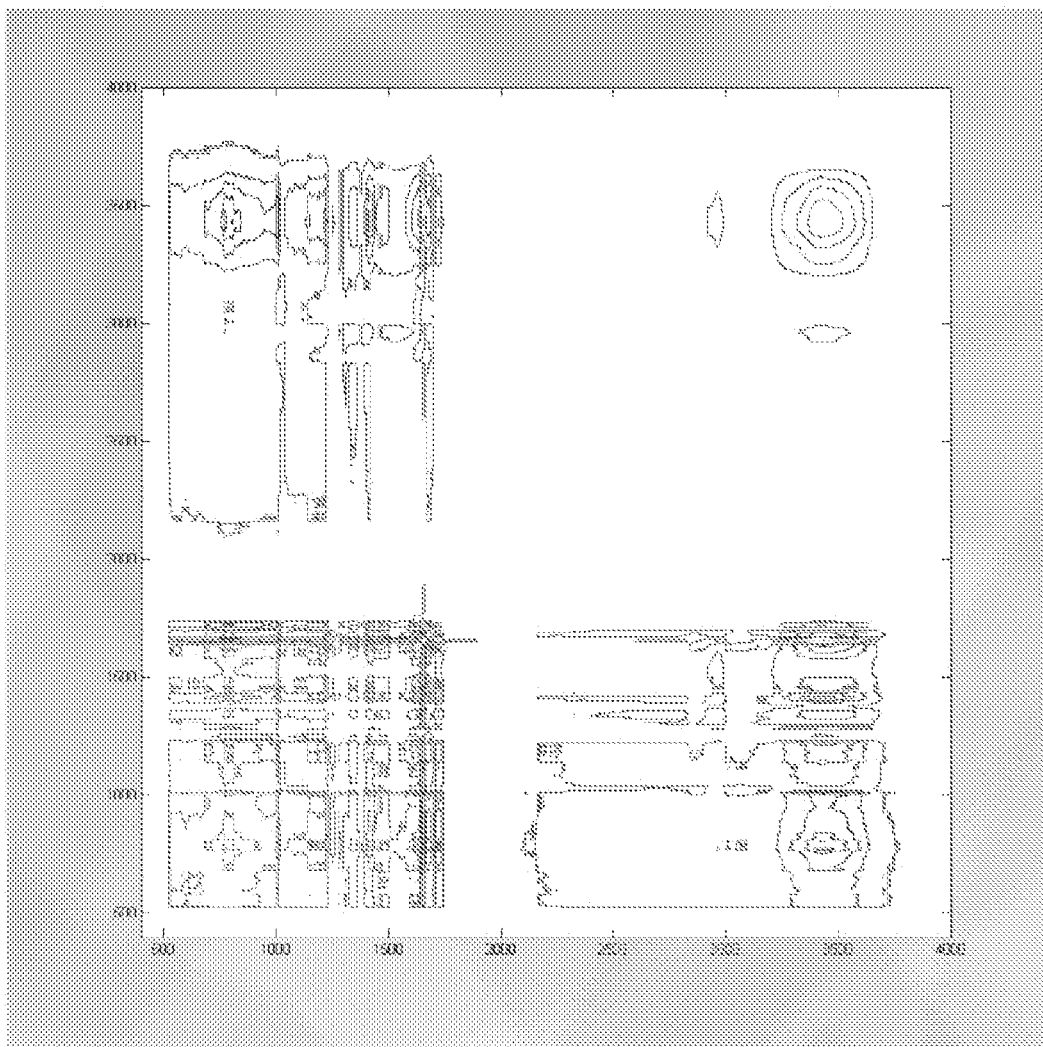
FIG. 27 shows a synchronous spectrum of Copovidone (high sensitivity)
Figure 28:
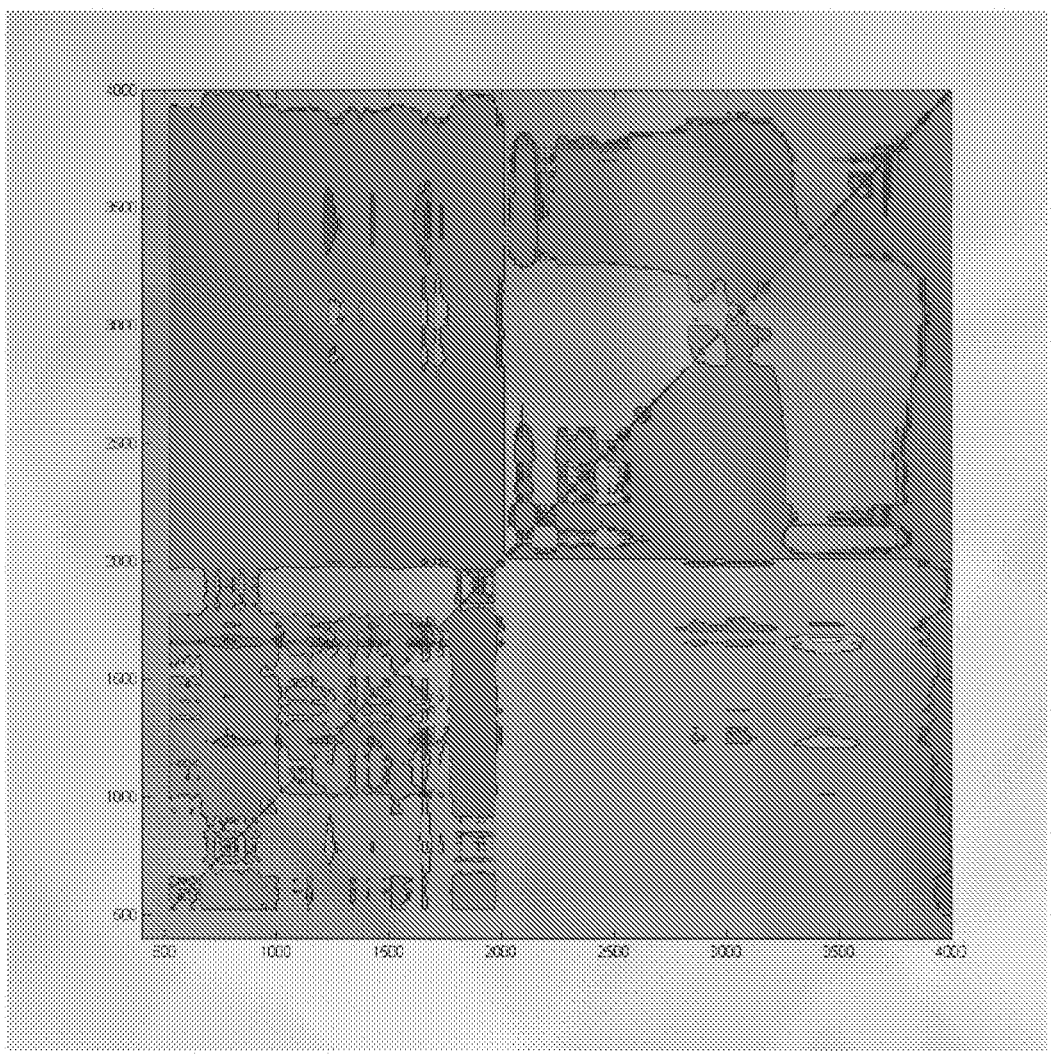
FIG. 28 shows an asynchronous spectrum of Copovidone
Figure 29:
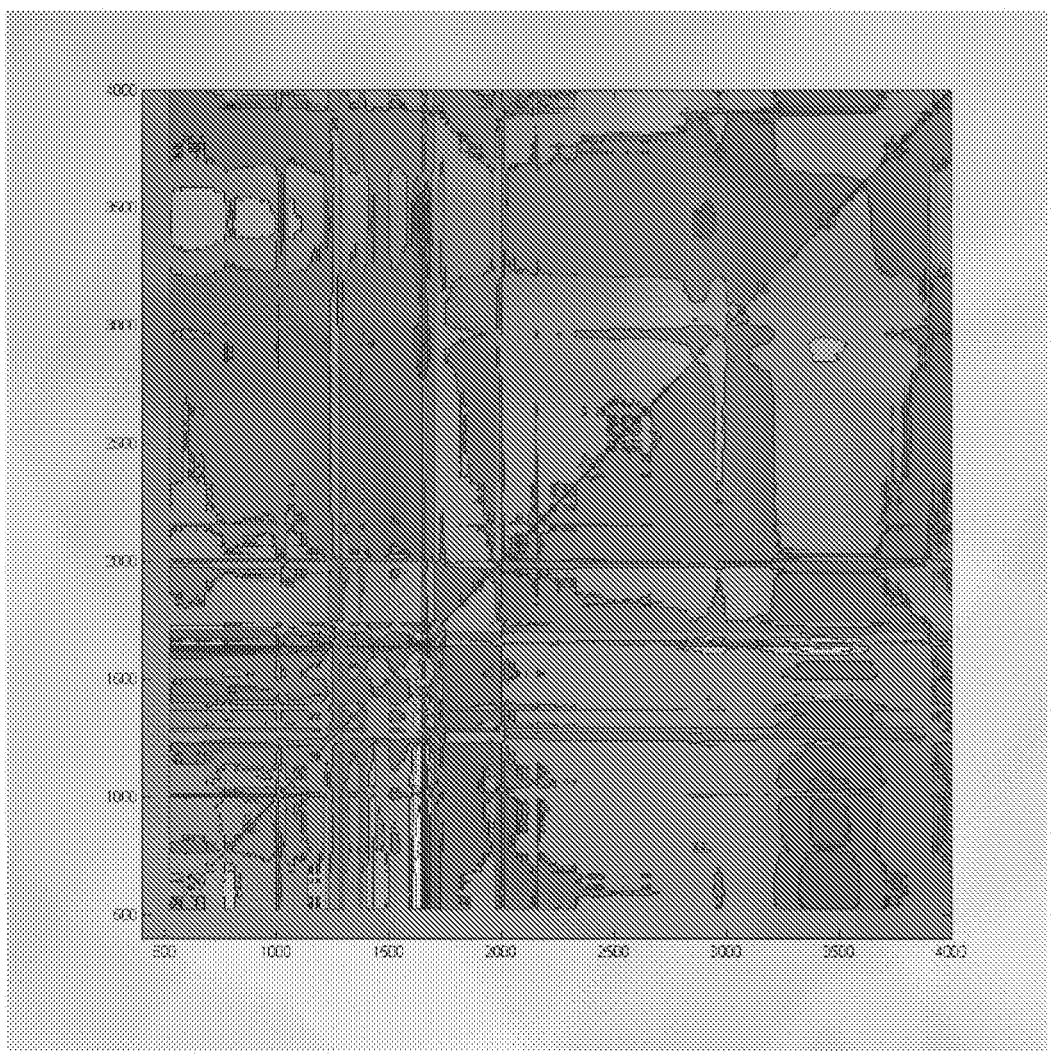
FIG. 29 shows an asynchronous spectrum of Copovidone (high sensitivity)

The primary band in the infrared spectrum of povidone (FIG. 14) is at 1600 cm$^{-1}$ and overlaps with the primary band in the infrared spectrum of Compound 1 (FIG. 13). The synchronous (FIGS. 23 and 24) and asynchronous (FIG. 25) correlation spectra indicate hydrogen bonding interactions.

Copovidone (Kollidon VA64)

Copovidone has many of the same infrared (FIG. 2) and 2D spectral features (FIGS. 26-29) as Povidone but also exhibits additional factors suggesting a greater strength of hydrogen bonding.

5.5.4 Conclusions

The degree of intermolecular interaction observed in solid dispersions of Compound 1 is highly dependent upon the nature of the matrix polymer. The overall ranking of the intermolecular interactions is shown in Table 25.

TABLE 25

Molecular Interaction Ranking

| Polymer | Interaction | Strength | Rank |
|---|---|---|---|
| Aqoat MG | Dipole-dipole | Very Weak | 5 |
| HP55S | Dipole-dipole | Weak | 4 |
| Pharmacoat | Dipole-dipole | Medium to Weak | 3 |
| Povidone | Hydrogen bonding | Strong | 2 |
| Copovidone | Hydrogen bonding | Very Strong | 1 |

These results suggest that solid dispersions of Compound 1 and copovidone may be particularly stable and homogeneous.

EXAMPLE 6. COMPARATIVE BIOAVAILABILITY STUDY 6.1 Protocol

One hundred milligrams of the drug in several different presentations were orally administered to fasted beagle dogs (n=6). The formulations dosed were the IR tablet (see 4.1), microsuspension (see 4.2) and nanosuspension (see 4.5) formulations, capsules containing various drug loadings in Gelucire® 44/14 (see 4.3), capsules containing solid dispersions produced by solvent evaporation (see 4.6.1) and melt extrusion (see 4.6.2) processes, and a tablet prepared from a melt-extruded solid dispersion (see 4.7). The dosing of the tablets and capsules was followed with 20 ml of water whereas 10 mL of the suspension formulations was dosed by gavage and followed by 10 mL of water to wash the gavage tube.

Blood samples were taken post-dose at 0.25, 0.5, 1, 2, 3, 4, 5, 6, 7, 12, 24 and 30 hours. The samples were centrifuged at 3000 rpm for 15 minutes, the plasma removed into plain blood tubes and stored at −20° C. until analysis. Samples were analysed using a manual solid phase extraction (Phenomenex Strata X, 30 mg) method followed by LC-MS using the conditions specified in Table 26 below

TABLE 26

Summary of LC-MS conditions for the determination of Compound 1 in dog plasma

| Chromatographic conditions | |
|---|---|
| Apparatus | Liquid chromatograph with MS/MS detector |

TABLE 26-continued

Summary of LC-MS conditions for the determination of Compound 1 in dog plasma

| Column | Waters Xterra Phenyl, 2.1 mm × 50 mm (3.5 μm) or equivalent |
|---|---|
| Eluents | Ammonium formate (1 mM, pH 3.0)/ Acetonitrile 73:27 v/v) |
| Flow rate | 0.2 mL/min approx. |
| Temperature | 40° C. |
| Wavelength | 276 nm |
| Injection volume | 5 μL |
| Run time | 4 min. |
| Compound 1 retention time | 2.7 min approx. |
| Mass spectrometer parameters | |
| Mode of operation | Ion Spray (positive ion) (MS/MS) |
| Voltage | 4500 V approx. |
| Temperature | 450° C. approx. |
| Ions monitored | 435.3 to 281.2 |

6.2 Results

TABLE 27

Summary of pharmacokinetic data for Compound 1 formulations

| Formulation | $AUC_{(0-inf)}$ (ng · hr · mL$^{-1}$) | $C_p$max (ng · mL$^{-1}$) | Bioavailability relative to copovidone solid dispersion capsule (%) |
|---|---|---|---|
| Immediate Release tablet (25% drug loading) | 7748 | 1225 | 19 |
| Gelucire 44/14 (capsules, 10% drug loading) | 15649 | 2551 | 38 |
| Gelucire 44/14 (capsules, 20% drug loading) | 10078 | 1654 | 25 |
| Gelucire 44/14 (capsules, 40% drug loading) | 7579 | 1174 | 18 |
| Microsuspension (1% drug loading) | 9327 | 1249 | 23 |
| Nanosuspension (1% drug loading) | 22746 | 3922 | 55 |
| Kleptose solid dispersion[1] (capsule; 20% drug loading, 1:3 drug:polymer ratio) | 40373 | 7959 | 98 |
| PVP Solid dispersion[1] (capsule; 20% drug loading, 1:3 drug:polymer ratio) | 35788 | 6810 | 87 |
| AQOAT solid dispersion[1] (capsule; 20% drug loading, 1:3 drug:polymer ratio) | 35450 | 6840 | 86 |
| HPMC-606 solid dispersion[1] (capsule; 20% drug loading, 1:3 drug:polymer ratio) | 31739 | 6179 | 77 |
| HP55S solid dispersion[1] (capsule; 25% drug loading, 1:2 drug:polymer ratio) | 34687 | 6749 | 84 |
| Copovidone solid dispersion[2] (capsule; 20% drug loading; 20:46 drug:polymer ratio) | 41129 | 7707 | 100 |
| Copovidone solid dispersion (tablet; 25% drug loading; 30:70 drug:polymer ratio) | 37745 | 7502 | 92 |

Figure 30:
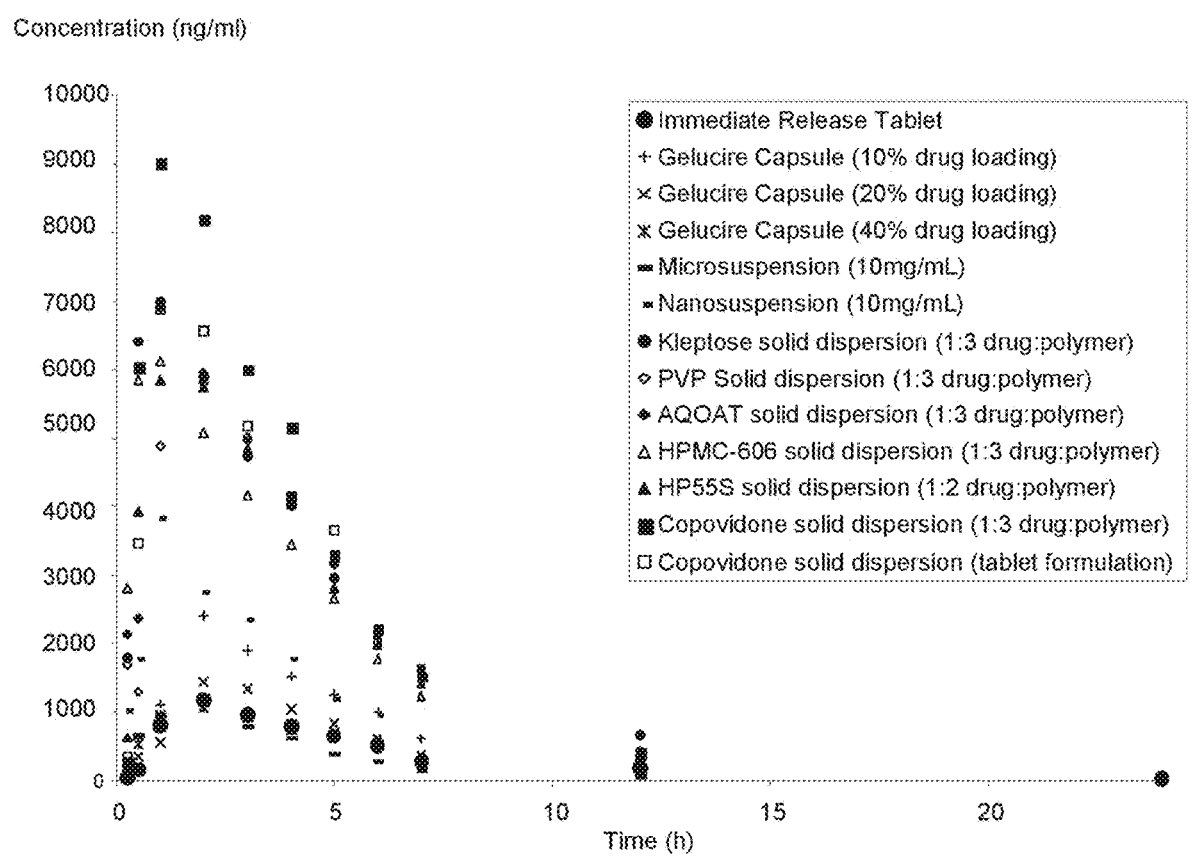
FIG. 30 shows a plot of plasma concentration vs time for the various Compound 1 formulations.

[1]Blended with crospovidone disintegrant (100 mg/capsule) prior to filling
[2]Blended with mannitol/Aerosil (99:1) (167 mg/capsule) prior to filling See FIG. 30. Both $C_p$max and AUC from the polymer-based solid dispersions were significantly greater (P<0.05) than the immediate release tablet, Gelucire capsule and microsuspension/nanosuspension formulations.

The invention claimed is:

1. An immediate-release pharmaceutical composition in the form of a tablet comprising:
   (a) an extrudate comprising:
      (i) 100 mg to 200 mg of 4-[3-(4-cyclopropanecarbonyl-piperazine-1-carbonyl)-4-fluorobenzyl]-2H-phthalazin-1-one (Compound 1);
      (ii) at least one polymer chosen from copovidone, povidone, hypromellose phthalate, hypromellose acetate succinate, 2-hydroxypropyl-β-cyclodextrin, hypromellose, polymethacrylates, hydroxypropyl cellulose, and cellulose acetate phthalate; and
      (iii) at least one glidant; and
   (b) at least one excipient;
   wherein the weight ratio of Compound 1 to the at least one polymer in the extrudate is in the range of from 1:1 to 1:9; and
   wherein the total concentration of Compound 1 in the tablet is in the range of from 10% by weight to 35% by weight.

2. The composition of claim 1, wherein the at least one polymer is chosen from copovidone and povidone.

3. The composition of claim 1, wherein the at least one polymer is a combination of copovidone and povidone.

4. The composition of claim 1, wherein the total concentration of Compound 1 in the extrudate is in the range of from 25% by weight to 50% by weight.

5. The composition of claim 4, wherein the at least one polymer is chosen from copovidone and povidone.

6. The composition of claim 4, wherein the at least one polymer is a combination of copovidone and povidone.

7. The composition of claim 1, wherein the total concentration of the at least one polymer in the extrudate is in the range of from 50% by weight to 75% by weight.

8. The composition of claim 7, wherein the at least one polymer is chosen from copovidone and povidone.

9. The composition of claim 7, wherein the at least one polymer is a combination of copovidone and povidone.

10. The composition of claim 1, wherein the total concentration of Compound 1 in the extrudate is in the range of from 25% by weight to 50% by weight; and wherein the total concentration of the at least one polymer in the extrudate is in the range of from 50% by weight to 75% by weight.

11. The composition of claim 10, wherein the at least one polymer is chosen from copovidone and povidone.

12. The composition of claim 10, wherein the at least one polymer is a combination of copovidone and povidone.

13. The composition of claim 1, wherein the at least one glidant is colloidal silicon dioxide.

14. The composition of claim 13, wherein the at least one polymer is chosen from copovidone and povidone.

15. The composition of claim 14, wherein the at least one polymer is a combination of copovidone and povidone.

16. The composition of claim 1, wherein the total concentration of Compound 1 in the extrudate is in the range of from 25% by weight to 50% by weight; wherein the total concentration of the at least one polymer in the extrudate is in the range of from 50% by weight to 75% by weight; and wherein the at least one glidant is colloidal silicon dioxide.

17. The composition of claim 16, wherein the at least one polymer is chosen from copovidone and povidone.

18. The composition of claim 16, wherein the at least one polymer is a combination of copovidone and povidone.

19. The composition of claim 1, wherein the at least one excipient is chosen from at least one soluble filler and at least one lubricant.

20. The composition of claim 19, wherein the at least one polymer is chosen from copovidone and povidone.

21. The composition of claim 19, wherein the at least one polymer is a combination of copovidone and povidone.

22. The composition of claim 1, wherein the total concentration of Compound 1 in the extrudate is in the range of from 25% by weight to 50% by weight; wherein the total concentration of the at least one polymer in the extrudate is in the range of from 50% by weight to 75% by weight; wherein the at least one glidant is colloidal silicon dioxide; and wherein the at least one excipient is chosen from at least one soluble filler and at least one lubricant.

23. The composition of claim 22, wherein the at least one polymer is chosen from copovidone and povidone.

24. The composition of claim 23, wherein the at least one polymer is a combination of copovidone and povidone.

25. The composition of claim 1, wherein the weight ratio of Compound 1 to the at least one polymer in the extrudate is in the range of from 1:1 to 1:4.

26. The composition of claim 25, wherein the at least one polymer is chosen from copovidone and povidone.

27. The composition of claim 26, wherein the at least one polymer is a combination of copovidone and povidone.

28. The composition of claim 1, wherein the weight ratio of Compound 1 to the at least one polymer in the extrudate is in the range of from 1:1 to 1:4; wherein the at least one glidant is colloidal silicon dioxide; and wherein the at least one excipient is chosen from at least one soluble filler and at least one lubricant.

29. The composition of claim 28, wherein the at least one polymer is chosen from copovidone and povidone.

30. The composition of claim 28, wherein the at least one polymer is a combination of copovidone and povidone.

* * * * *